United States Patent
Fenster et al.

(10) Patent No.: US 10,053,417 B2
(45) Date of Patent: *Aug. 21, 2018

(54) NEPRILYSIN INHIBITORS

(71) Applicant: THERAVANCE BIOPHARMA R&D IP, LLC, South San Francisco, CA (US)

(72) Inventors: Erik Fenster, San Bruno, CA (US); Melissa Fleury, Brisbane, CA (US); Adam D. Hughes, Half Moon Bay, CA (US)

(73) Assignee: THERAVANCE BIOPHARMA R&D IP, LLC, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/806,722

(22) Filed: Nov. 8, 2017

(65) Prior Publication Data

US 2018/0194718 A1    Jul. 12, 2018

Related U.S. Application Data

(63) Continuation of application No. 15/600,998, filed on May 22, 2017, now Pat. No. 9,840,460, which is a
(Continued)

(51) Int. Cl.
*A61K 31/40* (2006.01)
*A61K 31/42* (2006.01)
(Continued)

(52) U.S. Cl.
CPC .......... *C07C 243/38* (2013.01); *A61K 31/192* (2013.01); *A61K 31/197* (2013.01); *A61K 31/341* (2013.01); *A61K 31/397* (2013.01); *A61K 31/40* (2013.01); *A61K 31/4015* (2013.01); *A61K 31/42* (2013.01); *A61K 31/44* (2013.01); *A61K 31/4406* (2013.01); *A61K 31/4409* (2013.01); *A61K 31/495* (2013.01); *A61K 31/5375* (2013.01); *A61K 45/06* (2013.01); *C07C 233/56* (2013.01); *C07C 235/12* (2013.01); *C07C 235/20* (2013.01); *C07C 235/34* (2013.01); *C07C 235/74* (2013.01); *C07C 235/78* (2013.01); *C07C 235/80* (2013.01); *C07C 243/24* (2013.01); *C07C 243/32* (2013.01); *C07C 259/04* (2013.01); *C07D 205/04* (2013.01); *C07D 207/08* (2013.01); *C07D 207/09* (2013.01); *C07D 207/12* (2013.01); *C07D 207/14* (2013.01); *C07D 207/16* (2013.01); *C07D 211/22* (2013.01); *C07D 211/38* (2013.01); *C07D 211/42* (2013.01); *C07D 211/46* (2013.01); *C07D 211/48* (2013.01); *C07D 211/60* (2013.01); *C07D 211/62* (2013.01); *C07D 213/56* (2013.01); *C07D 213/61* (2013.01); *C07D 213/65* (2013.01); *C07D 213/75* (2013.01); *C07D 213/86* (2013.01); *C07D 213/87* (2013.01); *C07D 233/06* (2013.01); *C07D 239/36* (2013.01); (Continued)

(58) Field of Classification Search
CPC ........ A61K 31/40; A61K 31/42; A61K 31/44; A61K 31/197; A61K 31/397; A61K 31/5375; C07C 235/34; C07D 205/04; C07D 207/09; C07D 207/14; C07D 213/56; C07D 235/34; C07D 261/04; C07D 295/32

See application file for complete search history.

(56) References Cited

U.S. PATENT DOCUMENTS 4,189,604 A    2/1980 Umezawa et al.
4,206,232 A    6/1980 Ondetti et al.
(Continued)

OTHER PUBLICATIONS

Ksander et al., "Dicarboxylic acid dipeptide neutral endopeptidase inhibitors", Journal of Medicinal Chemistry, 38(10): 1689-1700 (1995).
(Continued)

*Primary Examiner* — Timothy R Rozof
(74) *Attorney, Agent, or Firm* — Jeffrey A. Hagenah; Wendy Petka

(57) ABSTRACT

In one aspect, the invention relates to compounds having the formula:

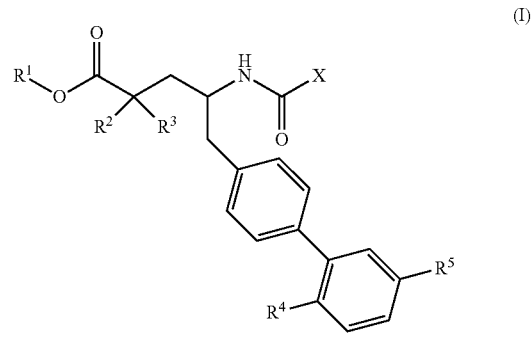

where $R^1$-$R^5$ and X are as defined in the specification, or a pharmaceutically acceptable salt thereof. These compounds have neprilysin inhibition activity. In another aspect, the invention relates to pharmaceutical compositions comprising such compounds; methods of using such compounds; and processes and intermediates for preparing such compounds.

5 Claims, No Drawings

Related U.S. Application Data continuation of application No. 15/219,478, filed on Jul. 26, 2016, now Pat. No. 9,688,616, which is a continuation of application No. 14/749,949, filed on Jun. 25, 2015, now Pat. No. 9,428,457, which is a continuation of application No. 14/516,866, filed on Oct. 17, 2014, now Pat. No. 9,096,496, which is a continuation of application No. 14/196,624, filed on Mar. 4, 2014, now Pat. No. 8,901,169.

(60) Provisional application No. 61/772,721, filed on Mar. 5, 2013.

(51) Int. Cl.

| | | |
|---|---|---|
| A61K 31/44 | (2006.01) | |
| A61K 31/197 | (2006.01) | |
| A61K 31/397 | (2006.01) | |
| A61K 31/5375 | (2006.01) | |
| C07D 205/04 | (2006.01) | |
| C07D 207/09 | (2006.01) | |
| C07D 207/14 | (2006.01) | |
| C07D 213/56 | (2006.01) | |
| C07C 235/34 | (2006.01) | |
| C07D 261/04 | (2006.01) | |
| C07D 295/32 | (2006.01) | |
| C07C 243/38 | (2006.01) | |
| A61K 31/341 | (2006.01) | |
| A61K 31/4409 | (2006.01) | |
| C07D 213/86 | (2006.01) | |
| C07D 213/87 | (2006.01) | |
| C07C 235/80 | (2006.01) | |
| A61K 31/4406 | (2006.01) | |
| A61K 31/192 | (2006.01) | |
| C07D 213/65 | (2006.01) | |
| A61K 45/06 | (2006.01) | |
| A61K 31/495 | (2006.01) | |
| A61K 31/4015 | (2006.01) | |
| C07D 307/68 | (2006.01) | |
| C07D 213/61 | (2006.01) | |
| C07D 211/62 | (2006.01) | |
| C07D 211/60 | (2006.01) | |
| C07D 211/48 | (2006.01) | |
| C07D 211/46 | (2006.01) | |
| C07D 211/42 | (2006.01) | |
| C07D 211/38 | (2006.01) | |
| C07D 211/22 | (2006.01) | |
| C07C 243/32 | (2006.01) | |
| C07C 243/24 | (2006.01) | |
| C07D 493/10 | (2006.01) | |
| C07D 207/16 | (2006.01) | |
| C07D 207/12 | (2006.01) | |
| C07D 207/08 | (2006.01) | |
| C07D 265/30 | (2006.01) | |
| C07C 235/78 | (2006.01) | |
| C07C 235/74 | (2006.01) | |
| C07C 235/20 | (2006.01) | |
| C07C 235/12 | (2006.01) | |
| C07C 233/56 | (2006.01) | |
| C07D 261/02 | (2006.01) | |
| C07D 239/36 | (2006.01) | |
| C07D 405/06 | (2006.01) | |
| C07D 401/04 | (2006.01) | |
| C07D 233/06 | (2006.01) | |
| C07D 309/08 | (2006.01) | |
| C07C 259/04 | (2006.01) | |
| C07D 213/75 | (2006.01) | |
| C07D 491/107 | (2006.01) | |

(52) U.S. Cl.
CPC ......... *C07D 261/02* (2013.01); *C07D 261/04* (2013.01); *C07D 265/30* (2013.01); *C07D 295/32* (2013.01); *C07D 307/68* (2013.01); *C07D 309/08* (2013.01); *C07D 401/04* (2013.01); *C07D 405/06* (2013.01); *C07D 491/107* (2013.01); *C07D 493/10* (2013.01); *C07C 2601/08* (2017.05); *C07C 2601/16* (2017.05)

(56) References Cited

U.S. PATENT DOCUMENTS

| | | |
|---|---|---|
| 4,374,829 A | 2/1983 | Harris et al. |
| 4,513,009 A | 4/1985 | Rogues et al. |
| 4,722,810 A | 2/1988 | Delaney et al. |
| 4,906,615 A | 3/1990 | Berger et al. |
| 4,929,641 A | 5/1990 | Haslanger et al. |
| 4,939,261 A | 7/1990 | Ksander |
| 4,975,444 A | 12/1990 | Danilewicz et al. |
| 5,021,430 A | 6/1991 | Ksander |
| 5,030,654 A | 7/1991 | Bamish et al. |
| 5,155,100 A | 10/1992 | Erion et al. |
| 5,208,255 A | 5/1993 | Duhamel et al. |
| 5,217,996 A | 6/1993 | Ksander |
| 5,294,632 A | 3/1994 | Erion et al. |
| 5,508,272 A | 4/1996 | Robl |
| 5,599,951 A | 2/1997 | Plaquevent et al. |
| 5,677,297 A | 10/1997 | Waldeck et al. |
| 5,977,075 A | 11/1999 | Ksander et al. |
| 6,602,866 B2 | 8/2003 | Flynn et al. |
| 6,660,756 B2 | 9/2003 | Challenger et al. |
| 8,449,890 B2 | 5/2013 | Fleury et al. |
| 8,481,044 B2 | 7/2013 | Fleury et al. |
| 8,513,244 B2 | 8/2013 | Gendron et al. |
| 8,563,512 B2 | 10/2013 | Smith et al. |
| 8,586,536 B2 | 11/2013 | Gendron et al. |
| 8,686,184 B2 | 4/2014 | Fleury et al. |
| 8,691,868 B2 | 4/2014 | Hughes et al. |
| 8,871,792 B2 | 10/2014 | Hughes et al. |
| 8,901,169 B2 | 12/2014 | Fenster et al. |
| 9,045,443 B2 | 6/2015 | Mammen et al. |
| 9,096,496 B2 | 8/2015 | Fenster et al. |
| 9,108,934 B2 | 8/2015 | Hughes et al. |
| 9,126,956 B2 | 9/2015 | Fleury et al. |
| 9,428,457 B2 | 8/2016 | Fenster et al. |
| 9,688,616 B2 | 6/2017 | Fenster et al. |
| 9,840,460 B2 | 12/2017 | Fenster et al. |
| 2010/0113801 A1 | 5/2010 | Hook et al. |
| 2010/0305131 A1 | 12/2010 | Coppola et al. |
| 2010/0305145 A1 | 12/2010 | Coppola et al. |
| 2011/0046397 A1 | 2/2011 | Hook et al. |
| 2011/0124695 A1 | 5/2011 | Iwaki et al. |
| 2012/0122844 A1 | 5/2012 | Foo |
| 2012/0122977 A1 | 5/2012 | Coppola et al. |
| 2012/0289710 A1 | 11/2012 | Hook et al. |
| 2012/0309724 A1 | 12/2012 | Fleury et al. |
| 2015/0209352 A1 | 7/2015 | Fleury et al. |
| 2015/0210690 A1 | 7/2015 | Fleury et al. |

OTHER PUBLICATIONS

Misawa et al., "Structure-based design of dipeptide derivatives for the human neutral endopeptidase", BioOrganic & Medicinal Chemistry, 19: 5935-5947 (2011).

PCT International Search Report for PCT/US2014/020291 dated May 28, 2014.

NEPRILYSIN INHIBITORS

CROSS-REFERENCE TO RELATED APPLICATIONS

This application is a continuation of U.S. application Ser. No. 15/600,998, filed on May 22, 2017, now allowed: which is a continuation of U.S. application Ser. No. 15/219,478, filed on Jul. 26, 2016, now U.S. Pat. No. 9,688,616 B2: which is a continuation of U.S. application Ser. No. 14/749, 949, filed on Jun. 25, 2015, now U.S. Pat. No. 9,428,457 B2; which is a continuation of U.S. application Ser. No. 14/516, 866, filed on Oct. 17, 2014, now U.S. Pat. No. 9,096,496 B2: which is a continuation of U.S. application Ser. No. 14/196, 624, filed on Mar. 4, 2014, now U.S. Pat. No. 8,901,169 B2: which application claims the benefit of U.S. Provisional Application No. 61/772,721, filed on Mar. 5, 2013; the entire disclosures of which are is incorporated herein by reference.

BACKGROUND OF THE INVENTION

Field of the Invention

The present invention relates to novel compounds having neprilysin-inhibition activity. The invention also relates to pharmaceutical compositions comprising such compounds, processes and intermediates for preparing such compounds and methods of using such compounds to treat diseases such as hypertension, heart failure, pulmonary hypertension, and renal disease.

State of the Art

Neprilysin (neutral endopeptidase, EC 3.4.24.11) (NEP), is an endothelial membrane bound $Zn^{2+}$ metallopeptidase found in many organs and tissues, including the brain, kidneys, lungs, gastrointestinal tract, heart, and the peripheral vasculature. NEP degrades and inactivates a number of endogenous peptides, such as enkephalins, circulating bradykinin, angiotensin peptides, and natriuretic peptides, the latter of which have several effects including, for example, vasodilation and natriuresis/diuresis, as well as inhibition of cardiac hypertrophy and ventricular fibrosis. Thus, NEP plays an important role in blood pressure homeostasis and cardiovascular health.

NEP inhibitors, such as thiorphan, candoxatril, and candoxatrilat, have been studied as potential therapeutics. Compounds that inhibit both NEP and angiotensin-I converting enzyme (ACE) are also known, and include omapatrilat, gempatrilat, and sampatrilat. Referred to as vasopeptidase inhibitors, this latter class of compounds is described in Robl et al. (1999) *Exp. Opin. Ther. Patents* 9(12): 1665-1677.

SUMMARY OF THE INVENTION

The present invention provides novel compounds that have been found to possess neprilysin (NEP) enzyme inhibition activity. Accordingly, compounds of the invention are expected to be useful and advantageous as therapeutic agents for treating conditions such as hypertension and heart failure.

One aspect of the invention relates to a compound of formula I:

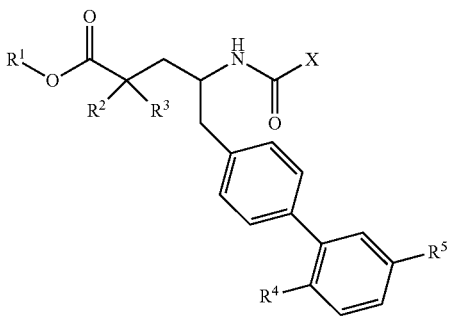

where:
$R^1$ is selected from the group consisting of H; $C_{1-8}$alkyl optionally substituted with one or more fluoro atoms; $C_{1-3}$alkylene-$C_{6-10}$aryl; $C_{1-3}$alkylene-$C_{1-9}$heteroaryl; $C_{3-7}$cycloalkyl; $C_{2-3}$alkylene-OH; —[$(CH_2)_2O]_{1-3}CH_3$; $C_{1-6}$alkylene-OC(O)$R^{20}$; $C_{1-6}$alkylene-NR$^{21}$R$^{22}$; —$CH_2CH(NH_2)$—COOCH$_3$; $C_{1-6}$alkylene-C(O)$R^{23}$; $C_{0-6}$alkylenemorpholine; $C_{1-6}$alkylene-SO$_2$—$C_{1-6}$alkyl;

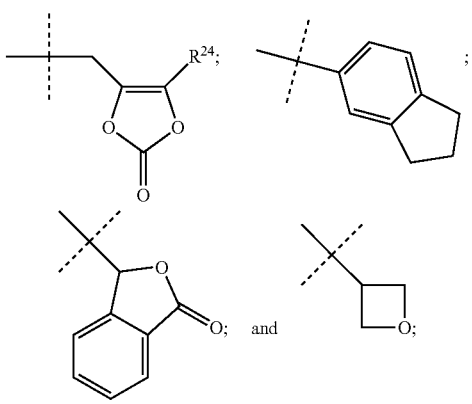

where $R^{20}$ is selected from the group consisting of $C_{1-6}$alkyl, —O—$C_{1-6}$alkyl, $C_{3-7}$cycloalkyl, —O—$C_{3-7}$cycloalkyl, phenyl, —O-phenyl, —NR$^{21}$R$^{22}$, —CH($R^{25}$)—NH$_2$, —CH($R^{25}$)—NHC(O)O—$C_{1-6}$alkyl, and —CH(NH$_2$)CH$_2$COOCH$_3$; and $R^{21}$ and $R^{22}$ are independently selected from the group consisting of H, $C_{1-6}$alkyl, and benzyl; or $R^{21}$ and $R^{22}$ are taken together as —$(CH_2)_{3-6}$—, —C(O)—$(CH_2)_3$—, or —$(CH_2)_2O(CH_2)_2$—; $R^{23}$ is selected from the group consisting of —O—$C_{1-6}$alkyl, —O-benzyl, and —NR$^{21}$R$^{22}$; $R^{24}$ is $C_{1-6}$alkyl or $C_{0-6}$alkylene-$C_{6-10}$aryl; and $R^{25}$ is H, —CH$_3$, —CH(CH$_3$)$_2$, phenyl, or benzyl;
$R^2$ is —OH, —CH$_2$OH, or —CH$_2$—O—$C_{1-6}$alkyl; and $R^3$ is H or —CH$_3$;
$R^4$ and $R^5$ are independently selected from the group consisting of hydrogen, halo, —OH, —CH$_3$, —OCH$_3$, —CN, and —CF$_3$;
X is H, —C(O)—$R^6$, —C(O)—NR$^7$R$^8$, —C(O)—NR$^9$—NR$^{10}$R$^{11}$, —C(O)—NR$^{12}$—NR$^{13}$—C(O)—R$^{14}$, or —CH($R^{15}$)—OR$^{16}$;
$R^6$ is $C_{1-6}$alkyl, $C_{1-6}$alkylene-O—$C_{1-6}$alkyl, $C_{6-10}$aryl, benzyl, or $C_{1-9}$heteroaryl;
$R^7$ is H, —OH, or $C_{1-6}$alkyl;
$R^8$ is $C_{1-6}$alkyl; —O—$C_{1-6}$alkyl; $C_{5-6}$cycloalkyl; $C_{6-10}$aryl; —O—$C_{6-10}$aryl; —O-benzyl; pyridine optionally substituted with halo, —OH, $C_{1-6}$alkyl, or —O—$C_{1-6}$alkyl;

morpholine; or isoxazolidinone; or R⁷ and R⁸ are taken together to form a ring selected from the group consisting of:

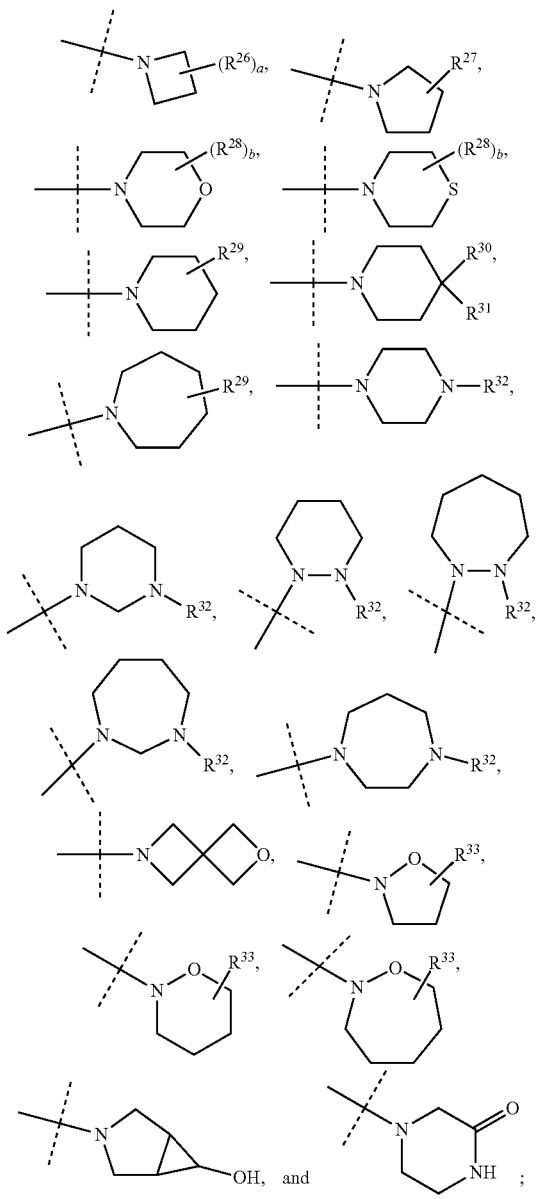

where a is 1 and R²⁶ is —OH, or a is 2 and each R²⁶ is independently halo or —C$_{1-3}$alkylene-OH; R²⁷ is —C$_{1-3}$alkylene-OH, —C(O)NH₂, or —SO₂CH₃; b is 0, or b is 1 and R²⁸ is —C$_{1-3}$alkylene-OH, or b is 2 and each R²⁸ is C$_{1-6}$alkyl; R²⁹ is halo, —COOH, —OH, —C$_{1-3}$alkylene-OH, —CH₂O—CH₃, —CONH₂, —CN, or pyridine; R³⁰ is C$_{1-6}$alkyl or C$_{3-7}$cycloalkyl; R³¹ is —OH or —C$_{1-3}$alkylene-OH; R³² is halo; C$_{1-6}$alkyl; C$_{2-4}$alkylene-O—C$_{1-6}$alkyl; —C(O)O—C$_{1-6}$alkyl; —C(O)N(CH₃)₂; pyridine; —SO₂CH₃; —C(O)-furan; or phenyl substituted with halo, —O—C$_{1-6}$alkyl, or —CN; and R³³ is H, —OH, —O—C$_{1-6}$alkyl or —O—C$_{6-10}$aryl;

R⁹ is H or C$_{1-6}$alkyl;

R¹⁰ is H or C$_{1-6}$alkyl;

R¹¹ is C$_{1-6}$alkyl; C$_{1-9}$heteroaryl optionally substituted with halo, —OH, C$_{1-6}$alkyl, or —O—C$_{1-6}$alkyl; dihydroimidazole; or phenyl optionally substituted with one or two groups selected from the group consisting of halo, C$_{1-6}$alkyl, —O—C$_{1-6}$alkyl, and —NO₂;

R¹² is H or C$_{1-6}$alkyl;

R¹³ is H or C$_{1-6}$alkyl;

R¹⁴ is —O-benzyl; pyridine optionally substituted with halo, —OH, C$_{1-6}$alkyl, or —O—C$_{1-6}$alkyl; furan; or phenyl substituted with halo, —OH, —O—C$_{1-6}$alkyl, or —NO₂;

R¹⁵ H or C$_{1-6}$alkyl;

R¹⁶ is H, C$_{1-6}$alkyl, —[(CH₂)₂O]$_{1-3}$CH₃, C$_{1-9}$heteroaryl, benzyl, or C$_{6-10}$aryl optionally substituted with —OH or —OCH₃; or R¹⁵ and R¹⁶ are taken together to form —(CH₂)₄—;

or a pharmaceutically acceptable salt thereof.

Another aspect of the invention relates to pharmaceutical compositions comprising a pharmaceutically acceptable carrier and a compound of the invention. Such compositions may optionally contain other therapeutic agents. Accordingly, in yet another aspect of the invention, a pharmaceutical composition comprises a compound of the invention as the first therapeutic agent, one or more secondary therapeutic agent, and a pharmaceutically acceptable carrier. Another aspect of the invention relates to a combination of active agents, comprising a compound of the invention and a second therapeutic agent. The compound of the invention can be formulated together or separately from the additional agent(s). When formulated separately, a pharmaceutically acceptable carrier may be included with the additional agent(s). Thus, yet another aspect of the invention relates to a combination of pharmaceutical compositions, the combination comprising: a first pharmaceutical composition comprising a compound of the invention and a first pharmaceutically acceptable carrier; and a second pharmaceutical composition comprising a second therapeutic agent and a second pharmaceutically acceptable carrier. In another aspect, the invention relates to a kit containing such pharmaceutical compositions, for example where the first and second pharmaceutical compositions are separate pharmaceutical compositions.

Compounds of the invention possess NEP enzyme inhibition activity, and are therefore expected to be useful as therapeutic agents for treating patients suffering from a disease or disorder that is treated by inhibiting the NEP enzyme or by increasing the levels of its peptide substrates. Thus, one aspect of the invention relates to a method of treating patients suffering from a disease or disorder that is treated by inhibiting the NEP enzyme, comprising administering to a patient a therapeutically effective amount of a compound of the invention. Another aspect of the invention relates to a method of treating hypertension, heart failure, or renal disease, comprising administering to a patient a therapeutically effective amount of a compound of the invention. Still another aspect of the invention relates to a method for inhibiting a NEP enzyme in a mammal comprising administering to the mammal, a NEP enzyme-inhibiting amount of a compound of the invention.

Since compounds of the invention possess NEP inhibition activity, they are also useful as research tools. Accordingly, one aspect of the invention relates to a method of using a compound of the invention as a research tool, the method comprising conducting a biological assay using a compound of the invention. Compounds of the invention can also be used to evaluate new chemical compounds. Thus another aspect of the invention relates to a method of evaluating a test compound in a biological assay, comprising: (a) conducting a biological assay with a test compound to provide a first assay value; (b) conducting the biological assay with a compound of the invention to provide a second assay value; wherein step (a) is conducted either before, after or concurrently with step (b); and (c) comparing the first assay value from step (a) with the second assay value from step (b). Exemplary biological assays include a NEP enzyme inhibition assay. Still another aspect of the invention relates to a method of studying a biological system or sample comprising a NEP enzyme, the method comprising: (a) contacting the biological system or sample with a compound of the invention; and (b) determining the effects caused by the compound on the biological system or sample.

Yet another aspect of the invention relates to processes and intermediates useful for preparing compounds of the invention. Accordingly, another aspect of the invention relates to a process of preparing compounds of formula I, comprising the step of coupling (i) a compound of formula 1:

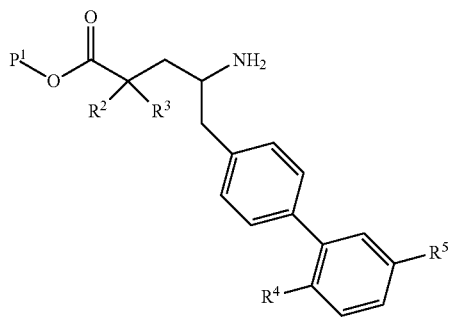

(1)

with a compound of formula 2 or formula 7 or formula 8 or formic acid:

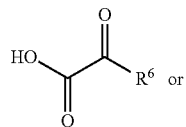

(2)

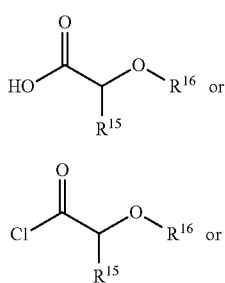

(7)

(8)

or (ii) a compound of formula 3:

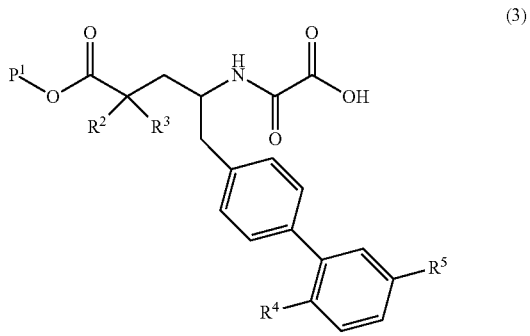

(3)

with a compound of formula 4 or formula 5 or formula 6:

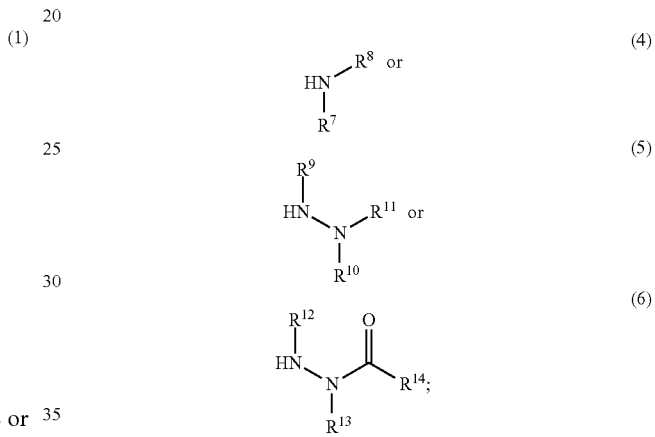

(4)

(5)

(6)

to produce a compound of formula I; where $P^1$ is H or a carboxy protecting group selected from methyl, ethyl, t-butyl, benzyl, p-methoxybenzyl, 9-fluorenylmethyl, trimethylsilyl, t-butyldimethylsilyl, and diphenylmethyl; and where the process further comprises deprotecting the compound of formula I when $P^1$ is a carboxy protecting group; and where $R^2$-$R^{16}$, are as defined for formula I. Another aspect of the invention relates to a process of preparing a pharmaceutically acceptable salt of a compound of formula I, comprising contacting a compound of formula I in free acid or base form with a pharmaceutically acceptable base or acid. In other aspects, the invention relates to products prepared by any of the processes described herein, as well as novel intermediates used in such process.

Yet another aspect of the invention relates to the use of a compound of formula I or a pharmaceutically acceptable salt thereof, for the manufacture of a medicament, especially for the manufacture of a medicament useful for treating hypertension, heart failure, or renal disease. Another aspect of the invention relates to use of a compound of the invention for inhibiting a NEP enzyme in a mammal. Still another aspect of the invention relates to the use of a compound of the invention as a research tool. Other aspects and embodiments of the invention are disclosed herein.

DETAILED DESCRIPTION OF THE INVENTION

Definitions

When describing the compounds, compositions, methods and processes of the invention, the following terms have the following meanings unless otherwise indicated. Additionally, as used herein, the singular forms "a," "an," and "the" include the corresponding plural forms unless the context of use clearly dictates otherwise. The terms "comprising", "including," and "having" are intended to be inclusive and mean that there may be additional elements other than the listed elements. All numbers expressing quantities of ingredients, properties such as molecular weight, reaction conditions, and so forth used herein are to be understood as being modified in all instances by the term "about," unless otherwise indicated. Accordingly, the numbers set forth herein are approximations that may vary depending upon the desired properties sought to be obtained by the present invention. At least, and not as an attempt to limit the application of the doctrine of equivalents to the scope of the claims, each number should at least be construed in light of the reported significant digits and by applying ordinary rounding techniques.

The term "alkyl" means a monovalent saturated hydrocarbon group which may be linear or branched. Unless otherwise defined, such alkyl groups typically contain from 1 to 10 carbon atoms and include, for example, $C_{1-4}$alkyl, $C_{1-5}$alkyl, $C_{2-5}$alkyl, $C_{1-6}$alkyl, $C_{2-6}$alkyl, $C_{1-8}$alkyl, and $C_{1-10}$alkyl. Representative alkyl groups include, by way of example, methyl, ethyl, n-propyl, isopropyl, n-butyl, s-butyl, isobutyl, t-butyl, n-pentyl, n-hexyl, n-heptyl, n-octyl, n-nonyl, n-decyl and the like.

When a specific number of carbon atoms is intended for a particular term used herein, the number of carbon atoms is shown preceding the term as subscript. For example, the term "$C_{1-6}$alkyl" means an alkyl group having from 1 to 6 carbon atoms, and the term "$C_{3-7}$cycloalkyl" means a cycloalkyl group having from 3 to 7 carbon atoms, respectively, where the carbon atoms are in any acceptable configuration.

The term "alkylene" means a divalent saturated hydrocarbon group that may be linear or branched. Unless otherwise defined, such alkylene groups typically contain from 0 to 10 carbon atoms and include, for example, $C_{0-1}$alkylene, $C_{0-2}$alkylene, $C_{0-6}$alkylene, $C_{1-3}$alkylene, $C_{1-6}$alkylene, and $C_{2-4}$alkylene. Representative alkylene groups include, by way of example, —$CH_2$—, —$(CH_2)_2$—, —$(CH_2)_3$—, —$CH_2$—$CH(CH_3)$—, —$(CH_2)_4$—, —$CH_2$—$CH(CH_3)$—$CH_2$—, —$(CH_2)_5$—, —$CH_2$—$CH(CH_3)$—$CH_2$—$CH_2$—, and the like. It is understood that when the alkylene term include zero carbons such as —$C_{0-1}$alkylene-, such terms are intended to include the absence of carbon atoms, that is, the alkylene group is not present except for a covalent bond attaching the groups separated by the alkylene term.

The term "aryl" means a monovalent aromatic hydrocarbon having a single ring (i.e., phenyl) or one or more fused rings. Fused ring systems include those that are fully unsaturated (e.g., naphthalene) as well as those that are partially unsaturated (e.g., 1,2,3,4-tetrahydronaphthalene). Unless otherwise defined, such aryl groups typically contain from 6 to 10 carbon ring atoms and include, for example, $C_{6-10}$aryl. Representative aryl groups include, by way of example, phenyl and naphthalene-1-yl, naphthalene-2-yl, and the like.

The term "cycloalkyl" means a monovalent saturated carbocyclic hydrocarbon group. Unless otherwise defined, such cycloalkyl groups typically contain from 3 to 10 carbon atoms and include, for example, $C_{3-5}$cycloalkyl, $C_{3-6}$cycloalkyl, $C_{3-7}$cycloalkyl, and $C_{5-6}$cycloalkyl. Representative cycloalkyl groups include, by way of example, cyclopropyl, cyclobutyl, cyclopentyl, cyclohexyl and the like.

The term "halo" means fluoro, chloro, bromo and iodo.

The term "heteroaryl" is intended to mean a monovalent unsaturated (aromatic) heterocycle having a single ring or two fused rings. Monovalent unsaturated heterocycles are also commonly referred to as "heteroaryl" groups. Unless otherwise defined, heteroaryl groups typically contain from 5 to 10 total ring atoms, of which 1 to 9 are ring carbon atoms, and 1 to 4 are ring heteroatoms, and include, for example, $C_{1-9}$heteroaryl and $C_{5-9}$heteroaryl. Representative heteroaryl groups include, by way of example, pyrrole (e.g., 1H-pyrrole, 2H-pyrrole, and 3H-pyrrole), imidazole (e.g., 2-imidazole), furan (e.g., 2-furan and 3-furan), thiophene (e.g., 2-thiophene), triazole (e.g., 1,2,3-triazole and 1,2,4-triazole), pyrazole (e.g., 1H-pyrazole and 4H-pyrazole), oxazole (e.g., 2-oxazole), isoxazole (e.g., 3-isoxazole), thiazole (e.g., 2-thiazole and 4-thiazole), and isothiazole (e.g., 3-isothiazole), pyridine (e.g., 2-pyridine, 3-pyridine, and 4-pyridine), pyridylimidazole, pyridyltriazole, pyrazine, pyridazine (e.g., 3-pyridazine), pyrimidine (e.g., 2-pyrimidine), tetrazole, triazine (e.g., 1,3,5-triazine), indole (e.g., 1H-indole), benzofuran, benzothiophene (e.g., benzo[b]thiophene), benzimidazole, benzoxazole, benzothiazole, benzotriazole, quinoline (e.g., 2-quinoline), isoquinoline, quinazoline, quinoxaline and the like.

The term "optionally substituted" means that group in question may be unsubstituted or it may be substituted one or several times, such as 1 to 3 times, or 1 to 5 times, or 1 to 8 times. For example, an alkyl group that is "optionally substituted" with fluoro atoms may be unsubstituted, or it may contain 1, 2, 3, 4, 5, 6, 7, or 8 fluoro atoms. Similarly, a group that is "optionally substituted" with one or two $C_{1-6}$alkyl groups, may be unsubstituted, or it may contain one or two $C_{1-6}$alkyl groups.

As used herein, the phrase "having the formula" or "having the structure" is not intended to be limiting and is used in the same way that the term "comprising" is commonly used. For example, if one structure is depicted, it is understood that all stereoisomer and tautomer forms are encompassed, unless stated otherwise.

The term "pharmaceutically acceptable" refers to a material that is not biologically or otherwise unacceptable when used in the invention. For example, the term "pharmaceutically acceptable carrier" refers to a material that can be incorporated into a composition and administered to a patient without causing unacceptable biological effects or interacting in an unacceptable manner with other components of the composition. Such pharmaceutically acceptable materials typically have met the required standards of toxicological and manufacturing testing, and include those materials identified as suitable inactive ingredients by the U.S. Food and Drug administration.

The term "pharmaceutically acceptable salt" means a salt prepared from a base or an acid which is acceptable for administration to a patient, such as a mammal (for example, salts having acceptable mammalian safety for a given dosage regime). However, it is understood that the salts covered by the invention are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a compound of formula I contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (for example, citric, gluconic, glycolic, lactic, lactobionic, malic, and tartaric acids), aliphatic monocarboxylic acids (for example, acetic, butyric, formic, propionic and trifluoroacetic acids), amino acids (for example, aspartic and glutamic acids), aromatic carboxylic acids (for example, benzoic, p-chlorobenzoic, diphenylacetic, gentisic, hippuric, and triphenylacetic acids), aromatic hydroxyl acids (for example, o-hydroxybenzoic, p-hydroxybenzoic, 1-hydroxynaphthalene-2-carboxylic and 3-hydroxynaphthalene-2-carboxylic acids), ascorbic, dicarboxylic acids (for example, fumaric, maleic, oxalic and succinic acids), glucoronic, mandelic, mucic, nicotinic, orotic, pamoic, pantothenic, sulfonic acids (for example, benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like.

As used herein, the term "prodrug" is generally intended to mean an inactive precursor of a drug that is converted into its active form in the body under physiological conditions, for example, by normal metabolic processes. Such compounds may not possess pharmacological activity at NEP, but may be administered orally or parenterally and thereafter metabolized in the body to form compounds that are pharmacologically active at NEP. When orally administered, such compounds may also provide a better fraction absorbed (i.e., better pK properties) for renal delivery, as compared to oral administration of the active form. Exemplary prodrugs include esters such as $C_{1-6}$alkylesters and aryl-$C_{1-6}$alkylesters. In one embodiment, the active compound has a free carboxyl and the prodrug is an ester derivative thereof, i.e., the prodrug is an ester such as —$C(O)OCH_2CH_3$. Such ester prodrugs are then converted by solvolysis or under physiological conditions to be the free carboxyl compound. The term "prodrug" is also intended to include a less active precursor of a drug that is converted into a more active form in the body. For example, certain prodrugs may possess pharmacological activity at NEP, but not necessarily at the desired level; such compounds are converted in the body into a form having the desired level of activity. The term is also intended to include certain protected derivatives of compounds of formula I that may be made prior to a final deprotection stage. Thus, all protected derivatives and prodrugs of compounds formula I are included within the scope of the invention.

The term "therapeutically effective amount" means an amount sufficient to effect treatment when administered to a patient in need thereof, that is, the amount of drug needed to obtain the desired therapeutic effect. For example, a therapeutically effective amount for treating hypertension is an amount of compound needed to, for example, reduce, suppress, eliminate, or prevent the symptoms of hypertension, or to treat the underlying cause of hypertension. In one embodiment, a therapeutically effective amount is that amount of drug needed to reduce blood pressure or the amount of drug needed to maintain normal blood pressure. On the other hand, the term "effective amount" means an amount sufficient to obtain a desired result, which may not necessarily be a therapeutic result. For example, when studying a system comprising aNEP enzyme, an "effective amount" may be the amount needed to inhibit the enzyme.

The term "treating" or "treatment" as used herein means the treating or treatment of a disease or medical condition (such as hypertension) in a patient, such as a mammal (particularly a human) that includes one or more of the following: (a) preventing the disease or medical condition from occurring, i.e., preventing the reoccurrence of the disease or medical condition or prophylactic treatment of a patient that is pre-disposed to the disease or medical condition; (b) ameliorating the disease or medical condition, i.e., eliminating or causing regression of the disease or medical condition in a patient; (c) suppressing the disease or medical condition, i.e., slowing or arresting the development of the disease or medical condition in a patient; or (d) alleviating the symptoms of the disease or medical condition in a patient. For example, the term "treating hypertension" would include preventing hypertension from occurring, ameliorating hypertension, suppressing hypertension, and alleviating the symptoms of hypertension (for example, lowering blood pressure). The term "patient" is intended to include those mammals, such as humans, that are in need of treatment or disease prevention or that are presently being treated for disease prevention or treatment of a specific disease or medical condition, as well as test subjects in which compounds of the invention are being evaluated or being used in an assay, for example an animal model.

All other terms used herein are intended to have their ordinary meaning as understood by those of ordinary skill in the art to which they pertain.

In one aspect, the invention relates to compounds of formula I:

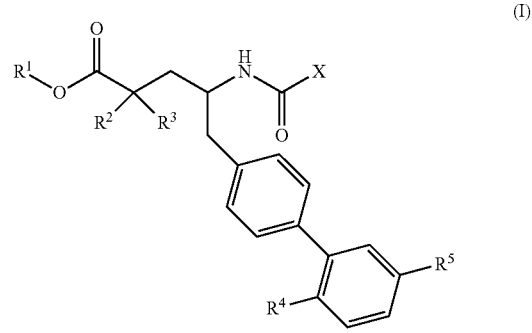

(I)

or a pharmaceutically acceptable salt thereof.

As used herein, the term "compound of the invention" includes all compounds encompassed by formula I such as the species embodied in formulas II-VII and a-f, and combinations thereof. In addition, the compounds of the invention may also contain several basic or acidic groups (for example, amino or carboxyl groups) and therefore, such compounds can exist as a free base, free acid, or in various salt forms. All such salt forms are included within the scope of the invention. Furthermore, the compounds of the invention may also exist as prodrugs. Accordingly, those skilled in the art will recognize that reference to a compound herein, for example, reference to a "compound of the invention" or a "compound of formula I" includes a compound of formula I as well as pharmaceutically acceptable salts and prodrugs of that compound unless otherwise indicated. Further, the term "or a pharmaceutically acceptable salt and/or prodrug thereof" is intended to include all permutations of salts and prodrugs, such as a pharmaceutically acceptable salt of a prodrug. Furthermore, solvates of compounds of formula I are included within the scope of this invention.

The compounds of formula I may contain one or more chiral centers and therefore, these compounds may be prepared and used in various stereoisomeric forms. Accordingly, the invention also relates to racemic mixtures, pure stereoisomers (e.g., enantiomers and diastereoisomers), stereoisomer-enriched mixtures, and the like unless otherwise indicated. When a chemical structure is depicted herein without any stereochemistry, it is understood that all possible stereoisomers are encompassed by such structure. Thus, for example, the terms "compounds of formula I," "compounds of formula Ia," and so forth, are intended to include all possible stereoisomers of the compound. Similarly, when a particular stereoisomer is shown or named herein, it will be understood by those skilled in the art that minor amounts of other stereoisomers may be present in the compositions of the invention unless otherwise indicated, provided that the utility of the composition as a whole is not eliminated by the presence of such other isomers. Individual stereoisomers may be obtained by numerous methods that are well known in the art, including chiral chromatography using a suitable chiral stationary phase or support, or by chemically converting them into diastereoisomers, separating the diastereoisomers by conventional means such as chromatography or recrystallization, then regenerating the original stereoisomer.

Additionally, where applicable, all cis-trans or E/Z isomers (geometric isomers), tautomeric forms and topoisomeric forms of the compounds of the invention are included within the scope of the invention unless otherwise specified.

More specifically, compounds of formula I can contain at least two chiral centers, which are indicated by the symbols * and ** in the following formula:

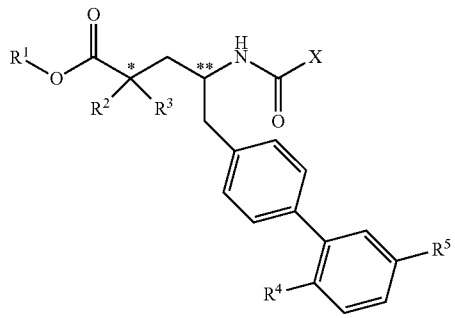

In one stereoisomer, both carbon atoms identified by the * and ** symbols have the (R) configuration. In this embodiment, compounds have the (R,R) configuration at the * and ** carbon atoms or are enriched in a stereoisomeric form having the (R,R) configuration at these carbon atoms:

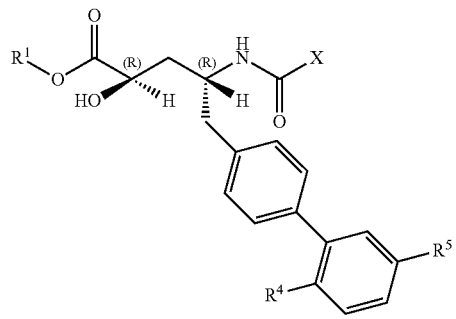

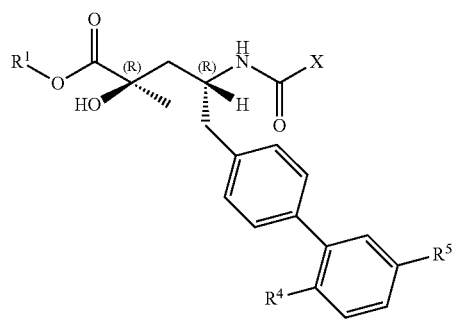

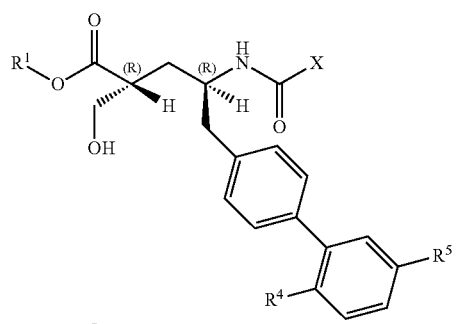

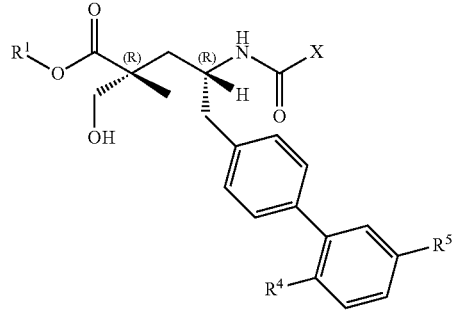

In another stereoisomer, both carbon atoms identified by the * and ** symbols have the (S) configuration. In this embodiment, compounds have the (S,S) configuration at the * and ** carbon atoms or are enriched in a stereoisomeric form having the (S,S) configuration at these carbon atoms:

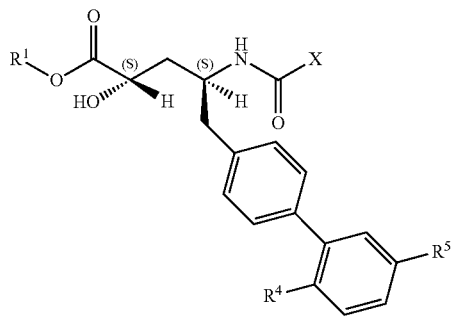
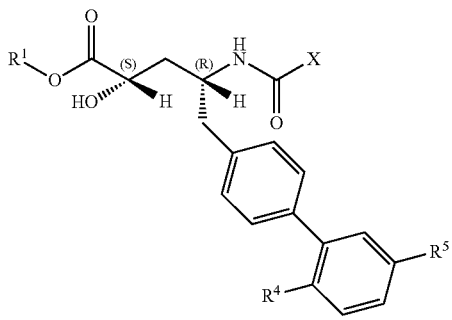

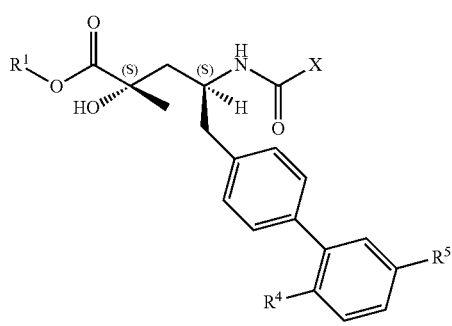
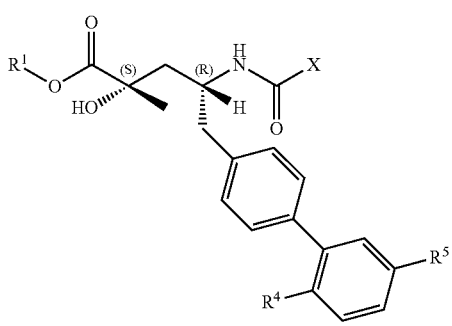

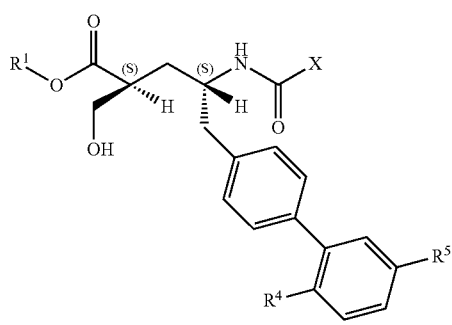
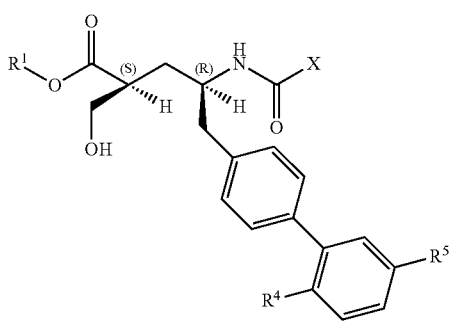

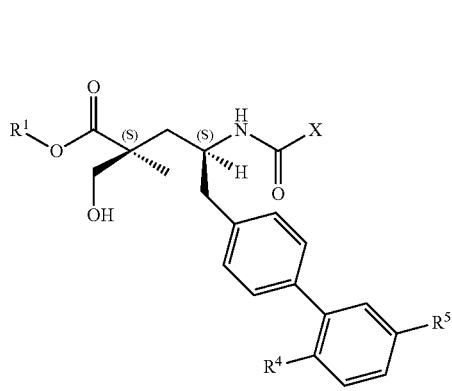
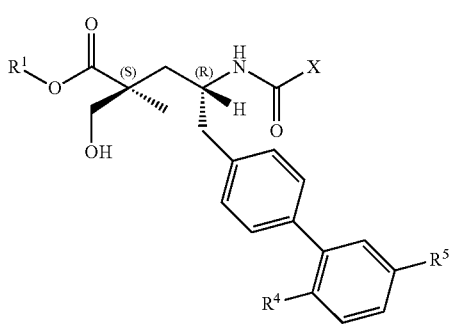

In yet another stereoisomer, the carbon atom identified by the symbol * has the (S) configuration and the carbon atom identified by the symbol ** has the (R) configuration. In this embodiment, compounds have the (S,R) configuration at the * and ** carbon atoms or are enriched in a stereoisomeric form having the (S,R) configuration at these carbon atoms:

In still another stereoisomer, the carbon atom identified by the symbol * has the (R) configuration and the carbon atom identified by the symbol ** has the (S) configuration. In this embodiment, compounds have the (R,S) configuration at the * and ** carbon atoms or are enriched in a stereoisomeric form having the (R,S) configuration at these carbon atoms:

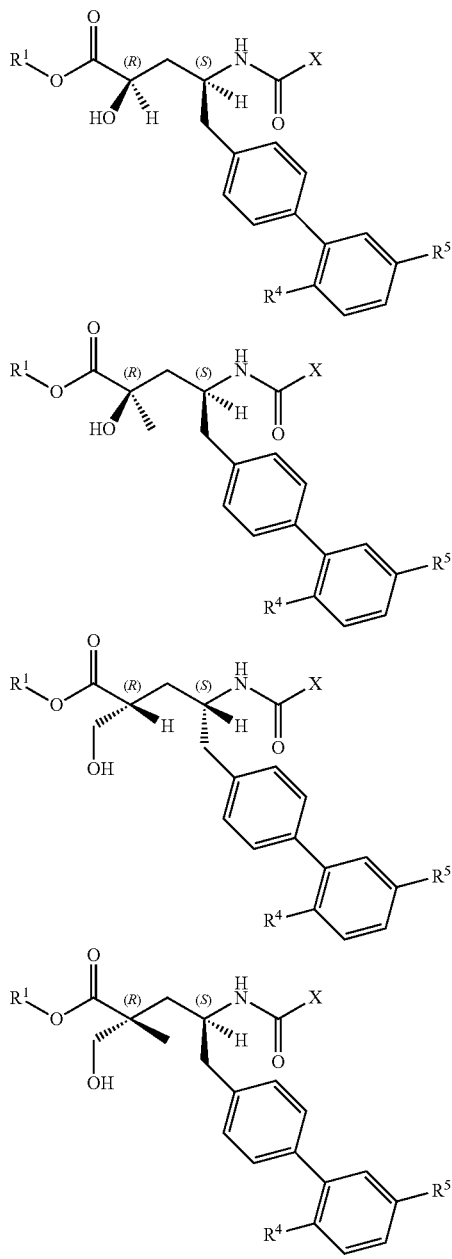

In some embodiments, in order to optimize the therapeutic activity of the compounds of the invention, e.g., to treat hypertension, it may be desirable that the carbon atoms identified the * and ** symbols have a particular configuration or are enriched in a stereoisomeric form having such configuration. Thus, in certain aspects, this invention relates to each individual enantiomer or to an enantiomer-enriched mixture of enantiomers comprising predominately one enantiomer or the other enantiomer. In other embodiments, the compounds of the invention are present as racemic mixtures of enantiomers.

The compounds of the invention, as well as those compounds used in their synthesis, may also include isotopically-labeled compounds, that is, where one or more atoms have been enriched with atoms having an atomic mass different from the atomic mass predominately found in nature. Examples of isotopes that may be incorporated into the compounds of formula I, for example, include, but are not limited to, $^2H$, $^3H$, $^{13}C$, $^{14}C$, $^{15}N$, $^{18}O$, $^{17}O$, $^{35}S$, $^{36}Cl$, and $^{18}F$. Of particular interest are compounds of formula I enriched in tritium or carbon-14 which can be used, for example, in tissue distribution studies; compounds of formula I enriched in deuterium especially at a site of metabolism resulting, for example, in compounds having greater metabolic stability; and compounds of formula I enriched in a positron emitting isotope, such as $^{11}C$, $^{18}F$, $^{15}O$ and $^{13}N$, which can be used, for example, in Positron Emission Topography (PET) studies.

The nomenclature used herein to name the compounds of the invention is illustrated in the Examples herein. This nomenclature has been derived using the commercially available AutoNom software (MDL, San Leandro, Calif.).

Representative Embodiments

The following substituents and values are intended to provide representative examples of various aspects and embodiments of the invention. These representative values are intended to further define and illustrate such aspects and embodiments and are not intended to exclude other embodiments or to limit the scope of the invention. In this regard, the representation that a particular value or substituent is preferred is not intended in any way to exclude other values or substituents from the invention unless specifically indicated.

In one aspect, this invention relates to compounds of formula I:

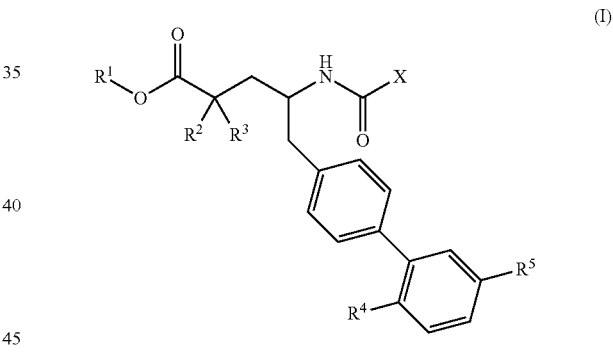

(I)

The $R^1$ moiety is selected from:
H;
$C_{1-8}$alkyl optionally substituted with one or more fluoro atoms, e.g., —$CH_3$, —$CH_2CH_3$, —$CH_2CF_3$, —$(CH_2)_2CH_3$, —$(CH_2)_2CF_3$, —$CH_2CF_2CH_3$, —$CH_2CF_2CF_3$, —$CH(CH_3)_2$, —$C(CH_3)_3$, —$C(CH_3)(CF_3)_2$, —$CH_2CH(CH_3)_2$, —$(CH_2)_3CH_3$, —$CH(CH_2CH_3)CF_3$, —$CH(CH_3)CF_2CF_3$, —$(CH_2)_4CH_3$, —$(CH_2)_2CH(CH_3)_2$, —$(CH_2)_5CH_3$, and —$(CH_2)_6CH_3$;
$C_{1-3}$alkylene-$C_{6-10}$aryl, e.g., benzyl;
$C_{1-3}$alkylene-$C_{1-9}$heteroaryl, e.g., —$CH_2$-pyridine and —$(CH_2)_2$-pyridine;
$C_{3-7}$cycloalkyl, e.g., cyclopentyl;
$C_{2-3}$alkylene-OH;
—$[(CH_2)_2O]_{1-3}CH_3$, e.g., —$(CH_2)_2OCH_3$ and —$[(CH_2)_2O]_2CH_3$;
$C_{1-6}$alkylene-OC(O)$R^{20}$, e.g., —$CH_2OC(O)CH_3$, —$CH_2OC(O)CH_2CH_3$, —$CH_2OC(O)(CH_2)_2CH_3$, —$CH_2CH(CH_3)OC(O)CH_2CH_3$, —$CH_2OC(O)OCH_3$, —$CH_2OC(O)OCH_2CH_3$, —$CH(CH_3)OC(O)OCH_2CH_3$, —$CH(CH_3)OC(O)O$—$CH(CH_3)_2$, —$CH_2CH(CH_3)OC(O)$- cyclopentyl, —CH$_2$OC(O)O-cyclopropyl, —CH(CH$_3$)—OC(O)—O— cyclohexyl, —CH$_2$OC(O)O-cyclopentyl, —CH$_2$CH(CH$_3$)OC(O)-phenyl, —CH$_2$OC(O)O— phenyl, —CH$_2$OC(O)—CH[CH(CH$_3$)$_2$]—NH$_2$, —CH$_2$OC(O)—CH[CH(CH$_3$)$_2$]—NHC(O)OCH$_3$, and —CH(CH$_3$)OC(O)—CH(NH$_2$)CH$_2$COOCH$_3$;

C$_{1-6}$alkylene-NR$^{21}$R$^{22}$, e.g., —(CH$_2$)$_2$—N(CH$_3$)$_2$, —(CH$_2$)$_3$—N(CH$_3$)$_2$, —(CH$_2$)$_4$—N(CH$_3$)$_2$,

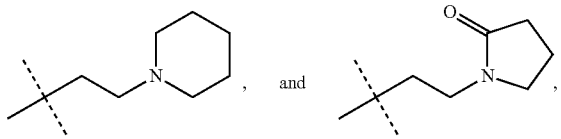
and

—CH$_2$CH(NH$_2$)COOCH$_3$;
C$_{1-6}$alkylene-C(O)R$^{23}$, e.g., —CH$_2$C(O)OCH$_3$, —CH$_2$C(O)O-benzyl, —CH$_2$C(O)—N(CH$_3$)$_2$, and

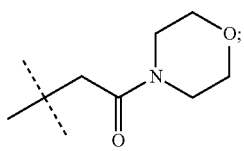

C$_{0-6}$alkylenemorpholine, e.g., —(CH$_2$)$_2$-morpholine and —(CH$_2$)$_3$-morpholine:

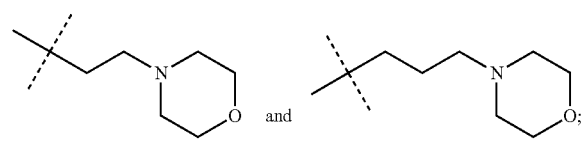

C$_{1-6}$alkylene-SO$_2$—C$_{1-6}$alkyl, e.g., —(CH$_2$)$_2$SO$_2$CH$_3$;

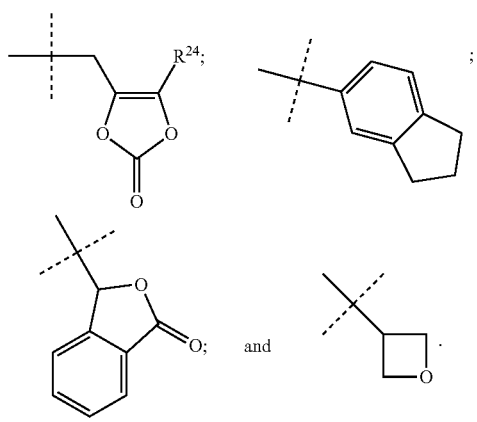

The R$^{20}$ moiety is selected from:
C$_{1-6}$alkyl, e.g., —CH$_3$ and —CH$_2$CH$_3$;
—O—C$_{1-6}$alkyl, e.g., —OCH$_3$, —O—CH$_2$CH$_3$, and —O—CH(CH$_3$)$_2$;
C$_{3-7}$cycloalkyl, e.g., cyclopentyl);
—O—C$_{3-7}$cycloalkyl, e.g., —O-cyclopropyl, —O-cyclohexyl, and —O-cyclopentyl;
phenyl;

—O-phenyl;
—NR$^{21}$R$^{22}$;
—CH(R$^{25}$)—NH$_2$, e.g., —CH[CH(CH$_3$)$_2$]—NH$_2$;
—CH(R$^{25}$)—NHC(O)O—C$_{1-6}$alkyl, e.g., —CH[CH(CH$_3$)$_2$]—NHC(O)OCH$_3$; and
—CH(NH$_2$)CH$_2$COOCH$_3$.

The R$^{21}$ and R$^{22}$ moieties are independently selected from H, —C$_{1-6}$alkyl (e.g., —CH$_3$), and benzyl. Alternately, the R$^{21}$ and R$^{22}$ moieties can be taken together as —(CH$_2$)$_{3-6}$—, —C(O)—(CH$_2$)$_3$—, or —(CH$_2$)$_2$O(CH$_2$)$_2$—, for example to form a group such as:

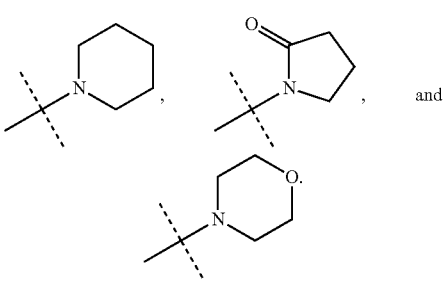

The R$^{23}$ moiety is selected from —O—C$_{1-6}$alkyl (e.g., —OCH$_3$), —O-benzyl, and —NR$^{21}$R$^{22}$ (e.g., —N(CH$_3$)$_2$). The R$^{24}$ moiety is C$_{1-6}$alkyl (e.g., —CH$_3$ and —C(CH$_3$)$_3$) or C$_{0-6}$alkylene-C$_{6-10}$aryl. The R$^{25}$ moiety is H, —CH$_3$, —CH(CH$_3$)$_2$, phenyl, or benzyl.

In one embodiment, R$^1$ is H. In other embodiments these compounds have formulas II-VII and a-f.

In another embodiment, R$^1$ is selected from C$_{1-8}$alkyl optionally substituted with one or more fluoro atoms; C$_{1-3}$alkylene-C$_{6-10}$aryl; C$_{1-3}$alkylene-C$_{1-9}$heteroaryl; C$_{3-7}$cycloalkyl; C$_{2-3}$alkylene-OH; —[(CH$_2$)$_2$O]$_{1-3}$CH$_3$; C$_{1-6}$alkylene-OC(O)R$^{20}$; C$_{1-6}$alkylene-NR$^{21}$R$^{22}$; —CH$_2$CH(NH$_2$)—COOCH$_3$; C$_{1-6}$alkylene-C(O)R$^{23}$; C$_{0-6}$alkylenemorpholine; C$_{1-6}$alkylene-SO$_2$—C$_{1-6}$alkyl;

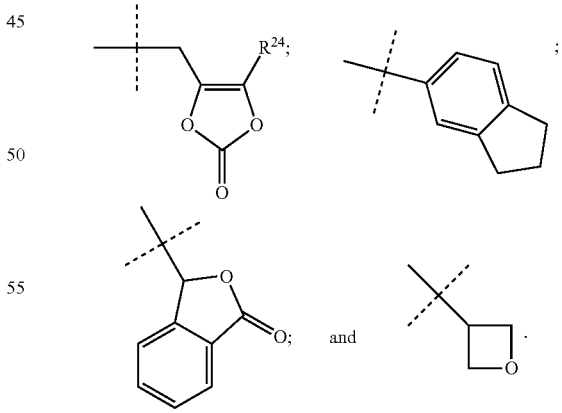

In other embodiments these compounds have formulas II-VII and a-f. In one aspect of the invention, these compounds may find particular utility as prodrugs or as intermediates in the synthetic procedures described herein. Specific examples of such prodrug moieties include where R$^1$ is C$_{1-6}$alkylene-OC(O)R$^{20}$, such as —CH(CH$_3$)OC(O)—O-cyclohexyl:

R¹ = 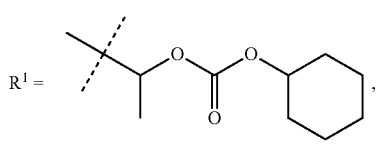, making the compound a cilexetil ester; or R¹ is $C_{0-6}$alkylenemorpholine such as —$(CH_2)_2$— morpholine:

R¹ = 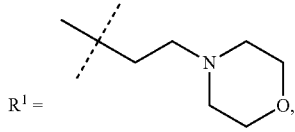, making the compound a 2-morpholinoethyl or mofetil ester; or

R¹ = 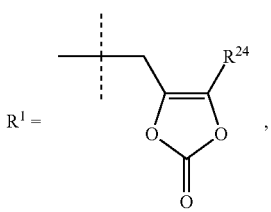, such as —$CH_2$-5-methyl-[1,3]dioxol-2-one:

R¹ = 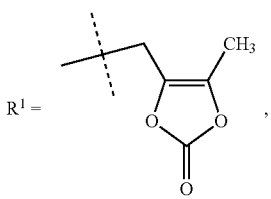, making the compound a medoxomil ester.

The R² group is —OH, —$CH_2OH$, or —$CH_2$—O—$C_{1-6}$ alkyl, and the R³ group is H or —$CH_3$. Thus, the compounds of the invention may have one of the following formulas:

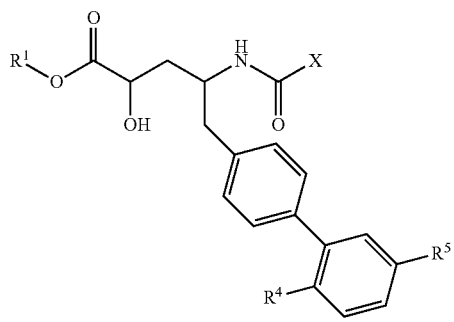 (II)

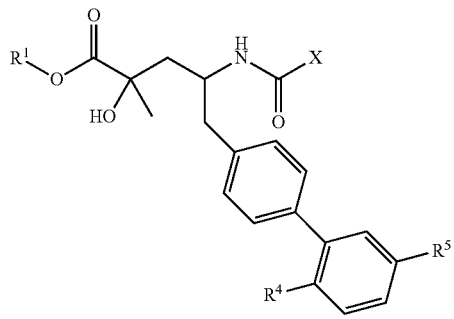 (III)

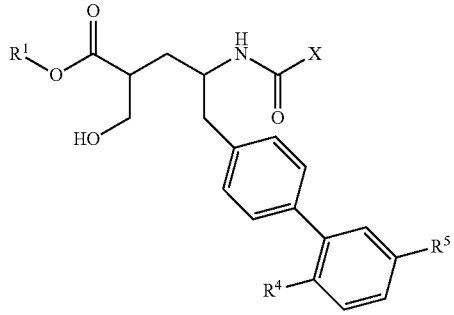 (IV)

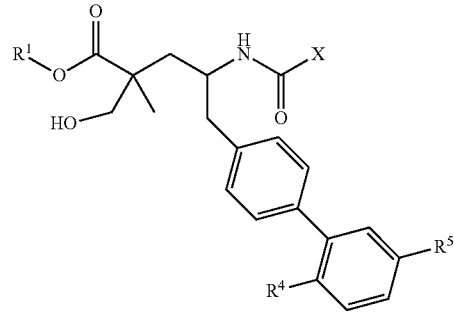 (V)

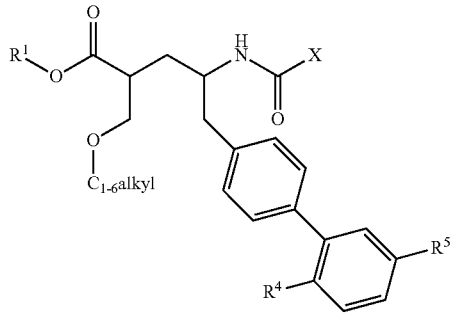 (VI)

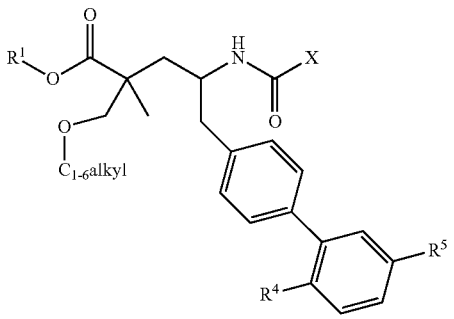 (VII)

The $R^4$ and $R^5$ groups are independently selected from hydrogen, halo (e.g., Cl and F), —OH, —CH$_3$, —OCH$_3$, —CN, and —CF$_3$. In one embodiment, $R^4$ is hydrogen or halo. In one embodiment, $R^5$ is halo. In another embodiment, $R^4$ is hydrogen and $R^5$ is halo; or $R^4$ is halo and $R^5$ is halo. In other embodiments these compounds have formulas II-VII and a-f.

The X group is selected from H, —C(O)—$R^6$, —C(O)—$NR^7R^8$, —C(O)—$NR^9$—$NR^{10}R^{11}$, —C(O)—$NR^{12}$—$NR^{13}$—C(O)—$R^{14}$, or —CH($R^{15}$)—$OR^{16}$. In one embodiment, X is —C(O)—$R^6$, which can be depicted as formula a:

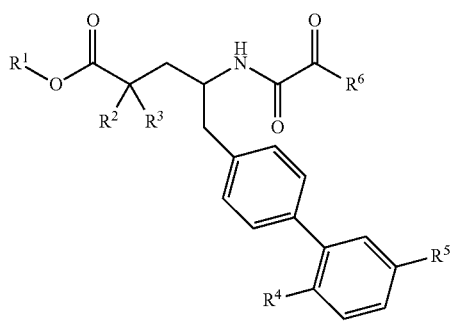

(a)

In the embodiment of formula a, the $R^6$ moiety is selected from C$_{1-6}$alkyl (e.g., —CH$_3$, —CH$_2$CH$_3$ and —CH$_2$CH(CH$_3$)$_2$), C$_{1-6}$alkylene-O—C$_{1-6}$alkyl, C$_{6-10}$aryl (e.g., phenyl), benzyl, and C$_{1-9}$heteroaryl (e.g., pyridine). In one embodiment, $R^6$ is C$_{1-6}$alkyl (e.g., —CH$_2$CH$_3$ or —CH$_2$CH(CH$_3$)$_2$) or benzyl. In other embodiments these compounds have formulas II-VII; and in one particular embodiment, formula II.

In one embodiment, X is —C(O)—$NR^7R^8$, which can be depicted as formula b:

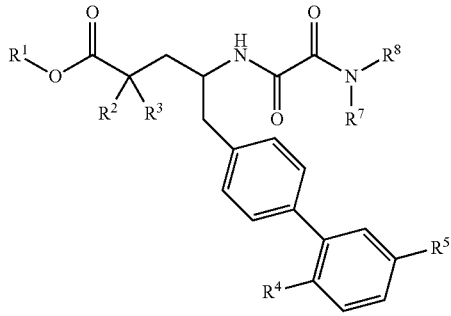

(b)

In the embodiment of formula b, the $R^7$ moiety is selected from H, —OH, or C$_{1-6}$alkyl (e.g., —CH$_3$). In one embodiment, $R^7$ is H, —OH, or —CH$_3$. In other embodiments these compounds have formulas II-VII; and in one particular embodiment, formula II.

The $R^8$ moiety is selected from: C$_{1-6}$alkyl; —O—C$_{1-6}$alkyl; C$_{5-6}$cycloalkyl; C$_{6-10}$aryl; —O—C$_{6-10}$aryl (e.g., —O-phenyl); —O-benzyl; pyridine optionally substituted with halo, —OH, C$_{1-6}$alkyl, or —O—C$_{1-6}$alkyl; morpholine; and isoxazolidinone, for example, isoxazolidin-3-one:

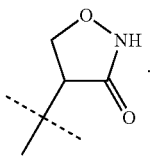

In one embodiment, $R^8$ is C$_{1-6}$alkyl (e.g., —CH$_3$), —O—C$_{1-6}$ alkyl (e.g., —O—CH$_3$), C$_{5-6}$cycloalkyl (e.g., cyclopentyl), phenyl, —O-benzyl, pyridine, pyridine substituted with halo (e.g., Br), pyridine substituted with C$_{1-6}$alkyl (e.g., —CH$_3$), morpholine, or isoxazolidinone. In other embodiments these compounds have formulas II-VII.

Alternately, the $R^7$ and $R^8$ groups can be taken together to form a ring selected from the group consisting of:

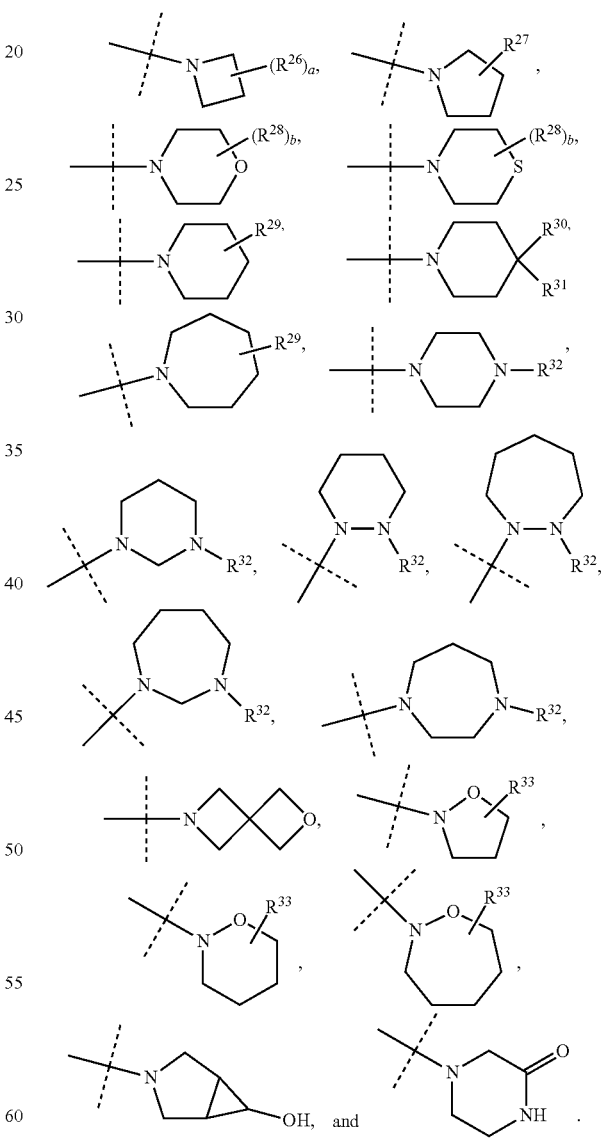

The "a" integer can be is 1 and $R^{26}$ is —OH. The "a" integer can be 2 and each $R^{26}$ is independently halo (e.g., F) or —C$_{1-3}$alkylene-OH. The $R^{27}$ moiety is —C$_{1-3}$alkylene-OH (e.g., —CH$_2$—OH), —C(O)NH$_2$, or —SO$_2$CH$_3$. The "b" integer is 0, or the "b" integer is 1 and $R^{28}$ is —C$_{1-3}$alkylene- OH (e.g., —CH$_2$—OH), or the "b" integer is 2 and each R$^{28}$ is C$_{1-6}$alkyl (e.g., —CH$_3$). The R$^{29}$ moiety is halo (e.g., fluoro), —COOH, —OH, —C$_{1-3}$alkylene-OH, —CH$_2$O—CH$_3$, —CONH$_2$, —CN, or pyridine. The R$^{30}$ moiety is C$_{1-6}$alkyl (e.g., —CH$_3$) or C$_{3-7}$cycloalkyl. The R$^{31}$ moiety is —OH or —C$_{1-3}$alkylene-OH. The R$^{32}$ moiety is halo, C$_{1-6}$alky (e.g., —CH$_3$); C$_{2-4}$alkylene-O—C$_{1-6}$alkyl (e.g., —(CH$_2$)$_2$OCH$_2$CH$_3$); —C(O)O—C$_{1-6}$alkyl (e.g., —C(O)OCH$_3$ and —C(O)OCH$_2$CH$_3$); —C(O)N(CH$_3$)$_2$; pyridine; —SO$_2$CH$_3$; —C(O)-furan; or phenyl substituted with halo, —O—C$_{1-6}$alkyl, or —CN. The R$^{33}$ moiety is H, —OH, —O—C$_{1-6}$alkyl or —O—C$_{6-10}$aryl. In other embodiments these compounds have formulas II-VII.

In one embodiment, R$^7$ and R$^8$ are taken together to form a ring selected from the group consisting of:

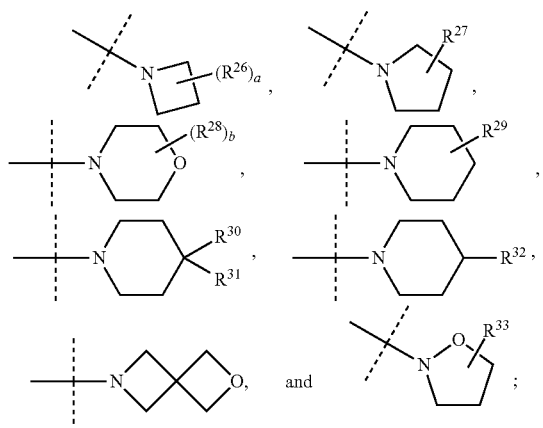

where a is 1 and R$^{26}$ is —OH, or a is 2 and each R$^{26}$ is halo; R$^{27}$ is —CH$_2$—OH, —C(O)NH$_2$, or —SO$_2$CH$_3$; b is 0, or b is 1 and R$^{28}$ is —CH$_2$—OH, or b is 2 and each R$^{28}$ is —CH$_3$; R$^{29}$ is fluoro, —COOH, —OH, —CH$_2$OH, —(CH$_2$)$_2$OH, —CH$_2$O—CH$_3$, —CONH$_2$, —CN, or pyridine; R$^{30}$ is —CH$_3$; R$^{31}$ is —OH; R$^{32}$ is —CH$_3$, —(CH$_2$)$_2$OCH$_2$CH$_3$, —C(O)OCH$_3$, —C(O)OCH$_2$CH$_3$, —C(O)N(CH$_3$)$_2$, —SO$_2$CH$_3$, —C(O)-furan, or phenyl substituted with —CN; and R$^{33}$ is H or —OH. In other embodiments these compounds have formulas II-VII.

In one embodiment, X is —C(O)—NR$^9$—NR$^{10}$R$^{11}$, which can be depicted as formula c:

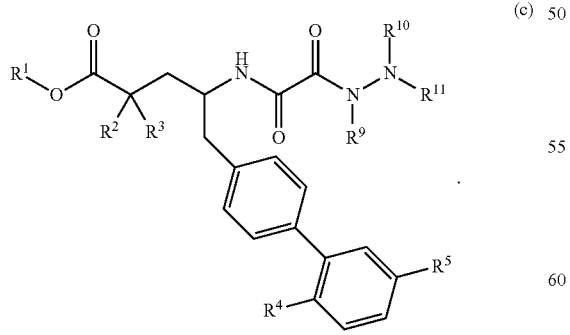

(c)

In the embodiment of formula c, the R$^9$ moiety is H or C$_{1-6}$alkyl; and in one embodiment, R$^9$ is H. The R$^{10}$ moiety is H or C$_{1-6}$alkyl; and in one embodiment, R$^{10}$ is H. The R$^{11}$ moiety is selected from C$_{1-6}$alkyl; C$_{1-9}$heteroaryl optionally substituted with halo, —OH, C$_{1-6}$alkyl (e.g., —CH$_3$), or —O—C$_{1-6}$alkyl (e.g., pyridine, pyridine substituted with —CH$_3$, pyrimidine, pyrimidine substituted with —OH, furan, thiophene, pyrazole, and pyrrole); dihydroimidazole; and phenyl optionally substituted with one or two groups selected from halo (e.g., Cl, F, Br), C$_{1-6}$alkyl (e.g., —CH$_3$), —O—C$_{1-6}$alkyl (e.g., —OCH$_3$), and —NO$_2$. Exemplary optionally substituted pyridine groups include 2-pyridyl, 3-pyridyl, and 4-pyridyl:

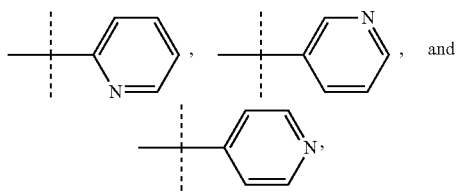

as well as 3-pyridine substituted with —CH$_3$:

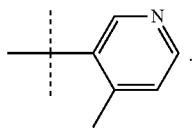

Exemplary pyrimidine groups substituted with —OH include:

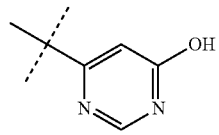

An exemplary dihydroimidazole group is 4,5-dihydro-1H-imidazole:

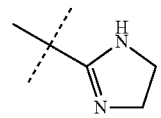

Exemplary optionally substituted phenyl groups include: phenyl, 2-chlorophenyl, 2-fluorophenyl, 3, chlorophenyl, 2-methylephenyl, 3-methylphenyl, 4-methylphenyl, 4-chlorophenyl, 4-fluorophenyl, 4-bromophenyl, 4-methoxyphenyl, and 2,4-dinitrophenyl. In one embodiment, R$^{11}$ is selected from C$_{1-6}$alkyl (e.g., —CH$_3$ or —CH$_2$CH(CH$_3$)$_2$); C$_{1-9}$heteroaryl optionally substituted with halo, —OH, C$_{1-6}$alkyl, or —O—C$_{1-6}$alkyl (e.g., pyridine or pyrimidine substituted with —OH; dihydroimidazole; and phenyl optionally substituted with one or two groups selected from halo (e.g., Cl, F, Br), C$_{1-6}$alkyl (e.g., —CH$_3$), —O—C$_{1-6}$alkyl (e.g., —OCH$_3$), and —NO$_2$. In other embodiments these compounds have formulas II-VII; and in one particular embodiment, formula II.

In one embodiment, X is —C(O)—NR$^{12}$—NR$^{13}$—C(O)—R$^{14}$, which can be depicted as formula d:

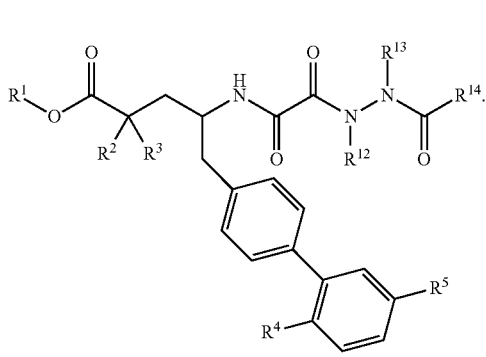

(d)

In the embodiment of formula d, the $R^{12}$ moiety is H or $C_{1-6}$alkyl; and in one embodiment, $R^{12}$ is H. The $R^{13}$ moiety is H or $C_{1-6}$alkyl; and in one embodiment, $R^{13}$ is H. The $R^{14}$ moiety is selected from —O-benzyl; pyridine optionally substituted with halo (e.g., Cl), —OH, $C_{1-6}$alkyl (e.g., —CH$_3$), or —O—$C_{1-6}$alkyl; furan; and phenyl substituted with halo, —OH, —O—$C_{1-6}$alkyl, or —NO$_2$. Exemplary halo-substituted pyridine groups include:

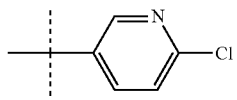

Exemplary substituted phenyl groups include: 2-hydroxyphenyl and 2-nitrophenyl. In one embodiment, $R^{14}$ is selected from —O-benzyl; pyridine; pyridine substituted with halo; furan; and phenyl substituted with —OH or —NO$_2$. In other embodiments these compounds have formulas II-VII; and in one particular embodiment, formula II.

In one embodiment, X is —CH($R^{15}$)—O$R^{16}$, which can be depicted as formula e:

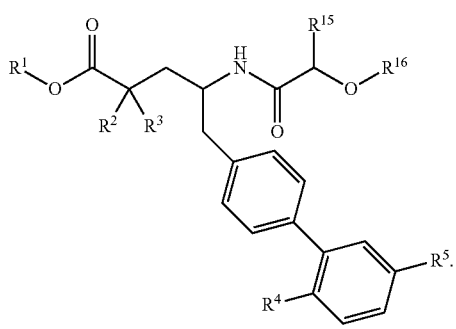

(e)

As noted above, the $R^{15}$ moiety is selected from H and $C_{1-6}$alkyl; and in one particular embodiment of formula (e), $R^{15}$ is H. The $R^{16}$ moiety is selected from H, $C_{1-6}$alkyl, —[(CH$_2$)$_2$O]$_{1-3}$CH$_3$, $C_{1-9}$heteroaryl (e.g., pyridine such as 3-pyridine), benzyl, and $C_{6-10}$aryl (e.g., phenyl) optionally substituted with —OH or —OCH$_3$. Alternately, the $R^{15}$ and $R^{16}$ groups can be taken together to form —(CH$_2$)$_4$—, i.e., $R^{15}$ and $R^{16}$ are taken together to form:

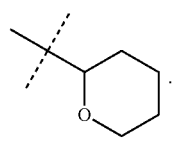

In one embodiment of formula (e), $R^{16}$ is selected from H, —CH$_3$, —CH(CH$_3$)$_2$, —CH$_2$CH$_3$, pyridine, benzyl, phenyl, phenyl substituted with —OH, and phenyl substituted with —OCH$_3$; or $R^{15}$ and $R^{16}$ are taken together to form —(CH$_2$)$_4$—. In other embodiments these compounds have formulas II-VII; and in one particular embodiment, formula II or V.

In another embodiment, X is H, which can be depicted as formula f:

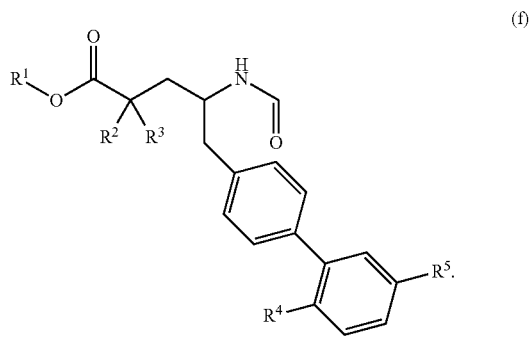

(f)

In other embodiments these compounds have formulas II-VII; and in one particular embodiment, formula V.

In addition, particular compounds of formula I that are of interest include those set forth in the Examples below, as well as pharmaceutically acceptable salts thereof.

General Synthetic Procedures

Compounds of the invention can be prepared from readily available starting materials using the following general methods, the procedures set forth in the Examples, or by using other methods, reagents, and starting materials that are known to those of ordinary skill in the art. Although the following procedures may illustrate a particular embodiment of the invention, it is understood that other embodiments of the invention can be similarly prepared using the same or similar methods or by using other methods, reagents and starting materials known to those of ordinary skill in the art. It will also be appreciated that where typical or preferred process conditions (for example, reaction temperatures, times, mole ratios of reactants, solvents, pressures, etc.) are given, other process conditions can also be used unless otherwise stated. In some instances, reactions were conducted at room temperature and no actual temperature measurement was taken. It is understood that room temperature can be taken to mean a temperature within the range commonly associated with the ambient temperature in a laboratory environment, and will typically be in the range of about 18° C. to about 30° C. In other instances, reactions were conducted at room temperature and the temperature was actually measured and recorded. While optimum reaction conditions will typically vary depending on various reaction parameters such as the particular reactants, solvents and quantities used, those of ordinary skill in the art can readily determine suitable reaction conditions using routine optimization procedures.

Additionally, as will be apparent to those skilled in the art, conventional protecting groups may be necessary or desired to prevent certain functional groups from undergoing undesired reactions. The choice of a suitable protecting group for a particular functional group as well as suitable conditions and reagents for protection and deprotection of such functional groups are well-known in the art. Protecting groups other than those illustrated in the procedures described herein may be used, if desired. For example, numerous protecting groups, and their introduction and removal, are described in T. W. Greene and G. M. Wuts, *Protecting Groups in Organic Synthesis*, Fourth Edition, Wiley, New York, 2006, and references cited therein.

Carboxy protecting groups are suitable for preventing undesired reactions at a carboxy group, and examples include, but are not limited to, methyl, ethyl, t-butyl, benzyl (Bn), p-methoxybenzyl (PMB), 9-fluorenylmethyl (Fm), trimethylsilyl (TMS), t-butyldimethylsilyl (TBDMS), diphenylmethyl (benzhydryl, DPM) and the like. Amino protecting groups are suitable for preventing undesired reactions at an amino group, and examples include, but are not limited to, t-butoxycarbonyl (BOC), trityl (Tr), benzyloxycarbonyl (Cbz), 9-fluorenylmethoxycarbonyl (Fmoc), formyl, trimethylsilyl (TMS), t-butyldimethylsilyl (TBDMS), and the like.

Standard deprotection techniques and reagents are used to remove the protecting groups, and may vary depending upon which group is used. For example, sodium or lithium hydroxide is commonly used when the carboxy-protecting group is methyl, an acid such as TFA or HCl is commonly used when the carboxy-protecting group is ethyl or t-butyl, and $H_2$/Pd/C may be used when the carboxy-protecting group is benzyl. A BOC amino-protecting group can be removed using an acidic reagent such as TFA in DCM or HCl in 1,4-dioxane, while a Cbz amino-protecting group can be removed by employing catalytic hydrogenation conditions such as $H_2$ (1 atm) and 10% Pd/C in an alcoholic solvent ("$H_2$/Pd/C").

Suitable bases for use in these schemes include, by way of illustration and not limitation, potassium carbonate, calcium carbonate, sodium carbonate, triethylamine, pyridine, 1,8-diazabicyclo-[5.4.0]undec-7-ene (DBU), N,N-diisopropylethylamine (DIPEA), 4-methylmorpholine, sodium hydroxide, potassium hydroxide, potassium t-butoxide, and metal hydrides.

Suitable inert diluents or solvents for use in these schemes include, by way of illustration and not limitation, tetrahydrofuran (THF), acetonitrile (MeCN), N,N-dimethylformamide (DMF), N,N-dimethylacetamide (DMA), dimethyl sulfoxide (DMSO), toluene, dichloromethane (DCM), chloroform ($CHCl_3$), carbon tetrachloride ($CCl_4$), 1,4-dioxane, methanol, ethanol, water, and the like.

Suitable carboxylic acid/amine coupling reagents include benzotriazol-1-yloxytris(dimethylamino)phosphonium hexafluorophosphate (BOP), benzotriazol-1-yloxytripyrrolidinophosphonium hexafluorophosphate (PyBOP), N,N,N',N'-tetramethyl-O-(7-azabenzotriazol-1-yl)uronium hexafluorophosphate (HATU), (2-(6-chloro-1H-benzotriazole-1-yl)-1,1,3,3-tetramethylaminium hexafluorophosphate) (HCTU), 1,3-dicyclohexylcarbodiimide (DCC), N-(3-dimethylaminopropyl)-N'-ethylcarbodiimide (EDCI), carbonyldiimidazole (CDI), 1-hydroxybenzotriazole (HOBt), and the like. Coupling reactions are conducted in an inert diluent in the presence of a base such as DIPEA, and are performed under conventional amide bond-forming conditions.

All reactions are typically conducted at a temperature within the range of about −78 C to 100° C., for example at room temperature. Reactions may be monitored by use of thin layer chromatography (TLC), high performance liquid chromatography (HPLC), and/or LCMS until completion. Reactions may be complete in minutes, or may take hours, typically from 1-2 hours and up to 48 hours. Upon completion, the resulting mixture or reaction product may be further treated in order to obtain the desired product. For example, the resulting mixture or reaction product may be subjected to one or more of the following procedures: concentrating or partitioning (for example, between EtOAc and water or between 5% THF in EtOAc and 1M phosphoric acid); extraction (for example, with EtOAc, $CHCl_3$, DCM, chloroform); washing (for example, with saturated aqueous NaCl, saturated aqueous $NaHCO_3$, $Na_2CO_3$ (5%), $CHCl_3$ or 1M NaOH); drying (for example, over $MgSO_4$, over $Na_2SO_4$, or in vacuo); filtering; crystallizing (for example, from EtOAc and hexanes); being concentrated (for example, in vacuo); and/or purification (e.g., silica gel chromatography, flash chromatography, preparative HPLC, reverse phase-HPLC, or crystallization).

Compounds of formula a, as well as their salts, can be prepared as shown in Scheme A:

Scheme A

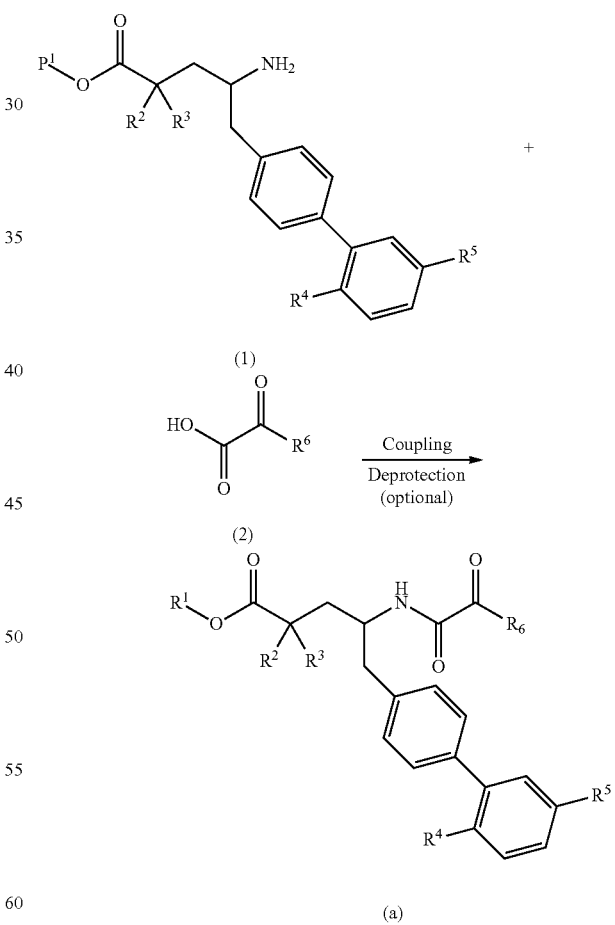

The process comprises the step of coupling compound 1 with compound 2, where $R^2$, $R^3$, $R^4$, $R^5$, and $R^6$ are as defined for formula I, and $P^1$ is H or a suitable carboxy protecting group, examples of which include, by way of illustration and not limitation, methyl, ethyl, t-butyl, benzyl, p-methoxybenzyl, 9-fluorenylmethyl, trimethylsilyl, t-butyldimethylsilyl, and diphenylmethyl. When $P^1$ is a carboxy protecting group, the process further comprises removal of the $P^1$ group by deprotection, in situ, with or after the coupling step. Methods of preparing compound 1 are described in the Examples. Compound 2 is generally commercially available or can be prepared using procedures that are known in the art.

Compounds of formula b, as well as their salts, can be prepared as shown in Scheme B:

Scheme B

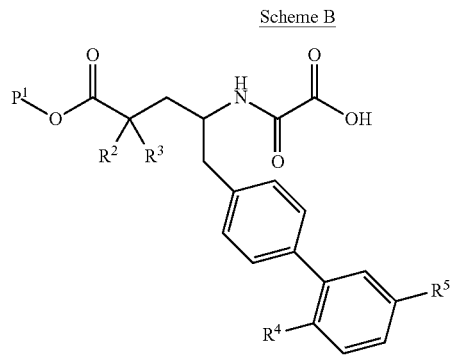

(3)

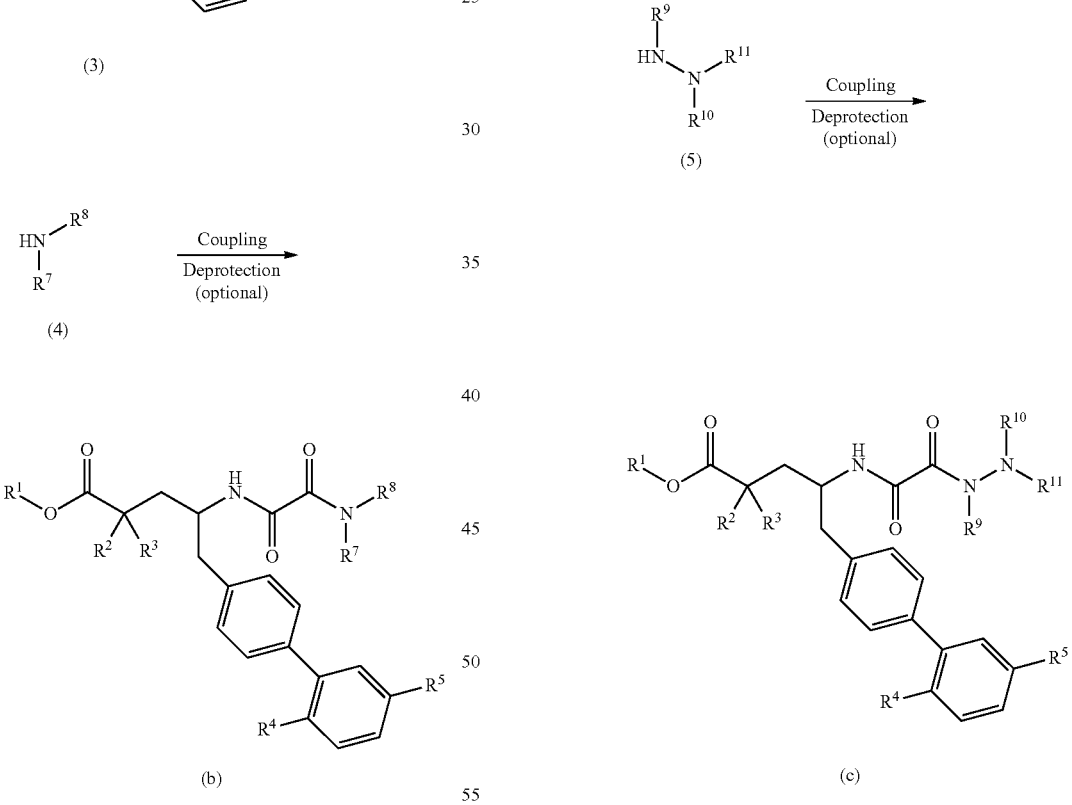

Scheme C

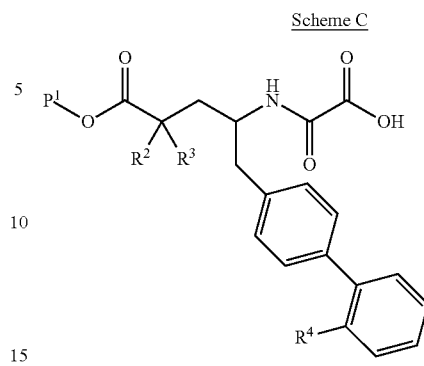

(3)

The process comprises the step of coupling compound 3 with compound 4, where $R^2$, $R^3$, $R^4$, $R^5$, $R^7$, and $R^8$ are as defined for formula I, and $P^1$ is H or a suitable carboxy protecting group. The process may further comprises removal of the $P^1$ group by deprotection, in situ, with or after the coupling step. Methods of preparing compound 3 are described in the Examples. Compound 4 is generally commercially available or can be prepared using procedures that are known in the art.

Compounds of formula c, as well as their salts, can be prepared as shown in Scheme C:

The process comprises the step of coupling compound 3 with compound 5, where $R^2$, $R^3$, $R^4$, $R^5$, $R^9$, $R^{10}$, and $R^{11}$ are as defined for formula I, and $P^1$ is H or a suitable carboxy protecting group. The process may further comprises removal of the $P^1$ group by deprotection, in situ, with or after the coupling step. Compound 5 is generally commercially available or can be prepared using procedures that are known in the art.

Compounds of formula d, as well as their salts, can be prepared as shown in Scheme D:

Scheme D

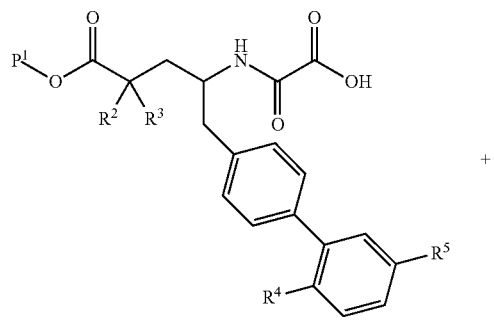

(3)

+

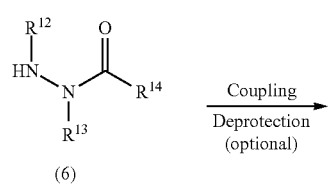

(6)

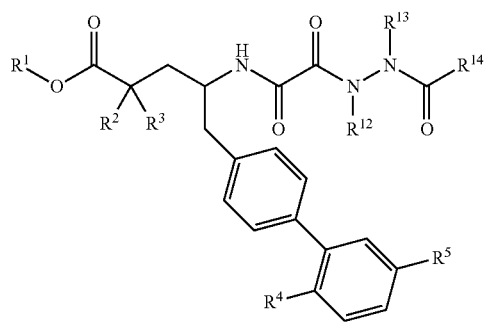

(d)

The process comprises the step of coupling compound 3 with compound 6, where $R^2$, $R^3$, $R^4$, $R^5$, $R^{12}$, $R^{13}$, and $R^{14}$ are as defined for formula I, and $P^1$ is H or a suitable carboxy protecting group. The process may further comprises removal of the $P^1$ group by deprotection, in situ, with or after the coupling step. Compound 6 is generally commercially available or can be prepared using procedures that are known in the art.

Compounds of formula e, as well as their salts, can be prepared as shown in Scheme E:

Scheme E

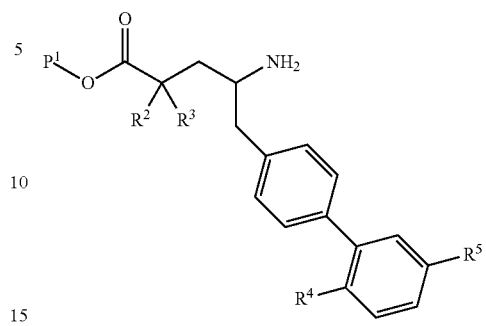

(1)

+

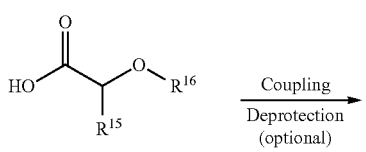

(7)

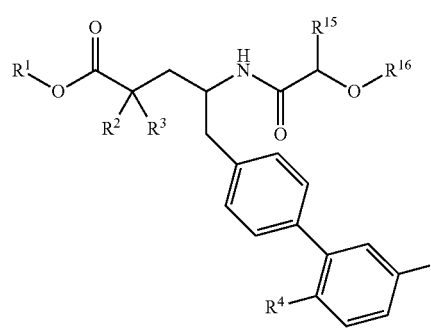

(e)

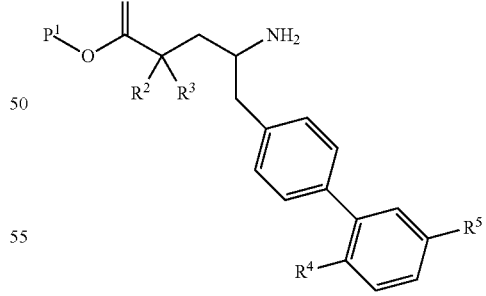

(1)

+

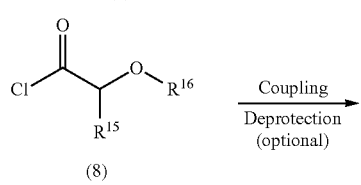

(8)

-continued

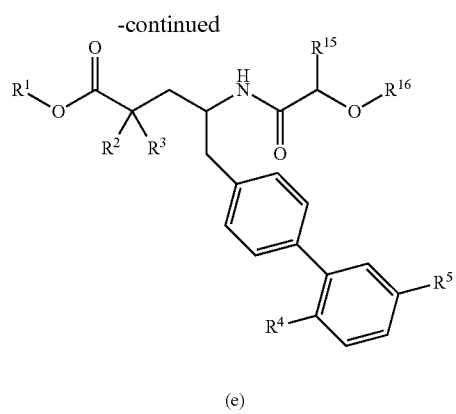

(e)

The process comprises the step of coupling compound 1 with compound 7 or compound 8, where $R^2$, $R^3$, $R^4$, $R^5$, $R^{15}$, and $R^{16}$ are as defined for formula I, and $P^1$ is H or a suitable carboxy protecting group. The process may further comprises removal of the $P^1$ group by deprotection, in situ, with or after the coupling step. Compound 8 is generally commercially available or can be prepared using procedures that are known in the art.

Compounds of formula f, as well as their salts, can be prepared as shown in Scheme F:

Scheme F

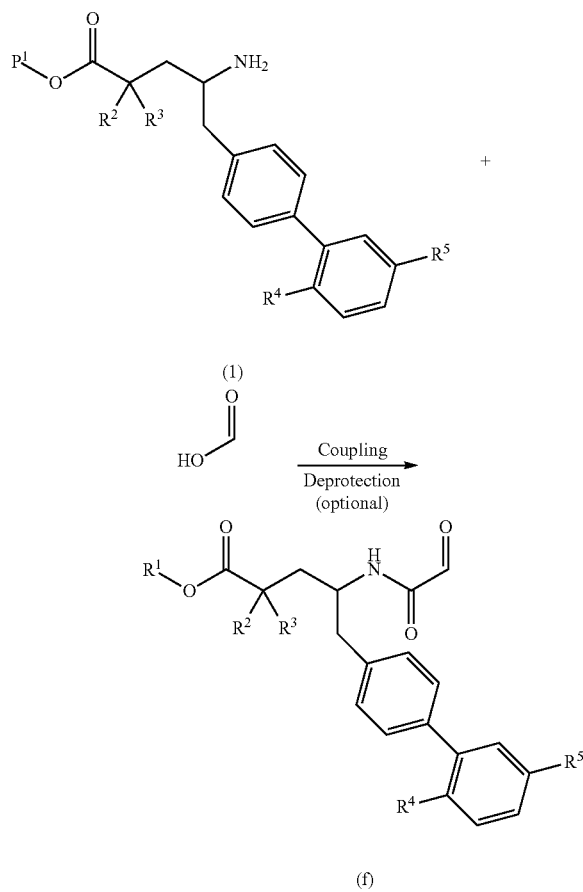

The process comprises the step of coupling compound 1 with formic acid, where $R^2$, $R^3$, $R^4$, and $R^5$, are as defined for formula I, and $P^1$ is H or a suitable carboxy protecting group. The process may further comprises removal of the $P^1$ group by deprotection, in situ, with or after the coupling step.

Further details regarding specific reaction conditions and other procedures for preparing representative compounds of the invention or intermediates thereof are described in the Examples set forth below.

Utility

Compounds of the invention possess neprilysin (NEP) inhibition activity, that is, the compounds are able to inhibit enzyme-catalytic activity. In another embodiment, the compounds do not exhibit significant inhibitory activity of the angiotensin-converting enzyme. One measure of the ability of a compound to inhibit NEP activity is the inhibition constant ($pK_i$). The $pK_i$ value is the negative logarithm to base 10 of the dissociation constant ($K_i$), which is typically reported in molar units. Compounds of the invention of particular interest are those having a $pK_i$ at NEP greater than or equal to 6.0, particularly those having a $pK_i$ greater than or equal to 7.0, and even more particularly those having a $pK_i$ greater than or equal to 8.0. In one embodiment, compounds of interest have a $pK_i$ in the range of 6.0-6.9; in another embodiment, compounds of interest have a $pK_i$ in the range of 7.0-7.9; in yet another embodiment, compounds of interest have a $pK_i$ in the range of 8.0-8.9; and in still another embodiment, compounds of interest have a $pK_i$ in the range of greater than or equal to 9.0. Such values can be determined by techniques that are well known in the art, as well as in the assays described herein.

Another measure of the ability of a compound to inhibit NEP activity is the apparent inhibition constant ($IC_{50}$), which is the molar concentration of compound that results in half-maximal inhibition of substrate conversion by the NEP enzyme. The $pIC_{50}$ value is the negative logarithm to base 10 of the $IC_{50}$. Compounds of the invention that are of particular interest, include those that exhibit a $pIC_{50}$ for NEP greater than or equal to about 5.0. Compounds of interest also include those having a $pIC_{50}$ for NEP≥about 6.0 or a $pIC_{50}$ for NEP≥about 7.0. In another embodiment, compounds of interest have a $pIC_{50}$ for NEP within the range of about 7.0-11.0; and in another embodiment, within the range of about 8.0-11.0, such as within the range of about 8.0-10.0.

It is noted that in some cases, compounds of the invention may possess weak NEP inhibition activity. In such cases, those of skill in the art will recognize that these compounds still have utility as research tools.

Exemplary assays to determine properties of compounds of the invention, such as the NEP inhibiting activity, are described in the Examples and include by way of illustration and not limitation, assays that measure NEP inhibition (described in Assay 1). Useful secondary assays include assays to measure ACE inhibition (also described in Assay 1) and aminopeptidase P (APP) inhibition (described in Sulpizio et al. (2005) *JPET* 315:1306-1313). A pharmacodynamic assay to assess the in vivo inhibitory potencies for ACE and NEP in anesthetized rats is described in Assay 2 (see also Seymour et al. (1985) *Hypertension* 7(Suppl I):I-35-I-42 and Wigle et al. (1992) *Can. J. Physiol. Pharmacol.* 70:1525-1528), where ACE inhibition is measured as the percent inhibition of the angiotensin I pressor response and NEP inhibition is measured as increased urinary cyclic guanosine 3', 5'-monophosphate (cGMP) output.

There are many in vivo assays that can be used to ascertain further utilities of the compounds of the invention.

The conscious spontaneously hypertensive rat (SHR) model is a renin dependent hypertension model, and is described in Assay 3. See also Intengan et al. (1999) *Circulation* 100 (22):2267-2275 and Badyal et al. (2003) *Indian Journal of Pharmacology* 35:349-362. The conscious desoxycorticosterone acetate-salt (DOCA-salt) rat model is a volume dependent hypertension model that is useful for measuring NEP activity, and is described in Assay 4. See also Trapani et al. (1989) *J Cardiovasc. Pharmacol.* 14:419-424, Intengan et al. (1999) *Hypertension* 34(4):907-913, and Badyal et al. (2003) supra). The DOCA-salt model is particularly useful for evaluating the ability of a test compound to reduce blood pressure as well as to measure a test compound's ability to prevent or delay a rise in blood pressure. The Dahl salt-sensive (DSS) hypertensive rat model is a model of hypertension that is sensitive to dietary salt (NaCl), and is described in Assay 5. See also Rapp (1982) *Hypertension* 4:753-763. The rat monocrotaline model of pulmonary arterial hypertension described, for example, in Kato et al. (2008) *J Cardiovasc. Pharmacol.* 51(1):18-23, is a reliable predictor of clinical efficacy for the treatment of pulmonary arterial hypertension. Heart failure animal models include the DSS rat model for heart failure and the aorto-caval fistula model (AV shunt), the latter of which is described, for example, in Norling et al. (1996) *J Amer. Soc. Nephrol.* 7:1038-1044. Other animal models, such as the hot plate, tail-flick and formalin tests, can be used to measure the analgesic properties of compounds of the invention, as well as the spinal nerve ligation (SNL) model of neuropathic pain. See, for example, Malmberg et al. (1999) *Current Protocols in Neuroscience* 8.9.1-8.9.15.

Compounds of the invention are expected to inhibit the NEP enzyme in any of the assays listed above, or assays of a similar nature. Thus, the aforementioned assays are useful in determining the therapeutic utility of compounds of the invention, for example, their utility as antihypertensive agents or antidiarrheal agents. Other properties and utilities of compounds of the invention can be demonstrated using other in vitro and in vivo assays well-known to those skilled in the art. Compounds of formula I may be active drugs as well as prodrugs. Thus, when discussing the activity of compounds of the invention, it is understood that any such prodrugs may not exhibit the expected activity in an assay, but are expected to exhibit the desired activity once metabolized.

Compounds of the invention are expected to be useful for the treatment and/or prevention of medical conditions responsive to NEP inhibition. Thus it is expected that patients suffering from a disease or disorder that is treated by inhibiting the NEP enzyme or by increasing the levels of its peptide substrates, can be treated by administering a therapeutically effective amount of a compound of the invention. For example, by inhibiting NEP, the compounds are expected to potentiate the biological effects of endogenous peptides that are metabolized by NEP, such as the natriuretic peptides, bombesin, bradykinins, calcitonin, endothelins, enkephalins, neurotensin, substance P and vasoactive intestinal peptide. Thus, these compounds are expected to have other physiological actions, for example, on the renal, central nervous, reproductive and gastrointestinal systems.

In one embodiment of the invention, patients suffering from a disease or disorder that is treated by inhibiting the NEP enzyme, are treated by administering a compound of the invention that is in its active form, i.e., a compound of formula I where $R^1$ is H, and $R^2$, $R^3$, $R^4$, $R^5$, $R^6$, and X are as defined for formula I.

In another embodiment, patients are treated by administering a compound that is metabolized in vitro to form a compound of formula I where $R^1$ is H, and $R^2$, $R^3$, $R^4$, $R^5$, $R^6$, and X are as defined for formula I.

In another embodiment, patients are treated by administering a compound of the invention that is in its prodrug form at the $R^1$ group, i.e., a compound of formula I where $R^1$ is selected from $C_{1-8}$alkyl optionally substituted with one or more fluoro atoms; $C_{1-3}$alkylene-$C_{6-10}$aryl; $C_{1-3}$alkylene-$C_{1-9}$heteroaryl; $C_{3-7}$cycloalkyl; $C_{2-3}$alkylene-OH; —[(CH$_2$)$_2$ O]$_{1-3}$CH$_3$; $C_{1-6}$alkylene-OC(O)R$^{20}$; $C_{1-6}$alkylene-NR$^{21}$R$^{22}$; —CH$_2$CH(NH$_2$)—COOCH$_3$; $C_{1-6}$alkylene-C(O)R$^{23}$; $C_{0-6}$alkylenemorpholine; $C_{1-6}$alkylene-SO$_2$—$C_{1-6}$alkyl;

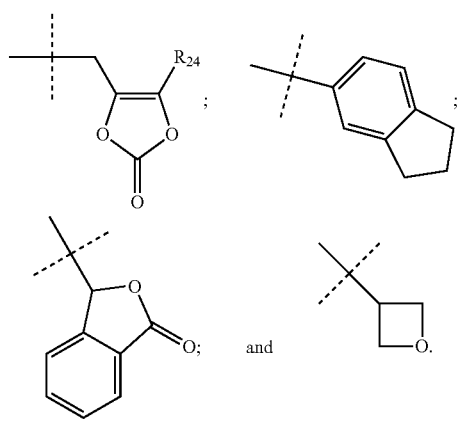

Cardiovascular Diseases

By potentiating the effects of vasoactive peptides like the natriuretic peptides and bradykinin, compounds of the invention are expected to find utility in treating and/or preventing medical conditions such as cardiovascular diseases. See, for example, Roques et al. (1993) *Pharmacol. Rev.* 45:87-146 and Dempsey et al. (2009) *Amer. J. of Pathology* 174(3):782-796. Cardiovascular diseases of particular interest include hypertension and heart failure. Hypertension includes, by way of illustration and not limitation: primary hypertension, which is also referred to as essential hypertension or idiopathic hypertension; secondary hypertension; hypertension with accompanying renal disease; severe hypertension with or without accompanying renal disease; pulmonary hypertension, including pulmonary arterial hypertension; and resistant hypertension. Heart failure includes, by way of illustration and not limitation: congestive heart failure; acute heart failure; chronic heart failure, for example with reduced left ventricular ejection fraction (also referred to as systolic heart failure) or with preserved left ventricular ejection fraction (also referred to as diastolic heart failure); and acute and chronic decompensated heart failure, with or without accompanying renal disease. Thus, one embodiment of the invention relates to a method for treating hypertension, particularly primary hypertension or pulmonary arterial hypertension, comprising administering to a patient a therapeutically effective amount of a compound of the invention.

For treatment of primary hypertension, the therapeutically effective amount is typically the amount that is sufficient to lower the patient's blood pressure. This would include both mild-to-moderate hypertension and severe hypertension.

When used to treat hypertension, the compound may be administered in combination with other therapeutic agents such as aldosterone antagonists, aldosterone synthase inhibitors, angiotensin-converting enzyme inhibitors and dual-acting angiotensin-converting enzyme/neprilysin inhibitors, angiotensin-converting enzyme 2 (ACE2) activators and stimulators, angiotensin-II vaccines, anti-diabetic agents, anti-lipid agents, anti-thrombotic agents, $AT_1$ receptor antagonists and dual-acting $AT_1$ receptor antagonist/neprilysin inhibitors, $β_1$-adrenergic receptor antagonists, dual-acting β-adrenergic receptor antagonist/$α_1$-receptor antagonists, calcium channel blockers, diuretics, endothelin receptor antagonists, endothelin converting enzyme inhibitors, neprilysin inhibitors, natriuretic peptides and their analogs, natriuretic peptide clearance receptor antagonists, nitric oxide donors, non-steroidal anti-inflammatory agents, phosphodiesterase inhibitors (specifically PDE-V inhibitors), prostaglandin receptor agonists, renin inhibitors, soluble guanylate cyclase stimulators and activators, and combinations thereof. In one particular embodiment of the invention, a compound of the invention is combined with an $AT_1$ receptor antagonist, a calcium channel blocker, a diuretic, or a combination thereof, and used to treat primary hypertension. In another particular embodiment of the invention, a compound of the invention is combined with an $AT_1$ receptor antagonist, and used to treat hypertension with accompanying renal disease. When used to treat resistant hypertension, the compound may be administered in combination with other therapeutic agents such as aldosterone synthase inhibitors.

For treatment of pulmonary arterial hypertension, the therapeutically effective amount is typically the amount that is sufficient to lower the pulmonary vascular resistance. Other goals of therapy are to improve a patient's exercise capacity. For example, in a clinical setting, the therapeutically effective amount can be the amount that improves a patient's ability to walk comfortably for a period of 6 minutes (covering a distance of approximately 20-40 meters). When used to treat pulmonary arterial hypertension the compound may be administered in combination with other therapeutic agents such as α-adrenergic receptor antagonists, $β_1$-adrenergic receptor antagonists, $β_2$-adrenergic receptor agonists, angiotensin-converting enzyme inhibitors, anticoagulants, calcium channel blockers, diuretics, endothelin receptor antagonists, PDE-V inhibitors, prostaglandin analogs, selective serotonin reuptake inhibitors, and combinations thereof. In one particular embodiment of the invention, a compound of the invention is combined with a PDE-V inhibitor or a selective serotonin reuptake inhibitor and used to treat pulmonary arterial hypertension.

Another embodiment of the invention relates to a method for treating heart failure, in particular congestive heart failure (including both systolic and diastolic congestive heart failure), comprising administering to a patient a therapeutically effective amount of a compound of the invention. Typically, the therapeutically effective amount is the amount that is sufficient to lower blood pressure and/or improve renal functions. In a clinical setting, the therapeutically effective amount can be the amount that is sufficient to improve cardiac hemodynamics, like for instance reduction in wedge pressure, right atrial pressure, filling pressure, and vascular resistance. In one embodiment, the compound is administered as an intravenous dosage form. When used to treat heart failure, the compound may be administered in combination with other therapeutic agents such as adenosine receptor antagonists, advanced glycation end product breakers, aldosterone antagonists, $AT_1$ receptor antagonists, $β_1$-adrenergic receptor antagonists, dual-acting β-adrenergic receptor antagonist/$α_1$-receptor antagonists, chymase inhibitors, digoxin, diuretics, endothelin converting enzyme (ECE) inhibitors, endothelin receptor antagonists, natriuretic peptides and their analogs, natriuretic peptide clearance receptor antagonists, nitric oxide donors, prostaglandin analogs, PDE-V inhibitors, soluble guanylate cyclase activators and stimulators, and vasopressin receptor antagonists. In one particular embodiment of the invention, a compound of the invention is combined with an aldosterone antagonist, a $β_1$-adrenergic receptor antagonist, an $AT_1$ receptor antagonist, or a diuretic, and used to treat congestive heart failure.

Diarrhea

As NEP inhibitors, compounds of the invention are expected to inhibit the degradation of endogenous enkephalins and thus such compounds may also find utility for the treatment of diarrhea, including infectious and secretory/watery diarrhea. See, for example, Baumer et al. (1992) *Gut* 33:753-758; Farthing (2006) *Digestive Diseases* 24:47-58; and Marçais-Collado (1987) *Eur. J. Pharmacol.* 144(2): 125-132. When used to treat diarrhea, compounds of the invention may be combined with one or more additional antidiarrheal agents.

Renal Diseases

By potentiating the effects of vasoactive peptides like the natriuretic peptides and bradykinin, compounds of the invention are expected to enhance renal function (see Chen et al. (1999) *Circulation* 100:2443-2448; Lipkin et al. (1997) *Kidney Int.* 52:792-801; and Dussaule et al. (1993) *Clin. Sci.* 84:31-39) and find utility in treating and/or preventing renal diseases. Renal diseases of particular interest include diabetic nephropathy, chronic kidney disease, proteinuria, and particularly acute kidney injury or acute renal failure (see Sharkovska et al. (2011) *Clin. Lab.* 57:507-515 and Newaz et al. (2010) *Renal Failure* 32:384-390). When used to treat renal disease, the compound may be administered in combination with other therapeutic agents such as angiotensin-converting enzyme inhibitors, $AT_1$ receptor antagonists, and diuretics.

Preventative Therapy

By potentiating the effects of the natriuretic peptides, compounds of the invention are also expected to be useful in preventative therapy, due to the antihypertrophic and anti-fibrotic effects of the natriuretic peptides (see Potter et al. (2009) *Handbook of Experimental Pharmacology* 191:341-366), for example in preventing the progression of cardiac insufficiency after myocardial infarction, preventing arterial restenosis after angioplasty, preventing thickening of blood vessel walls after vascular operations, preventing atherosclerosis, and preventing diabetic angiopathy.

Glaucoma

By potentiating the effects of the natriuretic peptides, compounds of the invention are expected to be useful to treat glaucoma. See, for example, Diestelhorst et al. (1989) *International Ophthalmology* 12:99-101. When used to treat glaucoma, compounds of the invention may be combined with one or more additional antiglaucoma agents.

Pain Relief

As NEP inhibitors, compounds of the invention are expected to inhibit the degradation of endogenous enkephalins and thus such compounds may also find utility as analgesics. See, for example, Roques et al. (1980) *Nature* 288:286-288 and Thanawala et al. (2008) *Current Drug Targets* 9:887-894. When used to treat pain, the compounds of the invention may be combined with one or more additional antinociceptive drugs such as aminopeptidase N or dipeptidyl peptidase III inhibitors, non-steroidal anti-inflammatory agents, monoamine reuptake inhibitors, muscle relaxants, NMDA receptor antagonists, opioid receptor agonists, 5-HT$_{1D}$ serotonin receptor agonists, and tricyclic antidepressants.

Other Utilities

Due to their NEP inhibition properties, compounds of the invention are also expected to be useful as antitussive agents, as well as find utility in the treatment of portal hypertension associated with liver cirrhosis (see Sansoe et al. (2005) *J. Hepatol.* 43:791-798), cancer (see Vesely (2005) *J. Investigative Med.* 53:360-365), depression (see Noble et al. (2007) *Exp. Opin. Ther. Targets* 11:145-159), menstrual disorders, preterm labor, pre-eclampsia, endometriosis, reproductive disorders (for example, male and female infertility, polycystic ovarian syndrome, implantation failure), and male and female sexual dysfunction, including male erectile dysfunction and female sexual arousal disorder. More specifically, the compounds of the invention are expected to be useful in treating female sexual dysfunction (see Pryde et al. (2006) *J. Med. Chem.* 49:4409-4424), which is often defined as a female patient's difficulty or inability to find satisfaction in sexual expression. This covers a variety of diverse female sexual disorders including, by way of illustration and not limitation, hypoactive sexual desire disorder, sexual arousal disorder, orgasmic disorder and sexual pain disorder. When used to treat such disorders, especially female sexual dysfunction, compounds of the invention may be combined with one or more of the following secondary agents: PDE-V inhibitors, dopamine agonists, estrogen receptor agonists and/or antagonists, androgens, and estrogens. Due to their NEP inhibition properties, compounds of the invention are also expected to have anti-inflammatory properties, and are expected to have utility as such, particularly when used in combination with statins.

Recent studies suggest that NEP plays a role in regulating nerve function in insulin-deficient diabetes and diet induced obesity. Coppey et al. (2011) *Neuropharmacology* 60:259-266. Therefore, due to their NEP inhibition properties, compounds of the invention are also expected to be useful in providing protection from nerve impairment caused by diabetes or diet induced obesity.

The amount of the compound of the invention administered per dose or the total amount administered per day may be predetermined or it may be determined on an individual patient basis by taking into consideration numerous factors, including the nature and severity of the patient's condition, the condition being treated, the age, weight, and general health of the patient, the tolerance of the patient to the active agent, the route of administration, pharmacological considerations such as the activity, efficacy, pharmacokinetics and toxicology profiles of the compound and any secondary agents being administered, and the like. Treatment of a patient suffering from a disease or medical condition (such as hypertension) can begin with a predetermined dosage or a dosage determined by the treating physician, and will continue for a period of time necessary to prevent, ameliorate, suppress, or alleviate the symptoms of the disease or medical condition. Patients undergoing such treatment will typically be monitored on a routine basis to determine the effectiveness of therapy. For example, in treating hypertension, blood pressure measurements may be used to determine the effectiveness of treatment. Similar indicators for other diseases and conditions described herein, are well known and are readily available to the treating physician. Continuous monitoring by the physician will insure that the optimal amount of the compound of the invention will be administered at any given time, as well as facilitating the determination of the duration of treatment. This is of particular value when secondary agents are also being administered, as their selection, dosage, and duration of therapy may also require adjustment. In this way, the treatment regimen and dosing schedule can be adjusted over the course of therapy so that the lowest amount of active agent that exhibits the desired effectiveness is administered and, further, that administration is continued only so long as is necessary to successfully treat the disease or medical condition.

Research Tools

Since compounds of the invention possess NEP enzyme inhibition activity, such compounds are also useful as research tools for investigating or studying biological systems or samples having a NEP enzyme, for example to study diseases where the NEP enzyme or its peptide substrates plays a role. Any suitable biological system or sample having a NEP enzyme may be employed in such studies which may be conducted either in vitro or in vivo. Representative biological systems or samples suitable for such studies include, but are not limited to, cells, cellular extracts, plasma membranes, tissue samples, isolated organs, mammals (such as mice, rats, guinea pigs, rabbits, dogs, pigs, humans, and so forth), and the like, with mammals being of particular interest. In one particular embodiment of the invention, NEP enzyme activity in a mammal is inhibited by administering a NEP-inhibiting amount of a compound of the invention. Compounds of the invention can also be used as research tools by conducting biological assays using such compounds.

When used as a research tool, a biological system or sample comprising a NEP enzyme is typically contacted with a NEP enzyme-inhibiting amount of a compound of the invention. After the biological system or sample is exposed to the compound, the effects of inhibiting the NEP enzyme are determined using conventional procedures and equipment, such as by measuring receptor binding in a binding assay or measuring ligand-mediated changes in a functional assay. Exposure encompasses contacting cells or tissue with the compound, administering the compound to a mammal, for example by i.p., p. o, i.v., s.c., or inhaled administration, and so forth. This determining step can involve measuring a response (a quantitative analysis) or can involve making an observation (a qualitative analysis). Measuring a response involves, for example, determining the effects of the compound on the biological system or sample using conventional procedures and equipment, such as enzyme activity assays and measuring enzyme substrate or product mediated changes in functional assays. The assay results can be used to determine the activity level as well as the amount of compound necessary to achieve the desired result, that is, a NEP enzyme-inhibiting amount. Typically, the determining step will involve determining the effects of inhibiting the NEP enzyme.

Additionally, compounds of the invention can be used as research tools for evaluating other chemical compounds, and thus are also useful in screening assays to discover, for example, new compounds having NEP-inhibiting activity. In this manner, a compound of the invention is used as a standard in an assay to allow comparison of the results obtained with a test compound and with compounds of the invention to identify those test compounds that have about equal or superior activity, if any. For example, $pK_i$ data for a test compound or a group of test compounds is compared to the $pK_i$ data for a compound of the invention to identify those test compounds that have the desired properties, for example, test compounds having a $pK_i$ value about equal or superior to a compound of the invention, if any. This aspect of the invention includes, as separate embodiments, both the generation of comparison data (using the appropriate assays) and the analysis of test data to identify test compounds of interest. Thus, a test compound can be evaluated in a biological assay, by a method comprising the steps of: (a) conducting a biological assay with a test compound to provide a first assay value; (b) conducting the biological assay with a compound of the invention to provide a second assay value; wherein step (a) is conducted either before, after or concurrently with step (b); and (c) comparing the first assay value from step (a) with the second assay value from step (b). Exemplary biological assays include aNEP enzyme inhibition assay.

Pharmaceutical Compositions and Formulations

Compounds of the invention are typically administered to a patient in the form of a pharmaceutical composition or formulation. Such pharmaceutical compositions may be administered to the patient by any acceptable route of administration including, but not limited to, oral, rectal, vaginal, nasal, inhaled, topical (including transdermal), ocular, and parenteral modes of administration. Further, the compounds of the invention may be administered, for example orally, in multiple doses per day (for example, two, three, or four times daily), in a single daily dose or a single weekly dose. It will be understood that any form of the compounds of the invention, (that is, free base, free acid, pharmaceutically acceptable salt, solvate, etc.) that is suitable for the particular mode of administration can be used in the pharmaceutical compositions discussed herein.

Accordingly, in one embodiment, the invention relates to a pharmaceutical composition comprising a pharmaceutically acceptable carrier and a compound of the invention. The compositions may contain other therapeutic and/or formulating agents if desired. When discussing compositions, the "compound of the invention" may also be referred to herein as the "active agent," to distinguish it from other components of the formulation, such as the carrier. Thus, it is understood that the term "active agent" includes compounds of formula I as well as pharmaceutically acceptable salts, solvates and prodrugs of that compound.

The pharmaceutical compositions of the invention typically contain a therapeutically effective amount of a compound of the invention. Those skilled in the art will recognize, however, that a pharmaceutical composition may contain more than a therapeutically effective amount, such as in bulk compositions, or less than a therapeutically effective amount, that is, individual unit doses designed for multiple administration to achieve a therapeutically effective amount. Typically, the composition will contain from about 0.01-95 wt % of active agent, including, from about 0.01-30 wt %, such as from about 0.01-10 wt %, with the actual amount depending upon the formulation itself, the route of administration, the frequency of dosing, and so forth. In one embodiment, a composition suitable for an oral dosage form, for example, may contain about 5-70 wt %, or from about 10-60 wt % of active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable composition for a particular mode of administration is well within the scope of those skilled in the pharmaceutical arts. Additionally, carriers or excipients used in such compositions are commercially available. By way of further illustration, conventional formulation techniques are described in *Remington: The Science and Practice of Pharmacy*, $20^{th}$ Edition, Lippincott Williams & White, Baltimore, Md. (2000); and H. C. Ansel et al., *Pharmaceutical Dosage Forms and Drug Delivery Systems*, $7^{th}$ Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; compressed propellant gases, such as chlorofluorocarbons and hydrofluorocarbons; and other non-toxic compatible substances employed in pharmaceutical compositions.

Pharmaceutical compositions are typically prepared by thoroughly and intimately mixing or blending the active agent with a pharmaceutically acceptable carrier and one or more optional ingredients. The resulting uniformly blended mixture may then be shaped or loaded into tablets, capsules, pills, canisters, cartridges, dispensers and the like using conventional procedures and equipment.

In one embodiment, the pharmaceutical compositions are suitable for oral administration. Suitable compositions for oral administration may be in the form of capsules, tablets, pills, lozenges, cachets, dragees, powders, granules; solutions or suspensions in an aqueous or non-aqueous liquid; oil-in-water or water-in-oil liquid emulsions; elixirs or syrups; and the like; each containing a predetermined amount of the active agent.

When intended for oral administration in a solid dosage form (capsules, tablets, pills and the like), the composition will typically comprise the active agent and one or more pharmaceutically acceptable carriers, such as sodium citrate or dicalcium phosphate. Solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants may also be present in the pharmaceutical compositions. Exemplary coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, and the like. Examples of pharmaceutically acceptable antioxidants include: water-soluble antioxidants, such as ascorbic acid, cysteine hydrochloride, sodium bisulfate, sodium metabisulfate sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like.

Compositions may also be formulated to provide slow or controlled release of the active agent using, by way of example, hydroxypropyl methyl cellulose in varying proportions or other polymer matrices, liposomes and/or microspheres. In addition, the pharmaceutical compositions of the invention may contain opacifying agents and may be formulated so that they release the active agent only, or preferentially, in a certain portion of the gastrointestinal tract, optionally, in a delayed manner. Examples of embedding compositions which can be used include polymeric substances and waxes. The active agent can also be in micro-encapsulated form, optionally with one or more of the above-described excipients.

Suitable liquid dosage forms for oral administration include, by way of illustration, pharmaceutically acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (for example, cottonseed, groundnut, corn, germ, olive, castor and sesame oils), glycerol, tetrahydrofuryl alcohol, polyethylene glycols and fatty acid esters of sorbitan, and mixtures thereof. Suspensions may contain suspending agents such as, for example, ethoxylated isostearyl alcohols, polyoxyethylene sorbitol and sorbitan esters, microcrystalline cellulose, aluminium metahydroxide, bentonite, agar-agar and tragacanth, and mixtures thereof.

When intended for oral administration, the pharmaceutical compositions of the invention may be packaged in a unit dosage form. The term "unit dosage form" refers to a physically discrete unit suitable for dosing a patient, that is, each unit containing a predetermined quantity of the active agent calculated to produce the desired therapeutic effect either alone or in combination with one or more additional units. For example, such unit dosage forms may be capsules, tablets, pills, and the like.

In another embodiment, the compositions of the invention are suitable for inhaled administration, and will typically be in the form of an aerosol or a powder. Such compositions are generally administered using well-known delivery devices, such as a nebulizer, dry powder, or metered-dose inhaler. Nebulizer devices produce a stream of high velocity air that causes the composition to spray as a mist that is carried into a patient's respiratory tract. An exemplary nebulizer formulation comprises the active agent dissolved in a carrier to form a solution, or micronized and combined with a carrier to form a suspension of micronized particles of respirable size. Dry powder inhalers administer the active agent as a free-flowing powder that is dispersed in a patient's airstream during inspiration. An exemplary dry powder formulation comprises the active agent dry-blended with an excipient such as lactose, starch, mannitol, dextrose, polylactic acid, polylactide-co-glycolide, and combinations thereof. Metered-dose inhalers discharge a measured amount of the active agent using compressed propellant gas. An exemplary metered-dose formulation comprises a solution or suspension of the active agent in a liquefied propellant, such as a chlorofluorocarbon or hydrofluoroalkane. Optional components of such formulations include co-solvents, such as ethanol or pentane, and surfactants, such as sorbitan trioleate, oleic acid, lecithin, glycerin, and sodium lauryl sulfate. Such compositions are typically prepared by adding chilled or pressurized hydrofluoroalkane to a suitable container containing the active agent, ethanol (if present) and the surfactant (if present). To prepare a suspension, the active agent is micronized and then combined with the propellant. Alternatively, a suspension formulation can be prepared by spray drying a coating of surfactant on micronized particles of the active agent. The formulation is then loaded into an aerosol canister, which forms a portion of the inhaler.

Compounds of the invention can also be administered parenterally (for example, by subcutaneous, intravenous, intramuscular, or intraperitoneal injection). For such administration, the active agent is provided in a sterile solution, suspension, or emulsion. Exemplary solvents for preparing such formulations include water, saline, low molecular weight alcohols such as propylene glycol, polyethylene glycol, oils, gelatin, fatty acid esters such as ethyl oleate, and the like. Parenteral formulations may also contain one or more anti-oxidants, solubilizers, stabilizers, preservatives, wetting agents, emulsifiers, and dispersing agents. Surfactants, additional stabilizing agents or pH-adjusting agents (acids, bases or buffers) and anti-oxidants are particularly useful to provide stability to the formulation, for example, to minimize or avoid hydrolysis of ester and amide linkages that may be present in the compound. These formulations may be rendered sterile by use of a sterile injectable medium, a sterilizing agent, filtration, irradiation, or heat. In one particular embodiment, the parenteral formulation comprises an aqueous cyclodextrin solution as the pharmaceutically acceptable carrier. Suitable cyclodextrins include cyclic molecules containing six or more α-D-glucopyranose units linked at the 1,4 positions by a linkages as in amylase, β-cyclodextrin or cycloheptaamylose. Exemplary cyclodextrins include cyclodextrin derivatives such as hydroxypropyl and sulfobutyl ether cyclodextrins such as hydroxypropyl-β-cyclodextrin and sulfobutyl ether β-cyclodextrin. Exemplary buffers for such formulations include carboxylic acid-based buffers such as citrate, lactate and maleate buffer solutions.

Compounds of the invention can also be administered transdermally using known transdermal delivery systems and excipients. For example, the compound can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

Secondary Agents

The compounds of the invention may be useful as the sole treatment of a disease or may be combined with one or more additional therapeutic agents in order to obtain the desired therapeutic effect. Thus, in one embodiment, pharmaceutical compositions of the invention contain other drugs that are co-administered with a compound of the invention. For example, the composition may further comprise one or more drugs (also referred to as "secondary agents(s)"). Such therapeutic agents are well known in the art, and include adenosine receptor antagonists, α-adrenergic receptor antagonists, $\beta_1$-adrenergic receptor antagonists, $\beta_2$-adrenergic receptor agonists, dual-acting β-adrenergic receptor antagonist/$\alpha_1$-receptor antagonists, advanced glycation end product breakers, aldosterone antagonists, aldosterone synthase inhibitors, aminopeptidase N inhibitors, androgens, angiotensin-converting enzyme inhibitors and dual-acting angiotensin-converting enzyme/neprilysin inhibitors, angiotensin-converting enzyme 2 activators and stimulators, angiotensin-II vaccines, anticoagulants, anti-diabetic agents, antidiarrheal agents, anti-glaucoma agents, anti-lipid agents, antinociceptive agents, anti-thrombotic agents, $AT_1$ receptor antagonists and dual-acting $AT_1$ receptor antagonist/neprilysin inhibitors and multifunctional angiotensin receptor blockers, bradykinin receptor antagonists, calcium channel blockers, chymase inhibitors, digoxin, diuretics, dopamine agonists, endothelin converting enzyme inhibitors, endothelin receptor antagonists, HMG-CoA reductase inhibitors, estrogens, estrogen receptor agonists and/or antagonists, monoamine reuptake inhibitors, muscle relaxants, natriuretic peptides and their analogs, natriuretic peptide clearance receptor antagonists, neprilysin inhibitors, nitric oxide donors, non-steroidal anti-inflammatory agents, N-methyl d-aspartate receptor antagonists, opioid receptor agonists, phosphodiesterase inhibitors, prostaglandin analogs, prostaglandin receptor agonists, renin inhibitors, selective serotonin reuptake inhibitors, sodium channel blocker, soluble guanylate cyclase stimulators and activators, tricyclic antidepressants, vasopressin receptor antagonists, and combinations thereof. Specific examples of these agents are detailed herein.

Accordingly, in yet another aspect of the invention, a pharmaceutical composition comprises a compound of the invention, a second active agent, and a pharmaceutically acceptable carrier. Third, fourth etc. active agents may also be included in the composition. In combination therapy, the amount of compound of the invention that is administered, as well as the amount of secondary agents, may be less than the amount typically administered in monotherapy.

Compounds of the invention may be physically mixed with the second active agent to form a composition containing both agents; or each agent may be present in separate and distinct compositions which are administered to the patient simultaneously or at separate times. For example, a compound of the invention can be combined with a second active agent using conventional procedures and equipment to form a combination of active agents comprising a compound of the invention and a second active agent. Additionally, the active agents may be combined with a pharmaceutically acceptable carrier to form a pharmaceutical composition comprising a compound of the invention, a second active agent and a pharmaceutically acceptable carrier. In this embodiment, the components of the composition are typically mixed or blended to create a physical mixture. The physical mixture is then administered in a therapeutically effective amount using any of the routes described herein.

Alternatively, the active agents may remain separate and distinct before administration to the patient. In this embodiment, the agents are not physically mixed together before administration but are administered simultaneously or at separate times as separate compositions. Such compositions can be packaged separately or may be packaged together in a kit. When administered at separate times, the secondary agent will typically be administered less than 24 hours after administration of the compound of the invention, ranging anywhere from concurrent with administration of the compound of the invention to about 24 hours post-dose. This is also referred to as sequential administration. Thus, a compound of the invention can be orally administered simultaneously or sequentially with another active agent using two tablets, with one tablet for each active agent, where sequential may mean being administered immediately after administration of the compound of the invention or at some predetermined time later (for example, one hour later or three hours later). It is also contemplated that the secondary agent may be administered more than 24 hours after administration of the compound of the invention. Alternatively, the combination may be administered by different routes of administration, that is, one orally and the other by inhalation.

In one embodiment, the kit comprises a first dosage form comprising a compound of the invention and at least one additional dosage form comprising one or more of the secondary agents set forth herein, in quantities sufficient to carry out the methods of the invention. The first dosage form and the second (or third, etc.) dosage form together comprise a therapeutically effective amount of active agents for the treatment or prevention of a disease or medical condition in a patient.

Secondary agent(s), when included, are present in a therapeutically effective amount such that they are typically administered in an amount that produces a therapeutically beneficial effect when co-administered with a compound of the invention. The secondary agent can be in the form of a pharmaceutically acceptable salt, solvate, optically pure stereoisomer, and so forth. The secondary agent may also be in the form of a prodrug, for example, a compound having a carboxylic acid group that has been esterified. Thus, secondary agents listed herein are intended to include all such forms, and are commercially available or can be prepared using conventional procedures and reagents.

In one embodiment, compounds of the invention are administered in combination with an adenosine receptor antagonist, representative examples of which include, but are not limited to, naxifylline, rolofylline, SLV-320, theophylline, and tonapofylline.

In one embodiment, compounds of the invention are administered in combination with an α-adrenergic receptor antagonist, representative examples of which include, but are not limited to, doxazosin, prazosin, tamsulosin, and terazosin.

Compounds of the invention may also be administered in combination with a $\beta_1$-adrenergic receptor antagonist ("$\beta_1$-blockers"). Representative $\beta_1$-blockers include, but are not limited to, acebutolol, alprenolol, amosulalol, arotinolol, atenolol, befunolol, betaxolol, bevantolol, bisoprolol, bopindolol, bucindolol, bucumolol, bufetolol, bufuralol, bunitrolol, bupranolol, bubridine, butofilolol, carazolol, carteolol, carvedilol, celiprolol, cetamolol, cloranolol, dilevalol, epanolol, esmolol, indenolol, labetolol, levobunolol, mepindolol, metipranolol, metoprolol such as metoprolol succinate and metoprolol tartrate, moprolol, nadolol, nadoxolol, nebivalol, nipradilol, oxprenolol, penbutolol, perbutolol, pindolol, practolol, pronethalol, propranolol, sotalol, sufinalol, talindol, tertatolol, tilisolol, timolol, toliprolol, xibenolol, and combinations thereof. In one particular embodiment, the $\beta_1$-antagonist is selected from atenolol, bisoprolol, metoprolol, propranolol, sotalol, and combinations thereof. Typically, the $\beta_1$-blocker will be administered in an amount sufficient to provide from about 2-900 mg per dose.

In one embodiment, compounds of the invention are administered in combination with a $\beta_2$-adrenergic receptor agonist, representative examples of which include, but are not limited to, albuterol, bitolterol, fenoterol, formoterol, indacaterol, isoetharine, levalbuterol, metaproterenol, pirbuterol, salbutamol, salmefamol, salmeterol, terbutaline, vilanterol, and the like Typically, the $\beta_2$-adrenergic receptor agonist will be administered in an amount sufficient to provide from about 0.05-500 µg per dose.

In one embodiment, compounds of the invention are administered in combination with an advanced glycation end product (AGE) breaker, examples of which include, by way of illustration and not limitation, alagebrium (or ALT-711), and TRC4149.

In another embodiment, compounds of the invention are administered in combination with an aldosterone antagonist, representative examples of which include, but are not limited to, eplerenone, spironolactone, and combinations thereof. Typically, the aldosterone antagonist will be administered in an amount sufficient to provide from about 5-300 mg per day.

In one embodiment, compounds of the invention are administered in combination with an aminopeptidase N or dipeptidyl peptidase III inhibitor, examples of which include, by way of illustration and not limitation, bestatin and PC18 (2-amino-4-methylsulfonyl butane thiol, methionine thiol).

Compounds of the invention can also be administered in combination with an angiotensin-converting enzyme (ACE) inhibitor. Representative ACE inhibitors include, but are not limited to, accupril, alacepril, benazepril, benazeprilat, captopril, ceranapril, cilazapril, delapril, enalapril, enalaprilat, fosinopril, fosinoprilat, imidapril, lisinopril, moexipril, monopril, moveltipril, pentopril, perindopril, quinapril, quinaprilat, ramipril, ramiprilat, saralasin acetate, spirapril, temocapril, trandolapril, zofenopril, and combinations thereof. In a particular embodiment, the ACE inhibitor is selected from: benazepril, captopril, enalapril, lisinopril, ramipril, and combinations thereof. Typically, the ACE inhibitor will be administered in an amount sufficient to provide from about 1-150 mg per day.

In another embodiment, compounds of the invention are administered in combination with a dual-acting angiotensin-converting enzyme/neprilysin (ACE/NEP) inhibitor, examples of which include, but are not limited to: AVE-0848 ((4S,7S,12bR)-7-[3-methyl-2(S)-sulfanylbutyramido]-6-oxo-1,2,3,4,6,7,8,12b-octahydropyrido[2,1-a][2]-benzazepine-4-carboxylic acid); AVE-7688 (ilepatril) and its parent compound; BMS-182657 (2-[2-oxo-3(S)-[3-phenyl-2(S)-sulfanylpropionamido]-2,3,4,5-tetrahydro-1H-1-benzazepin-1-yl]acetic acid); CGS-35601 (N-[1-[4-methyl-2 (S)-sulfanylpentanamido]cyclopentylcarbonyl]-L-tryptophan); fasidotril; fasidotrilate; enalaprilat; ER-32935 ((3R,6S,9aR)-6-[3(S)-methyl-2(S)-sulfanylpentanamido]-5-oxoperhydrothiazolo[3,2-a]azepine-3-carboxylic acid); gempatrilat; MDL-101264 ((4S,7S,12bR)-7-[2(S)-(2-morpholinoacetylthio)-3-phenylpropionamido]-6-oxo-1,2,3,4,6,7,8,12b-octahydropyrido[2,1-a][2]benzazepine-4-carboxylic acid); MDL-101287 ([4S-[4α,7α(R*), 12bβ]]-7-[2-(carboxymethyl)-3-phenylpropionamido]-6-oxo-1,2,3,4,6,7,8,12b-octahydropyrido[2,1-a][2]benzazepine-4-carboxylic acid); omapatrilat; RB-105 (N-[2(S)-(mercaptomethyl)-3 (R)-phenylbutyl]-L-alanine); sampatrilat; SA-898 ((2R, 4R)—N-[2-(2-hydroxyphenyl)-3-(3-mercaptopropionyl)thiazolidin-4-ylcarbonyl]-L-phenylalanine); Sch-50690 (N-[1 (S)-carboxy-2-[N2-(methanesulfonyl)-L-lysylamino]ethyl]-L-valyl-L-tyrosine); and combinations thereof, may also be included. In one particular embodiment, the ACE/NEP inhibitor is selected from: AVE-7688, enalaprilat, fasidotril, fasidotrilate, omapatrilat, sampatrilat, and combinations thereof.

In one embodiment, compounds of the invention are administered in combination with an angiotensin-converting enzyme 2 (ACE2) activator or stimulator.

In one embodiment, compounds of the invention are administered in combination with an angiotensin-II vaccine, examples of which include, but are not limited to ATR12181 and CYT006-AngQb.

In one embodiment, compounds of the invention are administered in combination with an anticoagulant, representative examples of which include, but are not limited to: coumarins such as warfarin; heparin; and direct thrombin inhibitors such as argatroban, bivalirudin, dabigatran, and lepirudin.

In yet another embodiment, compounds of the invention are administered in combination with an anti-diabetic agent. Representative anti-diabetic agents include injectable drugs as well as orally effective drugs, and combinations thereof. Examples of injectable drugs include, but are not limited to, insulin and insulin derivatives. Examples of orally effective drugs include, but are not limited to: biguanides such as metformin; glucagon antagonists; α-glucosidase inhibitors such as acarbose and miglitol; dipeptidyl peptidase IV inhibitors (DPP-IV inhibitors) such as alogliptin, denagliptin, linagliptin, saxagliptin, sitagliptin, and vildagliptin; meglitinides such as repaglinide; oxadiazolidinediones; sulfonylureas such as chlorpropamide, glimepiride, glipizide, glyburide, and tolazamide; thiazolidinediones such as pioglitazone and rosiglitazone; and combinations thereof.

In another embodiment, compounds of the invention are administered in combination with antidiarrheal treatments. Representative treatment options include, but are not limited to, oral rehydration solutions (ORS), loperamide, diphenoxylate, and bismuth subsalicylate.

In yet another embodiment, a compound of the invention is administered in combination with an anti-glaucoma agent. Representative anti-glaucoma agents include, but are not limited to: α-adrenergic agonists such as brimonidine; $\beta_1$-adrenergic receptor antagonists; topical $\beta_1$-blockers such as betaxolol, levobunolol, and timolol; carbonic anhydrase inhibitors such as acetazolamide, brinzolamide, or dorzolamide; cholinergic agonists such as cevimeline and DMXB-anabaseine; epinephrine compounds; miotics such as pilocarpine; and prostaglandin analogs.

In yet another embodiment, compounds of the invention are administered in combination with an anti-lipid agent. Representative anti-lipid agents include, but are not limited to: cholesteryl ester transfer protein inhibitors (CETPs) such as anacetrapib, dalcetrapib, and torcetrapib; statins such as atorvastatin, fluvastatin, lovastatin, pravastatin, rosuvastatin and simvastatin; and combinations thereof.

In one embodiment, compounds of the invention are administered in combination with an anti-thrombotic agent. Representative anti-thrombotic agents include, but are not limited to: aspirin; anti-platelet agents such as clopidogrel, prasugrel, and ticlopidine; heparin, and combinations thereof.

In one embodiment, compounds of the invention are administered in combination with an $AT_1$ receptor antagonist, also known as angiotensin II type 1 receptor blockers (ARBs). Representative ARBs include, but are not limited to, abitesartan, azilsartan (e.g., azilsartan medoxomil), benzyllosartan, candesartan, candesartan cilexetil, elisartan, embusartan, enoltasosartan, eprosartan, EXP3174, fonsartan, forasartan, glycyllosartan, irbesartan, isoteoline, losartan, medoximil, milfasartan, olmesartan (e.g., olmesartan medoxomil), opomisartan, pratosartan, ripisartan, saprisartan, saralasin, sarmesin, TAK-591, tasosartan, telmisartan, valsartan, zolasartan, and combinations thereof. In a particular embodiment, the ARB is selected from azilsartan medoxomil, candesartan cilexetil, eprosartan, irbesartan, losartan, olmesartan medoxomil, saprisartan, tasosartan, telmisartan, valsartan, and combinations thereof. Exemplary salts and/or prodrugs include candesartan cilexetil, eprosartan mesylate, losartan potassium salt, and olmesartan medoxomil. Typically, the ARB will be administered in an amount sufficient to provide from about 4-600 mg per dose, with exemplary daily dosages ranging from 20-320 mg per day.

Compounds of the invention may also be administered in combination with a dual-acting agent, such as an $AT_1$ receptor antagonist/neprilysin inhibitor (ARB/NEP) inhibitor, examples of which include, but are not limited to, compounds described in U.S. Publication Nos. 2008/0269305 and 2009/0023228, both to Allegretti et al. filed on Apr. 23, 2008, such as the compound, 4'-{2-ethoxy-4-ethyl-5-[((S)-2-mercapto-4-methylpentanoylamino)-methyl]imidazol-1-ylmethyl}-3'-fluorobiphenyl-2-carboxylic acid.

Compounds of the invention may also be administered in combination with multifunctional angiotensin receptor blockers as described in Kurtz & Klein (2009) *Hypertension Research* 32:826-834.

In one embodiment, compounds of the invention are administered in combination with a bradykinin receptor antagonist, for example, icatibant (HOE-140). It is expected that this combination therapy may present the advantage of preventing angioedema or other unwanted consequences of elevated bradykinin levels.

In one embodiment, compounds of the invention are administered in combination with a calcium channel blocker. Representative calcium channel blockers include, but are not limited to, amlodipine, anipamil, aranipine, bamidipine, bencyclane, benidipine, bepridil, clentiazem, cilnidipine, cinnarizine, diltiazem, efonidipine, elgodipine, etafenone, felodipine, fendiline, flunarizine, gallopamil, isradipine, lacidipine, lercanidipine, lidoflazine, lomerizine, manidipine, mibefradil, nicardipine, nifedipine, niguldipine, niludipine, nilvadipine, nimodipine, nisoldipine, nitrendipine, nivaldipine, perhexiline, prenylamine, ryosidine, semotiadil, terodiline, tiapamil, verapamil, and combinations thereof. In a particular embodiment, the calcium channel blocker is selected from amlodipine, bepridil, diltiazem, felodipine, isradipine, lacidipine, nicardipine, nifedipine, niguldipine, niludipine, nimodipine, nisoldipine, ryosidine, verapamil, and combinations thereof. Typically, the calcium channel blocker will be administered in an amount sufficient to provide from about 2-500 mg per dose.

In one embodiment, compounds of the invention are administered in combination with a chymase inhibitor, such as TPC-806 and 2-(5-formylamino-6-oxo-2-phenyl-1,6-dihydropyrimidine-1-yl)-N-[{3,4-dioxo-1-phenyl-7-(2-pyridyloxy)}-2-heptyl]acetamide (NK3201).

In one embodiment, compounds of the invention are administered in combination with a diuretic. Representative diuretics include, but are not limited to: carbonic anhydrase inhibitors such as acetazolamide and dichlorphenamide; loop diuretics, which include sulfonamide derivatives such as acetazolamide, ambuside, azosemide, bumetanide, butazolamide, chloraminophenamide, clofenamide, clopamide, clorexolone, disulfamide, ethoxzolamide, furosemide, mefruside, methazolamide, piretanide, torsemide, tripamide, and xipamide, as well as non-sulfonamide diuretics such as ethacrynic acid and other phenoxyacetic acid compounds such as tienilic acid, indacrinone and quincarbate; osmotic diuretics such as mannitol; potassium-sparing diuretics, which include aldosterone antagonists such as spironolactone, and $Na^+$ channel inhibitors such as amiloride and triamterene; thiazide and thiazide-like diuretics such as althiazide, bendroflumethiazide, benzylhydrochlorothiazide, benzthiazide, buthiazide, chlorthalidone, chlorothiazide, cyclopenthiazide, cyclothiazide, epithiazide, ethiazide, fenquizone, flumethiazide, hydrochlorothiazide, hydroflumethiazide, indapamide, methylclothiazide, meticrane, metolazone, paraflutizide, polythiazide, quinethazone, teclothiazide, and trichloromethiazide; and combinations thereof. In a particular embodiment, the diuretic is selected from amiloride, bumetanide, chlorothiazide, chlorthalidone, dichlorphenamide, ethacrynic acid, furosemide, hydrochlorothiazide, hydroflumethiazide, indapamide, methylclothiazide, metolazone, torsemide, triamterene, and combinations thereof. The diuretic will be administered in an amount sufficient to provide from about 5-50 mg per day, more typically 6-25 mg per day, with common dosages being 6.25 mg, 12.5 mg or 25 mg per day.

Compounds of the invention may also be administered in combination with an endothelin converting enzyme (ECE) inhibitor, examples of which include, but are not limited to, phosphoramidon, CGS 26303, and combinations thereof.

In a particular embodiment, compounds of the invention are administered in combination with an endothelin receptor antagonist. Representative endothelin receptor antagonists include, but are not limited to: selective endothelin receptor antagonists that affect endothelin A receptors, such as avosentan, ambrisentan, atrasentan, BQ-123, clazosentan, darusentan, sitaxentan, and zibotentan; and dual endothelin receptor antagonists that affect both endothelin A and B receptors, such as bosentan, macitentan, tezosentan).

In yet another embodiment, a compound of the invention is administered in combination with one or more HMG-CoA reductase inhibitors, which are also known as statins. Representative statins include, but are not limited to, atorvastatin, fluvastatin, lovastatin, pitavastatin, pravastatin, rosuvastatin and simvastatin.

In one embodiment, compounds of the invention are administered in combination with a monoamine reuptake inhibitor, examples of which include, by way of illustration and not limitation, norepinephrine reuptake inhibitors such as atomoxetine, buprorion and the buprorion metabolite hydroxybuproprion, maprotiline, reboxetine, and viloxazine; selective serotonin reuptake inhibitors (SSRIs) such as citalopram and the citalopram metabolite desmethylcitalopram, dapoxetine, escitalopram (e.g., escitalopram oxalate), fluoxetine and the fluoxetine desmethyl metabolite norfluoxetine, fluvoxamine (e.g., fluvoxamine maleate), paroxetine, sertraline and the sertraline metabolite demethylsertraline; dual serotonin-norepinephrine reuptake inhibitors (SNRIs) such as bicifadine, duloxetine, milnacipran, nefazodone, and venlafaxine; and combinations thereof.

In another embodiment, compounds of the invention are administered in combination with a muscle relaxant, examples of which include, but are not limited to: carisoprodol, chlorzoxazone, cyclobenzaprine, diflunisal, metaxalone, methocarbamol, and combinations thereof.

In one embodiment, compounds of the invention are administered in combination with a natriuretic peptide or analog, examples of which include but are not limited to: carperitide, CD-NP (Nile Therapeutics), CU-NP, nesiritide, PL-3994 (Palatin Technologies, Inc.), ularitide, cenderitide, and compounds described in Ogawa et al (2004) *J. Biol. Chem.* 279:28625-31. These compounds are also referred to as natriuretic peptide receptor-A (NPR-A) agonists. In another embodiment, compounds of the invention are administered in combination with a natriuretic peptide clearance receptor (NPR-C) antagonist such as SC-46542, cANF (4-23), and AP-811 (Veale (2000) *Bioorg Med Chem Lett* 10:1949-52). For example, AP-811 has shown synergy when combined with the NEP inhibitor, thiorphan (Wegner (1995) *Clin. Exper. Hypert.* 17:861-876).

In another embodiment, compounds of the invention are administered in combination with a neprilysin (NEP) inhibitor. Representative NEP inhibitors include, but are not limited to: AHU-377; candoxatril; candoxatrilat; dexecadotril ((+)-N-[2(R)-(acetylthiomethyl)-3-phenylpropionyl]glycine benzyl ester); CGS-24128 (3-[3-(biphenyl-4-yl)-2-(phosphonomethylamino)propionamido]propionic acid); CGS-24592 ((S)-3-[3-(biphenyl-4-yl)-2-(phosphonomethylamino)propionamido]propionic acid); CGS-25155 (N-[9(R)-(acetylthiomethyl)-10-oxo-1-azacyclodecan-2(S)-ylcarbonyl]-4(R)-hydroxy-L-proline benzyl ester); 3-(1-carbamoylcyclohexyl)propionic acid derivatives described in WO 2006/027680 to Hepworth et al. (Pfizer Inc.); JMV-390-1 (2(R)-benzyl-3-(N-hydroxycarbamoyl)propionyl-L-isoleucyl-L-leucine); ecadotril; phosphoramidon; retrothiorphan; RU-42827 (2-(mercaptomethyl)-N-(4-pyridinyl) benzenepropionamide); RU-44004 (N-(4-morpholinyl)-3-phenyl-2-(sulfanylmethyl)propionamide); SCH-32615 ((S)—N—[N-(1-carboxy-2-phenylethyl)-L-phenylalanyl]-β-alanine) and its prodrug SCH-34826 ((S)—N—[N-[1-[[(2,2-dimethyl-1,3-dioxolan-4-yl)methoxy]carbonyl]-2-phenylethyl]-L-phenylalanyl]-β-alanine); sialorphin; SCH-42495 (N-[2(S)-(acetylsulfanylmethyl)-3-(2-methylphenyl) propionyl]-L-methionine ethyl ester); spinorphin; SQ-28132 (N-[2-(mercaptomethyl)-1-oxo-3-phenylpropyl]leucine); SQ-28603 (N-[2-(mercaptomethyl)-1-oxo-3-phenylpropyl]-β-alanine); SQ-29072 (7-[[2-(mercaptomethyl)-1-oxo-3-phenylpropyl]amino]heptanoic acid); thiorphan and its prodrug racecadotril; UK-69578 (cis-4-[[[1-[2-carboxy-3-(2-methoxyethoxy)propyl]cyclopentyl]carbonyl]amino] cyclohexanecarboxylic acid); UK-447,841 (2-{1-[3-(4-chlorophenyl)propylcarbamoyl]-cyclopentylmethyl}-4-methoxybutyric acid); UK-505,749 ((R)-2-methyl-3-{1-[3-(2-methylbenzothiazol-6-yl)propylcarbamoyl] cyclopentyl}propionic acid); 5-biphenyl-4-yl-4-(3-carboxypropionylamino)-2-methylpentanoic acid and 5-biphenyl-4-yl-4-(3-carboxypropionylamino)-2-methyl-pentanoic acid ethyl ester (WO 2007/056546); daglutril [(3S,2'R)-3-{1-[2'-(ethoxycarbonyl)-4'-phenylbutyl]-cyclopentan-1-carbonylamino}-2,3,4,5-tetrahydro-2-oxo-1H-1-benzazepine-1-acetic acid] described in WO 2007/106708 to Khder et al. (Novartis AG); and combinations thereof. In a particular embodiment, the NEP inhibitor is selected from AHU-377, candoxatril, candoxatrilat, CGS-24128, phosphoramidon, SCH-32615, SCH-34826, SQ-28603, thiorphan, and combinations thereof. In a particular embodiment, the NEP inhibitor is a compound such as daglutril or CGS-26303 ([N-[2-(biphenyl-4-yl)-1(S)-(1H-tetrazol-5-yl) ethyl]amino]methylphosphonic acid), which have activity both as inhibitors of the endothelin converting enzyme (ECE) and of NEP. Other dual acting ECE/NEP compounds can also be used. The NEP inhibitor will be administered in an amount sufficient to provide from about 20-800 mg per day, with typical daily dosages ranging from 50-700 mg per day, more commonly 100-600 or 100-300 mg per day.

In one embodiment, compounds of the invention are administered in combination with a nitric oxide donor, examples of which include, but are not limited to nicorandil; organic nitrates such as pentaerythritol tetranitrate; and sydnonimines such as linsidomine and molsidomine.

In yet another embodiment, compounds of the invention are administered in combination with a non-steroidal anti-inflammatory agent (NSAID). Representative NSAIDs include, but are not limited to: acemetacin, acetyl salicylic acid, alclofenac, alminoprofen, amfenac, amiprilose, aloxiprin, anirolac, apazone, azapropazone, benorilate, benoxaprofen, bezpiperylon, broperamole, bucloxic acid, carprofen, clidanac, diclofenac, diflunisal, diftalone, enolicam, etodolac, etoricoxib, fenbufen, fenclofenac, fenclozic acid, fenoprofen, fentiazac, feprazone, flufenamic acid, flufenisal, fluprofen, flurbiprofen, furofenac, ibufenac, ibuprofen, indomethacin, indoprofen, isoxepac, isoxicam, ketoprofen, ketorolac, lofemizole, lomoxicam, meclofenamate, meclofenamic acid, mefenamic acid, meloxicam, mesalamine, miroprofen, mofebutazone, nabumetone, naproxen, niflumic acid, oxaprozin, oxpinac, oxyphenbutazone, phenylbutazone, piroxicam, pirprofen, pranoprofen, salsalate, sudoxicam, sulfasalazine, sulindac, suprofen, tenoxicam, tiopinac, tiaprofenic acid, tioxaprofen, tolfenamic acid, tolmetin, triflumidate, zidometacin, zomepirac, and combinations thereof. In a particular embodiment, the NSAID is selected from etodolac, flurbiprofen, ibuprofen, indomethacin, ketoprofen, ketorolac, meloxicam, naproxen, oxaprozin, piroxicam, and combinations thereof.

In one embodiment, compounds of the invention are administered in combination with an N-methyl d-aspartate (NMDA) receptor antagonist, examples of which include, by way of illustration and not limitation, including amantadine, dextromethorphan, dextropropoxyphene, ketamine, ketobemidone, memantine, methadone, and so forth.

In still another embodiment, compounds of the invention are administered in combination with an opioid receptor agonist (also referred to as opioid analgesics). Representative opioid receptor agonists include, but are not limited to: buprenorphine, butorphanol, codeine, dihydrocodeine, fentanyl, hydrocodone, hydromorphone, levallorphan, levorphanol, meperidine, methadone, morphine, nalbuphine, nalmefene, nalorphine, naloxone, naltrexone, nalorphine, oxycodone, oxymorphone, pentazocine, propoxyphene, tramadol, and combinations thereof. In certain embodiments, the opioid receptor agonist is selected from codeine, dihydrocodeine, hydrocodone, hydromorphone, morphine, oxycodone, oxymorphone, tramadol, and combinations thereof.

In a particular embodiment, compounds of the invention are administered in combination with a phosphodiesterase (PDE) inhibitor, particularly a PDE-V inhibitor. Representative PDE-V inhibitors include, but are not limited to, avanafil, lodenafil, mirodenafil, sildenafil (Revatio®), tadalafil (Adcirca®), vardenafil (Levitra®), and udenafil.

In another embodiment, compounds of the invention are administered in combination with a prostaglandin analog (also referred to as prostanoids or prostacyclin analogs). Representative prostaglandin analogs include, but are not limited to, beraprost sodium, bimatoprost, epoprostenol, iloprost, latanoprost, tafluprost, travoprost, and treprostinil, with bimatoprost, latanoprost, and tafluprost being of particular interest.

In yet another embodiment, compounds of the invention are administered in combination with a prostaglandin receptor agonist, examples of which include, but are not limited to, bimatoprost, latanoprost, travoprost, and so forth.

Compounds of the invention may also be administered in combination with a renin inhibitor, examples of which include, but are not limited to, aliskiren, enalkiren, remikiren, and combinations thereof.

In another embodiment, compounds of the invention are administered in combination with a selective serotonin reuptake inhibitor (SSRI). Representative SSRIs include, but are not limited to: citalopram and the citalopram metabolite desmethylcitalopram, dapoxetine, escitalopram (e.g., escitalopram oxalate), fluoxetine and the fluoxetine desmethyl metabolite norfluoxetine, fluvoxamine (e.g., fluvoxamine maleate), paroxetine, sertraline and the sertraline metabolite demethylsertraline, and combinations thereof.

In one embodiment, compounds of the invention are administered in combination with a 5-$HT_{1D}$ serotonin receptor agonist, examples of which include, by way of illustration and not limitation, triptans such as almotriptan, avitriptan, eletriptan, frovatriptan, naratriptan rizatriptan, sumatriptan, and zolmitriptan.

In one embodiment, compounds of the invention are administered in combination with a sodium channel blocker, examples of which include, by way of illustration and not limitation, carbamazepine, fosphenytoin, lamotrigine, lidocaine, mexiletine, oxcarbazepine, phenytoin, and combinations thereof.

In one embodiment, compounds of the invention are administered in combination with a soluble guanylate cyclase stimulator or activator, examples of which include, but are not limited to ataciguat, riociguat, and combinations thereof.

In one embodiment, compounds of the invention are administered in combination with a tricyclic antidepressant (TCA), examples of which include, by way of illustration and not limitation, amitriptyline, amitriptylinoxide, butriptyline, clomipramine, demexiptiline, desipramine, dibenzepin, dimetacrine, dosulepin, doxepin, imipramine, imipraminoxide, lofepramine, melitracen, metapramine, nitroxazepine, nortriptyline, noxiptiline, pipofezine, propizepine, protriptyline, quinupramine, and combinations thereof.

In one embodiment, compounds of the invention are administered in combination with a vasopressin receptor antagonist, examples of which include, by way of illustration and not limitation, conivaptan and tolvaptan.

Combined secondary therapeutic agents may also be helpful in further combination therapy with compounds of the invention. For example, compounds of the invention can be combined with a diuretic and an ARB, or a calcium channel blocker and an ARB, or a diuretic and an ACE inhibitor, or a calcium channel blocker and a statin. Specific examples include, a combination of the ACE inhibitor enalapril (in the maleate salt form) and the diuretic hydrochlorothiazide, which is sold under the mark Vaseretic®, or a combination of the calcium channel blocker amlodipine (in the besylate salt form) and the ARB olmesartan (in the medoxomil prodrug form), or a combination of a calcium channel blocker and a statin, all may also be used with the compounds of the invention. Other therapeutic agents such as $\alpha_2$-adrenergic receptor agonists and vasopressin receptor antagonists may also be helpful in combination therapy. Exemplary $\alpha_2$-adrenergic receptor agonists include clonidine, dexmedetomidine, and guanfacine.

The following formulations illustrate representative pharmaceutical compositions of the invention.

Exemplary Hard Gelatin Capsules For Oral Administration

A compound of the invention (50 g), 440 g spray-dried lactose and 10 g magnesium stearate are thoroughly blended. The resulting composition is then loaded into hard gelatin capsules (500 mg of composition per capsule). Alternately, a compound of the invention (20 mg) is thoroughly blended with starch (89 mg), microcrystalline cellulose (89 mg) and magnesium stearate (2 mg). The mixture is then passed through a No. 45 mesh U.S. sieve and loaded into a hard gelatin capsule (200 mg of composition per capsule).

Alternately, a compound of the invention (30 g), a secondary agent (20 g), 440 g spray-dried lactose and 10 g magnesium stearate are thoroughly blended, and processed as described above.

Exemplary Gelatin Capsule Formulation for Oral Administration

A compound of the invention (100 mg) is thoroughly blended with polyoxyethylene sorbitan monooleate (50 mg) and starch powder (250 mg). The mixture is then loaded into a gelatin capsule (400 mg of composition per capsule). Alternately, a compound of the invention (70 mg) and a secondary agent (30 mg) are thoroughly blended with polyoxyethylene sorbitan monooleate (50 mg) and starch powder (250 mg), and the resulting mixture loaded into a gelatin capsule (400 mg of composition per capsule).

Alternately, a compound of the invention (40 mg) is thoroughly blended with microcrystalline cellulose (Avicel PH 103; 259.2 mg) and magnesium stearate (0.8 mg). The mixture is then loaded into a gelatin capsule (Size #1, White, Opaque) (300 mg of composition per capsule).

Exemplary Tablet Formulation For Oral Administration

A compound of the invention (10 mg), starch (45 mg) and microcrystalline cellulose (35 mg) are passed through a No. 20 mesh U.S. sieve and mixed thoroughly. The granules so produced are dried at 50-60° C. and passed through a No. 16 mesh U.S. sieve. A solution of polyvinylpyrrolidone (4 mg as a 10% solution in sterile water) is mixed with sodium carboxymethyl starch (4.5 mg), magnesium stearate (0.5 mg), and talc (1 mg), and this mixture is then passed through a No. 16 mesh U.S. sieve. The sodium carboxymethyl starch, magnesium stearate and talc are then added to the granules. After mixing, the mixture is compressed on a tablet machine to afford a tablet weighing 100 mg.

Alternately, a compound of the invention (250 mg) is thoroughly blended with microcrystalline cellulose (400 mg), silicon dioxide fumed (10 mg), and stearic acid (5 mg). The mixture is then compressed to form tablets (665 mg of composition per tablet).

Alternately, a compound of the invention (400 mg) is thoroughly blended with cornstarch (50 mg), croscarmellose sodium (25 mg), lactose (120 mg), and magnesium stearate (5 mg). The mixture is then compressed to form a single-scored tablet (600 mg of composition per tablet).

Alternately, a compound of the invention (100 mg) is thoroughly blended with cornstarch (100 mg) with an aqueous solution of gelatin (20 mg). The mixture is dried and ground to a fine powder. Microcrystalline cellulose (50 mg) and magnesium stearate (5 mg) are then admixed with the gelatin formulation, granulated and the resulting mixture compressed to form tablets (100 mg of the compound of the invention per tablet).

Exemplary Suspension Formulation for Oral Administration

The following ingredients are mixed to form a suspension containing 100 mg of the compound of the invention per 10 mL of suspension:

| Ingredients | Amount | |
|---|---|---|
| Compound of the invention | 1.0 | g |
| Fumaric acid | 0.5 | g |
| Sodium chloride | 2.0 | g |
| Methyl paraben | 0.15 | g |
| Propyl paraben | 0.05 | g |
| Granulated sugar | 25.5 | g |
| Sorbitol (70% solution) | 12.85 | g |
| Veegum ® K (magnesium aluminum silicate) | 1.0 | g |
| Flavoring | 0.035 | mL |
| Colorings | 0.5 | mg |
| Distilled water | q.s. to 100 | mL |

Exemplary Liquid Formulation for Oral Administration

A suitable liquid formulation is one with a carboxylic acid-based buffer such as citrate, lactate and maleate buffer solutions. For example, a compound of the invention (which may be pre-mixed with DMSO) is blended with a 100 mM ammonium citrate buffer and the pH adjusted to pH 5, or is blended with a 100 mM citric acid solution and the pH adjusted to pH 2. Such solutions may also include a solubilizing excipient such as a cyclodextrin, for example the solution may include 10 wt % hydroxypropyl-3-cyclodextrin.

Other suitable formulations include a 5% NaHCO$_3$ solution, with or without cyclodextrin.

Exemplary Injectable Formulation for Administration by Injection

A compound of the invention (0.2 g) is blended with 0.4 M sodium acetate buffer solution (2.0 mL). The pH of the resulting solution is adjusted to pH 4 using 0.5 N aqueous hydrochloric acid or 0.5 N aqueous sodium hydroxide, as necessary, and then sufficient water for injection is added to provide a total volume of 20 mL. The mixture is then filtered through a sterile filter (0.22 micron) to provide a sterile solution suitable for administration by injection.

Exemplary Compositions for Administration by Inhalation

A compound of the invention (0.2 mg) is micronized and then blended with lactose (25 mg). This blended mixture is then loaded into a gelatin inhalation cartridge. The contents of the cartridge are administered using a dry powder inhaler, for example.

Alternately, a micronized compound of the invention (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 µm. The micronized composition is then loaded into metered-dose inhaler cartridges containing pressurized 1,1,1,2-tetrafluoroethane in an amount sufficient to provide about 10 µg to about 500 µg of the compound of the invention per dose when administered by the inhaler.

Alternately, a compound of the invention (25 mg) is dissolved in citrate buffered (pH 5) isotonic saline (125 mL). The mixture is stirred and sonicated until the compound is dissolved. The pH of the solution is checked and adjusted, if necessary, to pH 5 by slowly adding aqueous 1 N NaOH. The solution is administered using a nebulizer device that provides about 10 µg to about 500 µg of the compound of the invention per dose.

EXAMPLES

The following Preparations and Examples are provided to illustrate specific embodiments of the invention. These specific embodiments, however, are not intended to limit the scope of the invention in any way unless specifically indicated.

The following abbreviations have the following meanings unless otherwise indicated and any other abbreviations used herein and not defined have their standard, generally accepted meaning:

AcOH acetic acid
BOC t-butoxycarbonyl (—C(O)OC(CH$_3$)$_3$)
(BOC)$_2$O di-t-butyl dicarbonate
Bzl benzyl
DCC dicyclohexylcarbodiimide
DCM dichloromethane or methylene chloride
DIPEA N,N-diisopropylethylamine
DMAP 4-dimethylaminopyridine
DMF N,N-dimethylformamide
DMSO dimethyl sulfoxide
Et$_3$N triethylamine
Et$_2$O diethyl ether
EtOAc ethyl acetate
EtOH ethanol
HATU N,N,N',N'-tetramethyl-O-(7-azabenzotriazol-1-yl) uronium hexafluorophosphate
LiHMDS lithium hexamethyl disilazide
MeCN acetonitrile
MeOH methanol
MTBE methyl t-butyl ether
NaHMDS sodium hexamethyldisilazide
Pd(dppf)$_2$Cl$_2$ 1,1-bis(diphenylphosphino) ferrocene palladium chloride
PE petroleum ether (better known as hexanes)
TFA trifluoroacetic acid
THF tetrahydrofuran Unless noted otherwise, all materials, such as reagents, starting materials and solvents, were purchased from commercial suppliers (such as Sigma-Aldrich, Fluka Riedel-de Haën, and the like) and were used without further purification.

Reactions were run under nitrogen atmosphere, unless noted otherwise. The progress of reactions were monitored by thin layer chromatography (TLC), analytical high performance liquid chromatography (anal. HPLC), and mass spectrometry, the details of which are given in specific examples. Solvents used in analytical HPLC were as follows: solvent A was 98% $H_2O$/2% MeCN/1.0 mL/L TFA; solvent B was 90% MeCN/10% $H_2O$/1.0 mL/L TFA.

Reactions were worked up as described specifically in each preparation for example; commonly reaction mixtures were purified by extraction and other purification methods such as temperature-, and solvent-dependent crystallization, and precipitation. In addition, reaction mixtures were routinely purified by preparative HPLC, typically using Microsorb C18 and Microsorb BDS column packings and conventional eluents. Progress of reactions was typically measured by liquid chromatography mass spectrometry (LCMS). Characterization of isomers were done by Nuclear Overhauser effect spectroscopy (NOE). Characterization of reaction products was routinely carried out by mass and $^1$H-NMR spectrometry. For NMR measurement, samples were dissolved in deuterated solvent ($CD_3OD$, $CDCl_3$, or $DMSO-d_6$), and $^1$H-NMR spectra were acquired with a Varian Gemini 2000 instrument (400 MHz) under standard observation conditions. Mass spectrometric identification of compounds was typically conducted using an electrospray ionization method (ESMS) with an Applied Biosystems (Foster City, Calif.) model API 150 EX instrument or an Agilent (Palo Alto, Calif.) model 1200 LC/MSD instrument.

Preparation 1: Oxodiperoxymolybdenum(pyridine)(hexamethylphosphorictriamide)

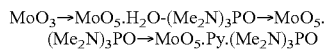

Molybdenum oxide ($MoO_3$; 30 g, 0.2 mol) and 30% hydrogen peroxide (150 mL) were combined, with stirring. The reaction vessel was placed in an oil bath equilibrated at 40° C. and heated until the internal temperature reached 35° C. The heating bath was then removed and replaced by a water bath to control the mildly exothermic reaction so that an internal temperature of 35-40° C. was maintained. After the initial exothermic period (~30 minutes), the reaction vessel was returned to the 40° C. oil bath and stirred for a total of 3.5 hours to form a yellow solution with a small amount of suspended white solid. After cooling to 20° C., the solution was filtered and the resulting yellow filtrate was cooled to 10° C. (ice bath with stirring) and hexamethylphosphoric triamide (($Me_2N)_3PO$; HMPA; 37.3 g, 0.2 mol) was added dropwise over 5 minutes, resulting in the formation of a yellow crystalline precipitate. Stirring was continued for a total of 15 minutes at 10° C., and the product was filtered and pressed dry. After 30 minutes under vacuum, the filter cake was combined with MeOH (20 mL) and stirred at 40° C. Additional MeOH was slowly added until the solids dissolved. The saturated solution was cooled in the refrigerator, yielding a yellow solid (appeared as needles). The solid mass was physically broken, filtered and washed with cold MeOH (20-30 mL) to yield oxodiperoxymolybdenum (aqua) (hexamethylphosphoric triamide) ($MoO_5.H_2O.HMPA$, 46-50 g).

$MoO_5.H_2O.HMPA$ was dried over phosphorus oxide in a vacuum desiccator, shielded from the light, for 24 hours at 0.2 mm Hg to yield a somewhat hygroscopic yellow solid, $MoO_5.HMPA$. $MoO_5.HMPA$ (36.0 g, 0.1 mol) was dissolved in THF (150 mL) and the solution was filtered to remove any precipitate. The filtrate was then stirred at 20° C. while dry pyridine (8.0 g, 0.1 mol) was added over 10 minutes. The crystalline, yellow product was collected, washed with dry THF (25 mL) and anhydrous ether (200 mL) and dried in a vacuum desiccator (1 hour, 0.2 mm Hg) to yield the title compound, oxodiperoxymolybdenum(pyridine)(hexamethylphosphoric triamide) ($MoO_5.Py.HMPA$) as a finely divided yellow solid (36-38 g).

Preparation 2: (2R,4R)-4-Amino-5-biphenyl-4-yl-2-hydroxypentanoic Acid Ethyl Ester (Compound 7) and (2R,4S)-4-Amino-5-biphenyl-4-yl-2-hydroxypentanoic Acid Ethyl Ester (Compound 9)

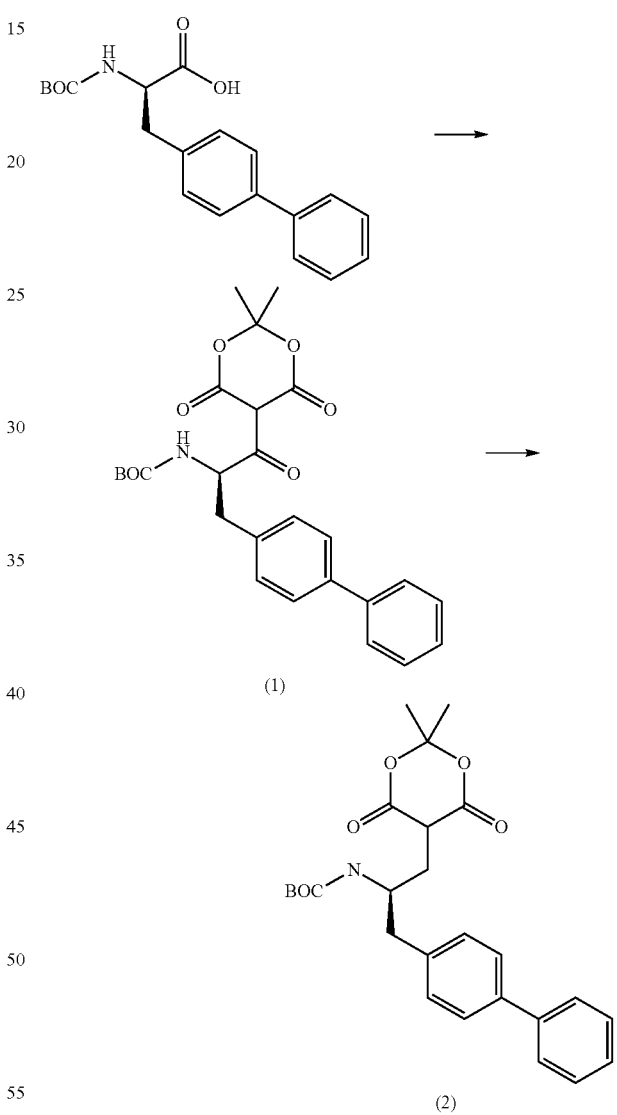

To a stirred solution of (R)-3-biphenyl-4-yl-2-t-butoxycarbonylaminopropionic acid (50 g, 146.5 mmol), Meldrum's acid (23.3 g, 161.1 mmol) and DMAP (27.8 g, 227 mmol) in anhydrous DCM (500 mL) was added a solution of DCC (33.3 g, 161.1 mmol) in anhydrous DCM (200 mL) over 1 hour at −5° C. under nitrogen. The mixture was stirred at −5° C. for 8 hours, then refrigerated overnight, during which tiny crystals of dicyclohexylurea precipitated. After filtration the mixture was washed with 5% $KHSO_4$ (4×200 mL), saturated aqueous NaCl (1×200 mL) and dried over MgSO₄ overnight. The resulting solution was evaporated to give the crude Compound 1 (68 g) as a light yellow solid). LC-MS: [M⁺Na]:490, [2M⁺Na]:957.

To a solution of crude Compound 1 (68 g, 146.5 mmol) in anhydrous DCM (1000 mL) was added AcOH (96.8 g, 1.6 mol) at −5° C. under nitrogen. The resulting mixture was stirred at −5° C. for 0.5 hours, then NaBH₄ (13.9 g, 366 mmol) was added in small portions over 2 hours. After stirring for another hour at −5° C., saturated aqueous NaCl (300 mL) was added. The organic layer was washed with saturated aqueous NaCl (2×300 mL) then water (2×300 mL), dried over MgSO₄, filtered, and evaporated to give the crude Compound 2, which was further purified by chromatography (hexanes:EtOAc=5:1) to give purified Compound 2 (46 g) as a light yellow solid. LC-MS: [M⁺Na]:476, [2M⁺Na]:929.

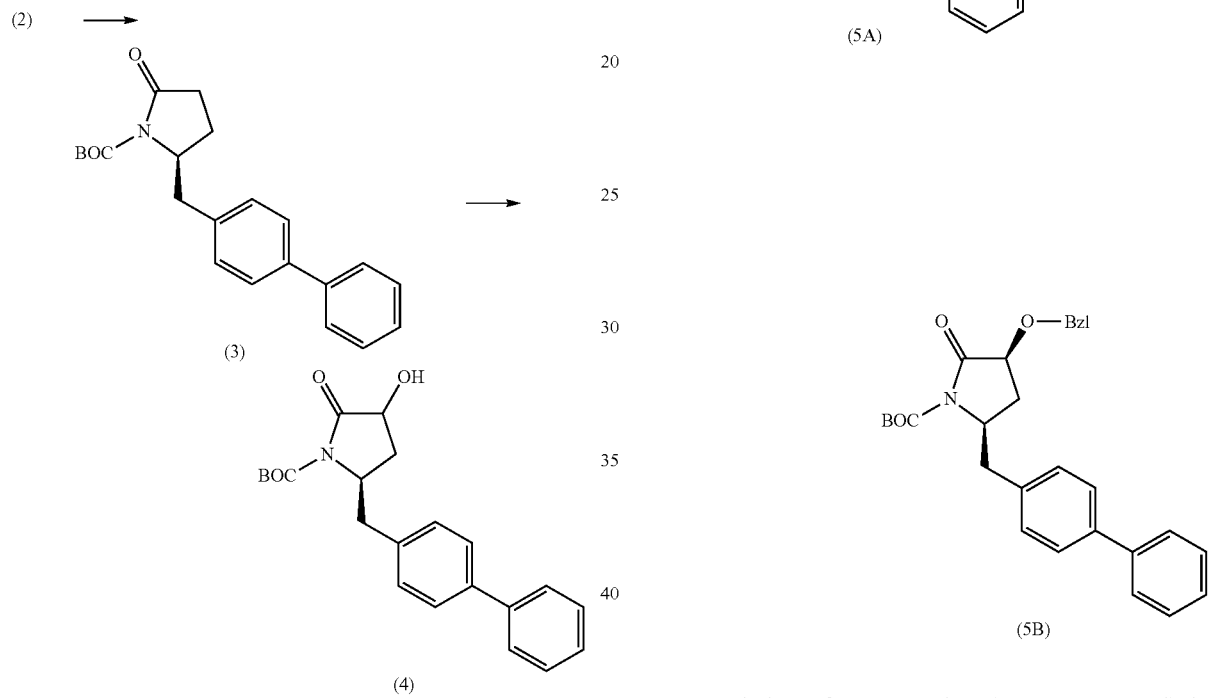

A stirred solution of purified Compound 2 (46 g, 101 mmol) in anhydrous toluene (300 mL) was heated to reflux under nitrogen for 3 hours. After evaporation of the solvent, the residue was purified by chromatography (hexanes:EtOAc=10:1) to yield Compound 3 (27 g) as a light yellow solid.

LC-MS: [M⁺Na]:374, [2M⁺Na]:725; 1H NMR (300 MHz, CDCl₃): δ7.64-7.62 (m, 4H), 7.51-7.46 (m, 2H), 7.42-7.39 (m, 1H), 7.39-7.30 (m, 2H), 4.50-4.43 (m, 1H), 3.27-3.89 (m, 1H), 2.88-2.80 (m, 1H), 2.48-2.42 (m, 2H), 2.09-1.88 (m, 2H), 1.66 (s, 9H).

To a stirred solution of Compound 3 (4.4 g, 12.4 mmol) in anhydrous THF (70 mL) was added a solution of 1 M LiHMDS in THF (28 mL) over 15 minutes at −65° C. under nitrogen. After stirring for 3 hours at −65° C., oxodiperoxymolybdenum(pyridine)(hexamethylphosphorictriamide) (9 g, 18.6 mmol) was added. The mixture was stirred for another 2 hours at −35° C., then saturated aqueous Na₂S₂O₃ (60 mL) was added. The organic layer was collected and washed with saturated aqueous NH₄Cl (60 mL×3) and saturated aqueous NaCl (60 mL×2), then dried over Na₂SO₄, and the solvent was removed under reduced pressure to yield the crude product which was further purified by chromatography (hexanes:EtOAc=5:1) to yield Compound 4 as a white solid (1.8 g). LC-MS: [2M+Na]:757.

To a solution of Compound 4 (1.8 g, 5.0 mmol) in anhydrous DCM (50 mL) was added DMAP (122 mg, 1 mmol) and Et₃N (1.5 g, 14.9 mmol) at 0° C. under nitrogen. After stirring for 0.5 hour at 0° C., benzyl chloride (1.0 g, 7.4 mmol) was added over 15 minutes. The mixture was stirred for an additional 2 hours at 0° C., then saturated aqueous NaHCO₃ (50 mL) was added. The organic layer was collected and washed with saturated aqueous NaHCO₃ (50 mL×2) and saturated aqueous NaCl (50 mL×1), then dried over Na₂SO₄. The solids were filtered out and the filtrate was concentrated to yield the crude product which was further purified by chromatography (hexanes:EtOAc=4:1) to yield Compound 5A (471 mg) and Compound 5B (883 mg) as white solids. LC-MS: [M+Na]:494; [2M+Na]:965.

Compound 5A: ¹H NMR (300 MHz, CDCl₃): δ (ppm)=8.02 (m, 2H), 7.57-7.25 (m, 12H), 5.42 (m, 1H), 4.50 (m, 1H), 3.26-3.21 (m, 1H), 2.90 (m, 1H), 2.58 (m, 1H), 2.15-2.05 (m, 1H), 1.62 (m, 9H)

Compound 5B: ¹H NMR (300 MHz, CDCl₃): δ (ppm)=8.06 (m, 2H), 7.58-7.18 (m, 12H), 5.53-5.41 (m, 1H), 4.39 (m, 1H), 3.57-3.54 (m, 1H), 2.87-2.80 (m, 1H), 2.48-2.44 (m, 1H), 1.98 (m, 1H), 1.63 (m, 9H).

(5A) →

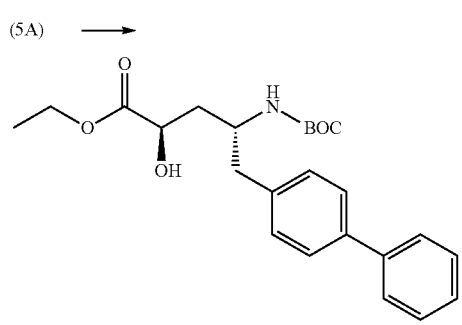
(6)

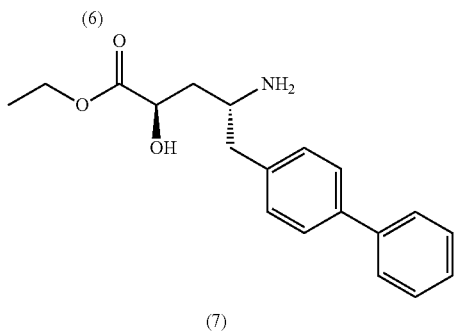
(7)

To a stirred solution of Compound 5A (471 mg, 1 mmol) in anhydrous EtOH (10 mL) was added anhydrous K$_2$CO$_3$ (691 mg, 5 mmol) at room temperature under nitrogen. After stirring for 20 hours at room temperature, the solids were filtered out. To the filtrate was added water (30 mL), DCM (30 mL) and saturated aqueous NaCl (5 mL). The aqueous layer was separated and extracted with DCM (30 mL×3). The combined organic layers were washed with saturated aqueous NaCl (50 mL), dried over Na$_2$SO$_4$, and concentrated to yield the crude product which was further purified by chromatography (hexanes:EtOAc=6:1) to yield Compound 6 as a white solid (275 mg). LC-MS: [M+Na]:436, [2M+Na]:849.

To EtOH (5 mL) was added acetyl chloride (685 mg) at −30° C. After stirring for 1 hour at −30° C., a solution of Compound 6 (275 mg, 665 µmol) in anhydrous EtOH (5 mL) was added. The mixture was heated to 25° C. and stirred for 3 hours at 25° C. After evaporation of the solvent, the residue was washed with cold anhydrous Et$_2$O (10 mL) to yield Compound 7 as a white solid HCl salt (207 mg). LC-MS: [M+H]:314, [2M+Na]:649.

$^1$H NMR (300 MHz, CDCl$_3$): δ (ppm)=7.99 (m, 3H), 7.66-7.64 (m, 4H), 7.48-7.35 (m, 5H), 6.08 (m, 1H), 4.21 (m, 1H), 4.09-4.05 (m, 2H), 3.52 (m, 1H), 2.97-2.95 (m, 2H), 1.89-1.87 (m, 2H), 1.19-1.14 (m, 3H).

(5B) →

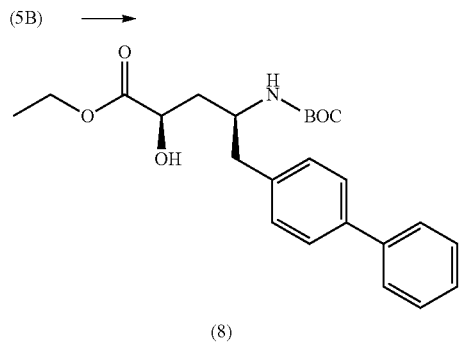
(8)

→

-continued

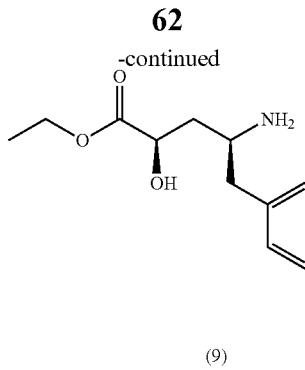
(9)

To a stirred solution of Compound 5B (883 mg, 1.9 mmol) in anhydrous EtOH (15 mL) was added anhydrous K$_2$CO$_3$ (1293 mg, 9.4 mmol) at room temperature under nitrogen. After stirring for 20 hours at room temperature, the solids were filtered out. To the filtrate was added water (30 mL), DCM (30 mL) and saturated aqueous NaCl (5 mL). The aqueous layer was separated and extracted with DCM (30 mL×3). The combined organic layers were washed with saturated aqueous NaCl (50 mL), dried over Na$_2$SO$_4$, and concentrated to yield the crude product which was further purified by chromatography (hexanes:EtOAc=6:1) to yield Compound 8 as a white solid (524 mg). LC-MS: [M+Na]: 436, [2M+Na]:849.

To EtOH (8 mL) was added acetyl chloride (1300 mg) at −30° C. After stirring for 1 hour at −30° C., a solution of Compound 8 (524 mg, 1.3 mmol) in anhydrous EtOH (8 mL) was added. The mixture was heated to 25° C. and stirred for 3 hours at 25° C. After evaporation of the solvent, the residue was washed with cold anhydrous Et$_2$O (10 mL) to yield Compound 9 as a white solid HCl salt (395 mg). LC-MS: [M+H]:314, [2M+Na]:649.

$^1$H NMR (300 MHz, CDCl$_3$): δ (ppm)=8.14 (m, 3H), 7.66-7.62 (m, 4H), 7.47-7.31 (m, 5H), 5.87-5.85 (m, 1H), 4.34 (m, 1H), 4.08-4.00 (m, 2H), 3.48 (m, 1H), 3.09 (m, 1H), 2.85-2.81 (m, 1H), 1.88 (m, 1H), 1.76 (m, 1H), 1.15-1.10 (m, 3H).

Preparation 3: (S)-2-(4-Bromobenzyl)-5-oxopyrrolidine-1-carboxylic Acid t-Butyl Ester

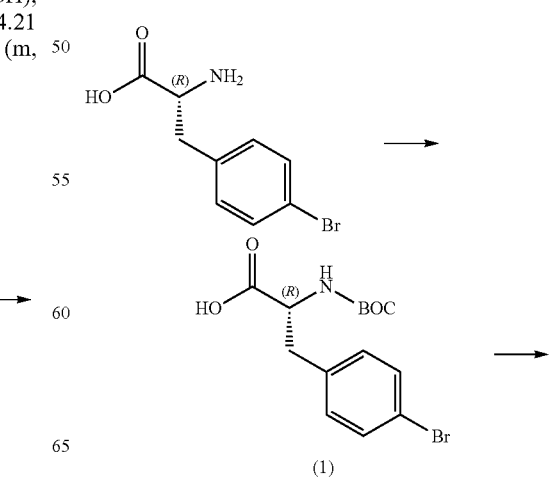
(1)

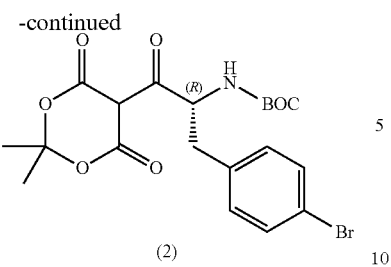

(2)

To a solution of (R)-2-amino-3-(4-bromophenyl)propionic acid (50 g, 0.2 mol) in MeCN (700 mL) was added a solution of NaOH (16.4 g, 0.4 mol) in water (700 mL) at −5° C. After stirring for 10 minutes, a solution of (BOC)₂O (44.7 g, 0.2 mol) in MeCN (100 mL) was added. The mixture was warmed to room temperature and stirred overnight. After the evaporation of the MeCN, the residue was diluted with DCM (800 mL) and acidified with 1 M HCl to pH 2 at −5° C. The aqueous was extracted with DCM (3×200 mL). The combined organic layers were washed with saturated aqueous NaCl (500 mL), dried over Na₂SO₄ and concentrated to yield Compound 1 (66.5 g) as a white solid. LC-MS: 366 (M+Na), 709 (2M+Na).

To a solution of Compound 1 (66.5 g, 193 μmol), Meldrum's acid (33.4 g, 232 mmol) and DMAP (37.7 g, 309 mmol) in anhydrous DCM (600 mL), was added dropwise a solution of DCC (47.9 g, 232 mmol) in anhydrous DCM (200 mL) over 1 hour at −5° C. under nitrogen. The mixture was stirred at −5° C. for 8 hours, then refrigerated overnight. Crystals of dicyclohexylurea were observed. The mixture was filtered, washed with 5% KHSO₄ (5×200 mL) and saturated aqueous NaCl (200 mL), then dried over anhydrous MgSO₄ under refrigeration overnight. The solution was then evaporated to yield crude Compound 2 (91 g) as a light yellow solid. LC-MS: 492(M+Na), 961(2M+Na).

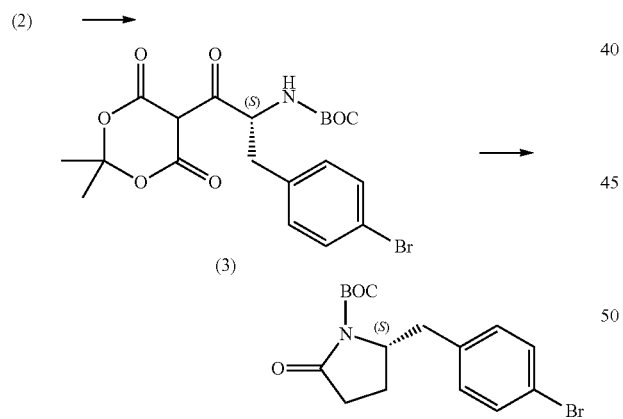

To a solution of crude Compound 2 (91 g, 193 mmol) in anhydrous DCM (1 L) was added AcOH (127.5 g, 2.1 mol) at −5° C. under nitrogen. The mixture was stirred at −5° C. for 30 minutes, then NaBH₄ (18.3 g, 483 mmol) was added in small portions over 1 hour. After stirring for another 1 hour at −5° C., saturated aqueous NaCl (500 mL) was added. The organic layer was washed with saturated aqueous NaCl (2×300 mL) and water (2×300 mL), dried over MgSO₄, filtered, and concentrated to yield the crude product, which was further purified by washing with Et₂O to yield Compound 3 (68 g) as a light yellow solid. LC-MS: 478 (M+Na), 933 (2M+Na).

A solution of Compound 3 (68 g, 149 mmol) in anhydrous toluene (500 mL) was refluxed under nitrogen for 3 hours. After evaporation of the solvent, the residue was purified by chromatography (hexanes:EtOAc=10:1) to yield the title compound (38 g) as a light yellow oil. LC-MS: 376 (M+Na), 729 (2M+Na).

Preparation 4: (2R,4R)-4-Amino-5-(3'-chlorobiphenyl-4-yl)-2-hydroxypentanoic Acid Ethyl Ester

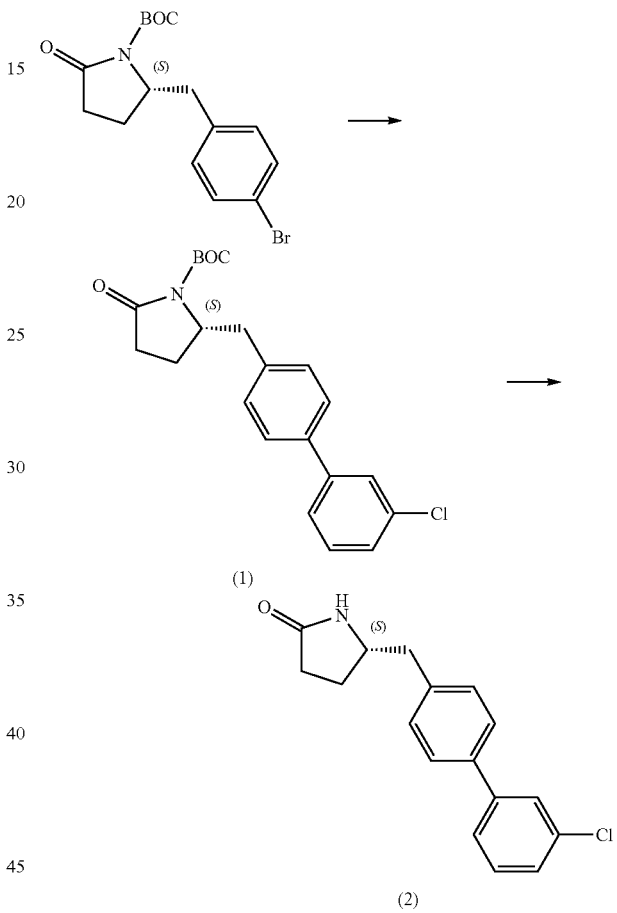

To a solution of (S)-2-(4-bromobenzyl)-5-oxopyrrolidine-1-carboxylic acid t-butyl ester (15 g, 43 mmol) in 1,4-dioxane (600 mL) was added 3-chlorophenylboronic acid (8 g, 51 mmol) and Pd(dppf)₂Cl₂ (3.1 g, 4.2 mmol) at room temperature under nitrogen. After stirring for 10 minutes, a solution of K₂CO₃ (11.7 g, 85 mmol) in water (60 mL) was added. The mixture was heated to 60° C. and stirred overnight. After evaporation of the solvent, water (200 mL) was added and extracted with EtOAc (3×200 mL). The combined organic layers were washed with saturated aqueous NaCl (400 mL), dried over Na₂SO₄, and concentrated to yield the crude product which was further purified by column chromatography (hexanes:EtOAc=6:1) to yield Compound 1 (15 g) as a light yellow solid. LC-MS: 408 (M+Na).

To a solution of Compound 1 (15 g, 0.039 mol) in anhydrous DCM (250 mL) was added TFA (20 mL, 270 mmol) at −5° C. under nitrogen. The mixture was warmed to room temperature and stirred overnight. After evaporation of the solvent, the residue was diluted with EtOAc (300 mL), then washed with saturated aqueous NaHCO₃ (3×200 mL), water (200 mL), and saturated aqueous NaCl (250 mL), then dried over Na₂SO₄ and concentrated to yield crude Compound 2 (11 g) as a light yellow solid. LC-MS: 286 [M+H].

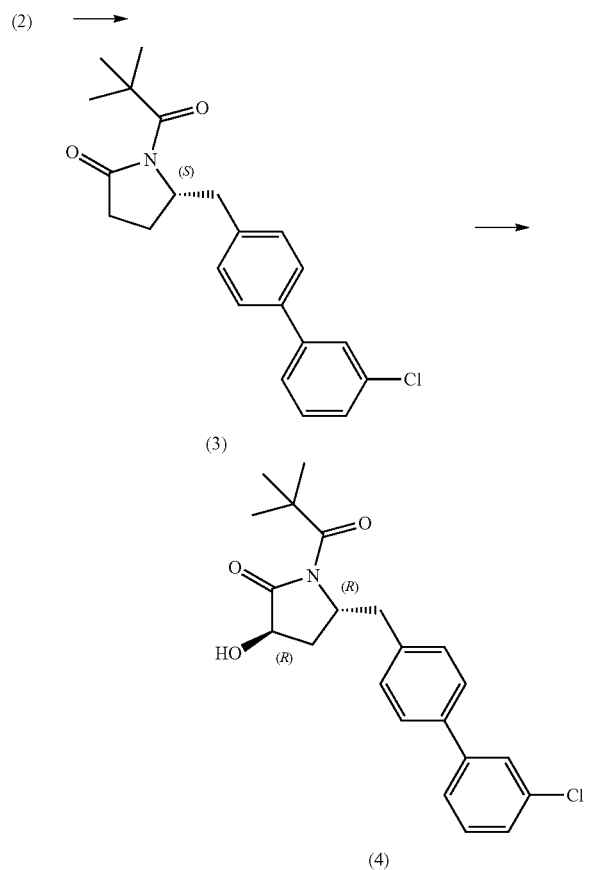

To a solution of NaH (2.3 g, 98 mmol) in anhydrous THF (200 mL) was added dropwise a solution of Compound 2 (11 g, 39 mmol) in anhydrous THF (100 mL) over 30 minutes at 0° C. under nitrogen. The mixture was warmed to room temperature and stirred for 2 hours. After cooling to 0° C., pivaloyl chloride (6 g, 51 mmol) was added dropwise over 30 minutes. The mixture was warmed to room temperature and stirred overnight. The reaction was quenched with saturated aqueous NH₄Cl (200 mL) and extracted with EtOAc (3×200 mL). The combined organic layers were washed with saturated aqueous NaCl (300 mL), dried over MgSO₄, filtered, and concentrated to yield the crude product which was further purified by chromatography (hexanes: EtOAc=25:1) to yield Compound 3 (10.5 g) as a light yellow solid. LC-MS: 391 (M+Na).

To a solution of Compound 3 (10.5 g, 29 mmol) in anhydrous THF (120 mL) was added dropwise NaHMDS (29 mL, 58 mmol) over 30 minutes at −78° C. under nitrogen. After stirring at −78° C. for 90 minutes, a solution of (+)-(8,8-dichlorocamphorylsulfonyl)-oxaziridine (15.6 g, 52 mmol) was added dropwise over 30 minutes. After stirring at −78° C. for 2 hours, the reaction was quenched with saturated NH₄Cl (400 mL) and extracted with EtOAc (3×300 mL). The combined organic layers were washed with saturated aqueous NaCl (300 mL), dried over MgSO₄, filtered, and concentrated to give the crude product which was further purified by chromatography (hexanes: EtOAc=15:1) to yield the title compound (9.6 g) as a light yellow solid. LC-MS: 408 (M+Na).

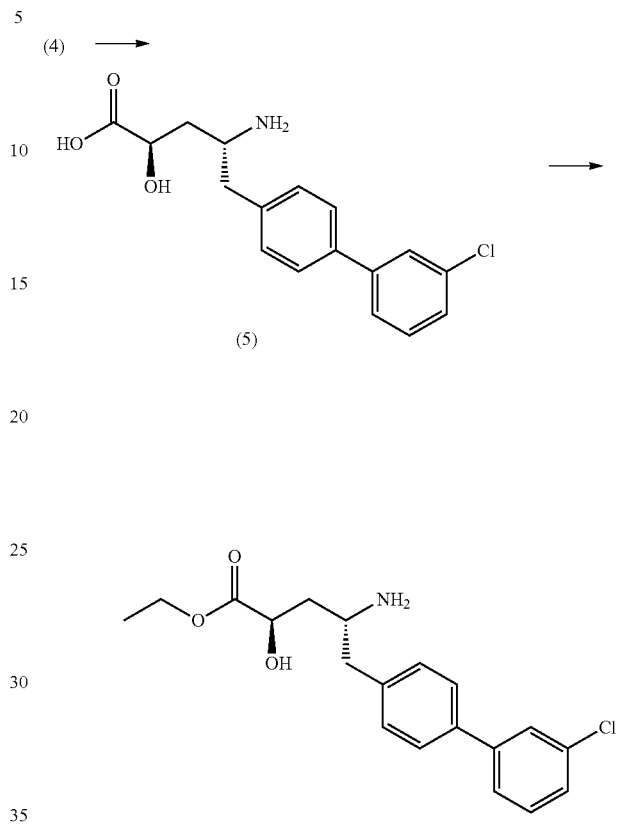

A solution of Compound 4 (9.6 g, 25 mmol) in concentrated HCl (81 mL, 81 mmol) was heated at 100° C. for 16 hours. The mixture was then concentrated to give the crude product which was further purified by washing with Et₂O to yield Compound 5 (5.7 g) as a light yellow solid HCl salt. LC-MS: 320 (M+H).

To a solution of Compound 5 ((5.7 g, 18 mmol) in EtOH (10 mL) was added 8M HCl in EtOH (120 mL, 960 mmol) at room temperature. The mixture was heated at 50° C. for 16 hours. After concentration, the crude product was further purified by washing with Et₂O to yield the title compound (2.1 g) as a light yellow solid HCl salt. LC-MS: 348 (M+H).

Preparation 5: (2R,4R)-4-Amino-5-(3'-chlorobiphenyl-4-yl)-2-hydroxypentanoic Acid

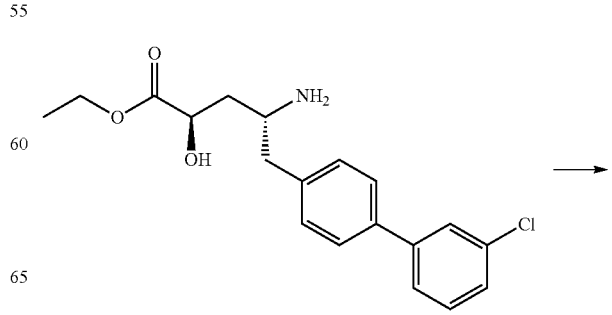

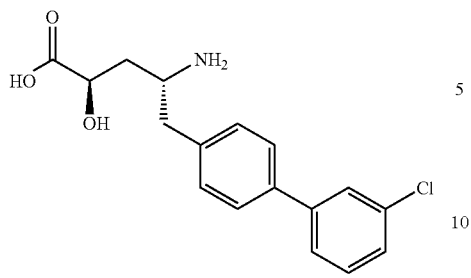

1 M aqueous HCl (2.0 mmol) was added to (2R,4R)-4-amino-5-(3'-chlorobiphenyl-4-yl)-2-hydroxypentanoic acid ethyl ester (150.0 mg, 431 μmol) and the mixture was stirred at 100° C. for 2 hours. The mixture was concentrated under vacuum for 3 hours and the residue was purified by reverse phase preparative HPLC to yield the title compound (117 mg) as a white solid.

Preparation 6: (2R,4R)-5-(3'-Chlorobiphenyl-4-yl)-2-hydroxy-4-(oxalylamino)pentanoic Acid Ethyl Ester

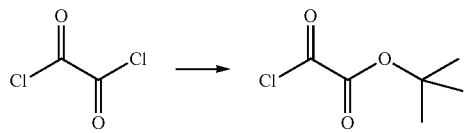

t-Butanol (765 μL, 8.0 mmol) was added dropwise to a solution of oxalyl dichloride (1.0 mL, 12.0 mmol) in DCM (5 mL) at 0° C. The mixture was stirred at room temperature for 1 hour then concentrated in vacuo to yield chloro-oxo-acetic acid t-butyl ester as a clear colorless liquid (1.1 g). A 1 M solution in DCM was prepared by dissolving the liquid (1.1 g, 6.7 mmol) in DCM (6.7 mL).

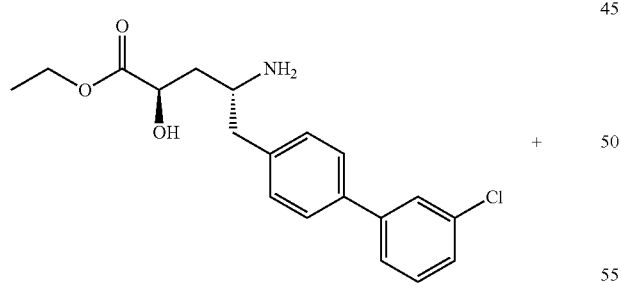

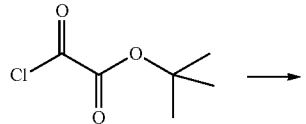

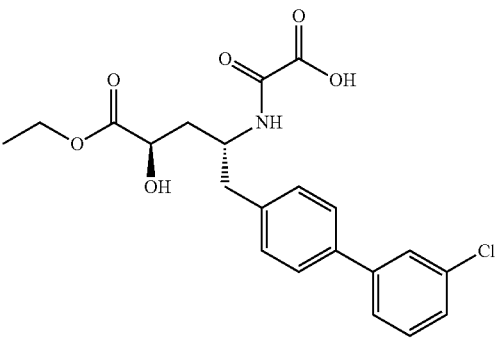

DIPEA (3.0 mL, 17.2 mmol) was added to a solution of (2R,4R)-4-amino-5-(3'-chlorobiphenyl-4-yl)-2-hydroxypentanoic acid ethyl ester (2.0 g, 5.8 mmol) in DCM (20 mL) at 0° C. A 1 M solution of chloro-oxo-acetic acid t-butyl ester in DCM (6.3 mL, 6.3 mmol) was added dropwise and the resulting mixture was stirred at room temperature for 15 minutes. The mixture was concentrated in vacuo to yield a clear brown liquid (1.4 g, 2.9 mmol). DCM (3.0 mL) and TFA (3.0 mL) were added and the resulting mixture was stirred at room temperature for 1 hour. The mixture was then concentrated in vacuo to yield a brown liquid, which was purified (Interchim C18 column chromatography, 10 g column using 40-95% MeCN in H$_2$O with 0.05% TFA) to yield the title compound as a white solid (820 mg).

Preparation 7: (2R,4R)-4-Amino-5-(2',5'-dichlorobiphenyl-4-yl)-2-hydroxypentanoic Acid Ethyl Ester -continued

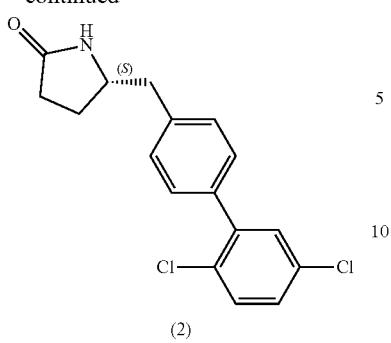

(2)

To a solution of (S)-2-(4-bromobenzyl)-5-oxopyrrolidine-1-carboxylic acid t-butyl ester (33.5 g, 95 mmol) in 1,4-dioxane (1.2 L) was added 2,5-dichlorophenylboronic acid (21.7 g, 114 mmol) and Pd(dppf)$_2$Cl$_2$ (3.5 g, 4.7 mmol) at room temperature under nitrogen. After stirring for 10 minutes, a solution of K$_2$CO$_3$ (26.1 g, 189 mmol) in water (120 mL) was added. The mixture was heated to 60° C. and stirred overnight. After evaporation of the solvent, water (400 mL) was added and extracted with EtOAc (3×400 mL). The combined organic layers were washed with saturated aqueous NaCl (500 mL), dried over anhydrous Na$_2$SO$_4$, and concentrated to yield the crude product which was further purified by column chromatography (hexanes:EtOAc=6:1) to yield Compound 1 (35.8 g) as a light yellow solid. LC-MS: 442 [M+Na].

To a solution of Compound 1 (35.8 g, 85 mmol) in anhydrous DCM (300 mL) was added TFA (30 mL, 405 mmol) at −5° C. under nitrogen. The mixture was warmed to room temperature and stirred overnight. After evaporation of the solvent, the residue was diluted with EtOAc (500 mL), then washed with saturated aqueous NaHCO$_3$ (3×300 mL), water (200 mL), and saturated aqueous NaCl (250 mL), then dried over Na$_2$SO$_4$ and concentrated to yield crude Compound 2 (26 g) as a light yellow solid. LC-MS: 320 [M+H].

(2) →

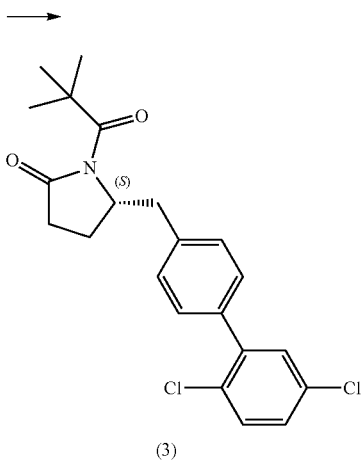

(3)

-continued

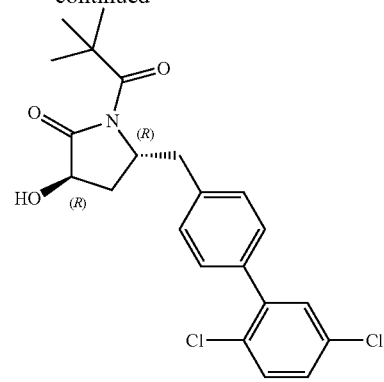

(4)

To a solution of Compound 2 (26 g, 81 mmol) in anhydrous THF (500 mL) was added dropwise n-butyllithium in hexane (39 mL, 97 mmol) over 1 hour at −78° C. under nitrogen. After stirring at −78° C. for 2 hours, the reaction was quenched by adding pivaloyl chloride (12.7 g, 105 mmol) dropwise over 30 minutes. After stirring at −78° C. for 2 hours, the reaction was quenched with saturated aqueous NH$_4$Cl (200 mL) and extracted with EtOAc (3×200 mL). The combined organic layers were washed with saturated aqueous NaCl (300 mL), dried over anhydrous MgSO$_4$, filtered and concentrated to yield the crude product which was further purified by chromatography (hexanes:EtOAc=25:1) to yield Compound 3 (33 g) as a light yellow solid. LC-MS: 426 [M+Na].

To a solution of Compound 3 (10 g, 0.025 mol) in anhydrous THF (120 mL) was added dropwise NaHMDS (18.6 mL, 37 mmol) over 30 minutes at −78° C. under nitrogen. After stirring at −78° C. for 2 hours, a solution of (+)-(8,8-dichlorocamphorylsulfonyl)-oxaziridine (11.1 g, 37 mmol) in THF (80 mL) was added dropwise over 30 minutes. After stirring at −78° C. for 2 hours, the reaction was quenched with saturated aqueous NH$_4$Cl (500 mL) and extracted with EtOAc (3×300 mL). The combined organic layers were washed with saturated aqueous NaCl (300 mL), dried over MgSO$_4$, filtered and concentrated to yield the crude product which was further purified by chromatography (hexanes:EtOAc=15:1) to yield Compound 4 (4.2 g) as a light yellow oil. LC-MS: 442 [M+Na].

(4) →

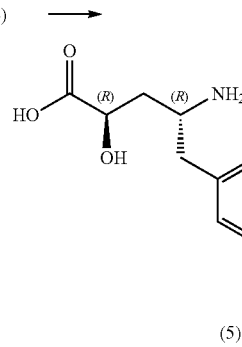

(5)

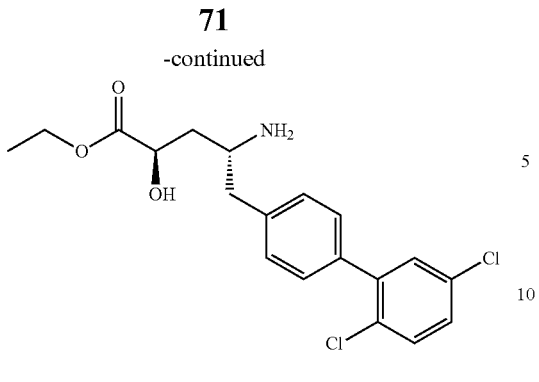

A solution of Compound 4 (4.2 g, 10 mmol) in concentrated HCl (80 mL, 0.96 mol) was heated at 100° C. for 16 hours. The mixture was then concentrated to yield crude the product which was further purified by washing with Et$_2$O to yield Compound 5 (3.8 g) as a white solid. LC-MS: 354 [M+H].

To a solution of Compound 5 (3.8 g, 10 mmol) in EtOH (5 mL) was added 4M HCl in EtOH (100 mL, 0.4 mol) at room temperature. The mixture was heated at 50° C. for 16 hours. After concentration, the crude product which was further purified by washing with Et$_2$O to yield the title compound (3.3 g) as a white solid. LC-MS: 382 [M+H].

Preparation 8: (R)-4-Amino-5-biphenyl-4-yl-2-hydroxy-2-methyl-pentanoic Acid Ethyl Ester

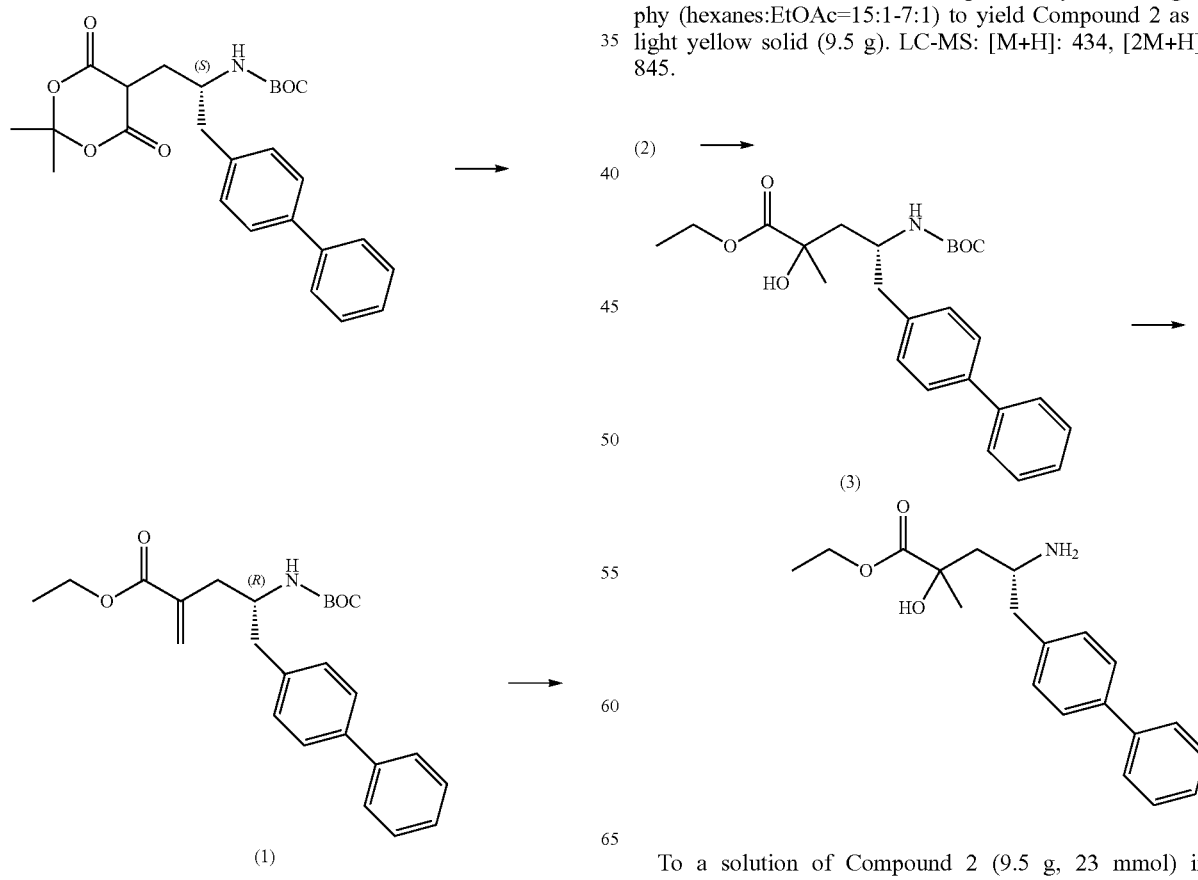

To a solution of [(S)-1-biphenyl-4-ylmethyl-2-(2,2-dimethyl-4,6-dioxo-[1,3]dioxan-5-yl)-ethyl]-carbamic acid t-butyl ester (46 g, 0.1 mol) in t-butyl alcohol (100 mL) was added dimethylmethyleneimmonium iodide (46.3 g, 0.3 mol) at room temperature under nitrogen. The mixture was heated to 65° C. and stirred at this temperature for 16 hours. After filtration, the filtrate was concentrated to yield the crude product which was further purified by chromatography (hexanes:EtOAc=20:1~10:1) to yield Compound 1 as a light yellow solid) (18 g). LC-MS: [M+Na]: 460, [2M+Na]: 897.

To a solution of Compound 1 (18 g, 44 mmol) in acetone (430 mL) and water (22 mL) was added Sudan Red as indicator. Ozone atmosphere was introduced into the mixture at 0° C. until the red color of Sudan Red disappeared. Dimethyl sulfide (45 mL) was added and the mixture was stirred at room temperature overnight. The mixture was then concentrated and the residue was purified by chromatography (hexanes:EtOAc=15:1-7:1) to yield Compound 2 as a light yellow solid (9.5 g). LC-MS: [M+H]: 434, [2M+H]: 845.

To a solution of Compound 2 (9.5 g, 23 mmol) in anhydrous THF (120 mL) was added a solution of methyl-magnesium bromide in THF (9.2 mL, 28 mmol) at −70° C. under nitrogen. The mixture was stirred at −60° C. for 3 hours and the reaction was then quenched with saturated aqueous NH$_4$Cl (50 mL). The organic layer was separated and dried over MgSO$_4$. The mixture was then concentrated and the residue was purified by chromatography (hexanes: EtOAc=10:1~5:1) to yield Compound 3 as an oil (7.9 g). LC-MS: [M+H]: 450, [2M+H]: 877.

To a solution of Compound 3 (7.9 g, 18.4 mmol) in anhydrous DCM (300 mL) was pumped HCl atmosphere at 0° C. for 6 hours. The mixture was then concentrated and the residue was washed with anhydrous Et$_2$O to yield the title compound as a white solid HCl salt (5.8 g). LC-MS: [M+H]: 364, [2M+H]: 727. $^1$H NMR (300 MHz, DMSO): δ8.00-7.97 (d, 4H), 7.67-7.62 (m, 6H), 7.47-7.28 (m, 8H), 6.32 (s, 1H), 6.09 (s, 1H), 4.13-4.06 (m, 2H), 3.95-3.78 (m, 2H), 3.60 (s, 1H), 3.22-3.08 (m, 3H), 2.95-2.65 (m, 2H), 1.99-1.79 (m, 4H), 1.30-0.87 (m, 9H).

Preparation 9: (3R,5R)-5-Amino-6-(4-bromo-2-chlorophenyl)-2-ethoxyhex-1-en-3-ol

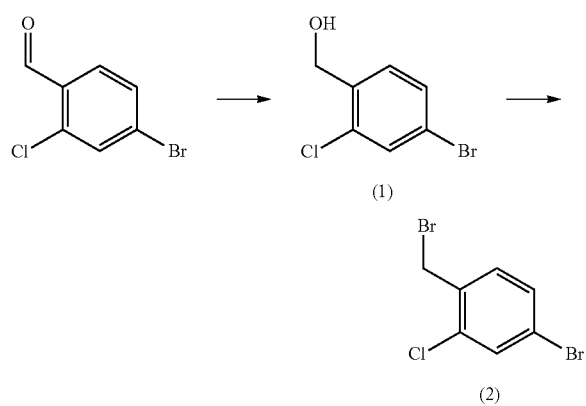

To a suspension of 4-bromo-2-chlorobenzaldehyde (50 g, 22.8 mmol) in MeOH (500 mL) was added NaBH$_4$ (17.3 g, 45.6 mmol) in portions at 0° C. The mixture was stirred for 30 minutes and then aqueous NH$_4$Cl was added to quench the reaction. The mixture was concentrated in vacuo. The residue was extracted with EtOAc (200 mL×2) and the combined organic layers were dried over anhydrous Na$_2$SO$_4$, and concentrated under vacuum to yield Compound 1 (48 g) as a white solid.

To a solution of Compound 1 (46.8 g, 21.1 mmol) in dry DCM (500 mL) was added phosphorous tribromide (68.6 g, 25.3 mmol) dropwise at 0° C. under nitrogen. The mixture was stirred for 2 hours and then washed with saturated aqueous NaHCO$_3$ (200 mL×2) and saturated aqueous NaCl (200 mL), dried over anhydrous Na$_2$SO$_4$, concentrated under vacuum to yield Compound 2 (36 g) as a colorless oil.

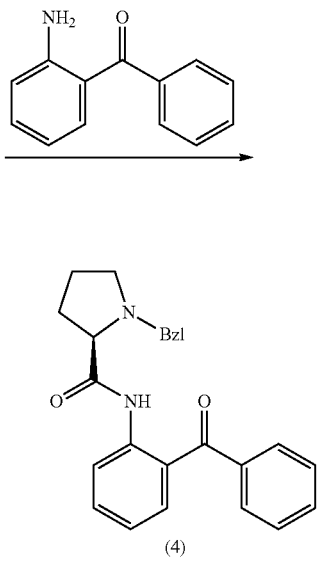

To a stirred solution of (R)-pyrrolidine-2-carboxylic acid (57.7 g, 0.5 mol) and KOH (84 g, 1.5 mol) in isopropyl alcohol (330 mL) was added benzyl chloride (70 mL, 0.6 mol) dropwise at 0° C. over 3 hours. The mixture was then stirred overnight at the same temperature. The resulting mixture was neutralized with concentrate HCl to pH=6, followed by the addition of chloroform (200 mL). The mixture was stirred for 30 minutes, then filtered and the precipitate was washed with chloroform (100 mL×3). The combined chloroform solutions were dried over anhydrous Na$_2$SO$_4$, and concentrated under vacuum to yield Compound 3 (52 g) as a white solid. LC-MS: 206 [M+H]$^+$.

To a solution of Compound 3 (10 g, 48.8 mmol) in dry DCM (50 mL) was added SO$_2$Cl$_2$ (7.3 g, 61 mmol) at −20° C. under nitrogen. The mixture was stirred at −20° C. for 3 hours followed by the addition of a solution of (2-aminophenyl)(phenyl)methanone (6 g, 30.5 mmol) in dry DCM (25 mL) and the mixture was stirred overnight at room temperature. A solution of Na$_2$CO$_3$ (10.3 g) in water (40 mL) was added at 0° C. The organic layer was separated and the aqueous layer was extracted with DCM (50 mL×3). The combined organic layers were dried over anhydrous Na$_2$SO$_4$ and concentrated under vacuum. The residue was washed with MTBE (50 mL×2) to yield Compound 4 (8.5 g) as a yellow solid. LC-MS: 385 [M+H]$^+$.

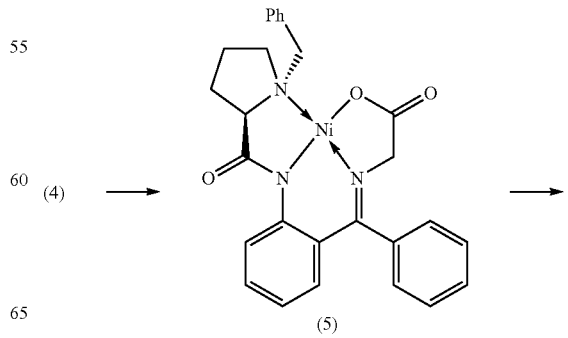

-continued

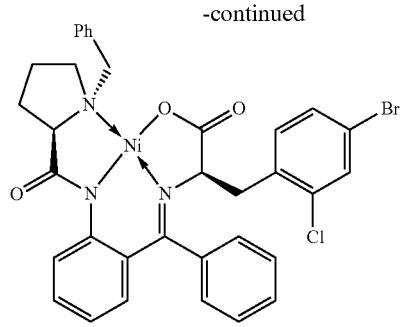

(6)

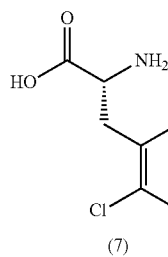

(7)

(7) →

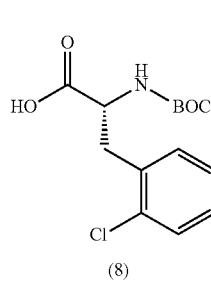

(8)

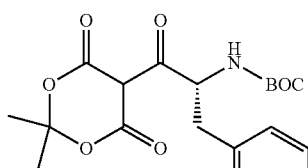

(9)

To a solution of Compound 4 (29.4 g, 76.5 mmol), glycine (28.7 g, 382.4 mmol) and Ni(NO$_3$)$_2$-6H$_2$O (44.5 g, 152.9 mmol) in MeOH (280 mL) was added a solution of KOH (30 g, 535.3 mmol) in MeOH (100 mL) at 45° C. under nitrogen. The mixture was stirred at 60° C. for an hour. The resulting solution was neutralized with AcOH (31 mL) and poured into ice water (380 mL). The resulting solid was filtered and dissolved in DCM (450 mL), which was washed with saturated aqueous NaCl (150 mL), dried over anhydrous Na$_2$SO$_4$ and concentrated. The residue was washed with EtOAc (50 mL×2) to yield compound 5 (38 g) as a red solid. LC-MS: 498 [M+H]$^+$.

Compound 5 (14.3 g, 28.7 mmol) and NaOH (3.4 g, 81.6 mmol) were added to a flask which was purged with nitrogen twice. Anhydrous DMF (100 mL) was added and the mixture was stirred for 5 minutes at 0° C. before a solution of Compound 2 (8.6 g, 30.1 mmol) in DMF (20 mL) was added. The reaction mixture was stirred at room temperature for 30 minutes until complete consumption of Compound 4 (checked by TLC). The resulting mixture was poured into a 5% AcOH aqueous solution (120 mL) which was then extracted with DCM (150 mL×3) and the combined organic layers were washed with saturated aqueous NaCl (150 mL), dried over anhydrous Na$_2$SO$_4$ and concentrated under vacuum. The residue was recrystallized with DCM/Et$_2$O (1:1) to yield Compound 6 (15.5 g) as a red solid. LC-MS: 702 [M+H]$^+$.

To a solution of Compound 6 (46 g, 65.6 mmol) in MeOH (300 mL) was added 3N HCl (200 mL). The mixture was refluxed until the red color turned green. The resulting solution was concentrated under vacuum and concentrated NH$_3$.H$_2$O (100 mL) was added, and followed by the extraction with DCM (200 mL×2). The aqueous phase was concentrated under vacuum and subjected to the cation exchange resin (eluted with NH$_3$.H$_2$O/EtOH, 1:1) to yield Compound 7 (15 g) as a white solid. LC-MS: 280 [M+H]$^+$.

To a suspension of Compound 7 (15 g, 53.9 mmol) in MeCN (150 mL) was added a solution of NaOH (4.3 g, 107.7 mmol) in water (150 mL) at 0° C., and followed by the addition of (BOC)$_2$O (17.6 g, 80.8 mmol). The mixture was stirred overnight at room temperature. The resulting solution was concentrated under vacuum, followed by the extraction with DCM (150 mL×2). The aqueous phase was acidified with 1N HCl to pH=3 and extracted with EtOAc (150 mL×3). The combined organic layers were washed with saturated aqueous NaCl (150 mL), dried over anhydrous Na$_2$SO$_4$ and concentrated under vacuum to yield Compound 8 (12.3 g, 60%) as a white solid. LC-MS: 402 [M+Na]$^+$.

To a suspension of Compound 8 (18.4 g, 48.5 mmol) and Meldrum's acid (8.4 g, 58.2 mmol) in DCM (400 mL) was added DMAP (9.5 g, 77.6 mmol) at −5° C. After stirring for 10 minutes, a solution of DCC (12 g, 58.2 mmol) in DCM (100 mL) was added dropwise at −5° C. The mixture was stirred overnight at room temperature. The resulting solution was cooled to 0° C. and filtered. The filtrate was washed with aqueous citric acid (200 mL×3) and saturated aqueous NaCl (200 mL), dried over anhydrous Na$_2$SO$_4$, and concentrated under vacuum. The residue was washed with Et$_2$O (50 mL×2) to yield Compound 9 (22 g) as a light yellow solid.

(9) →

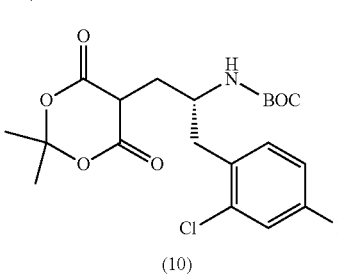

(10)

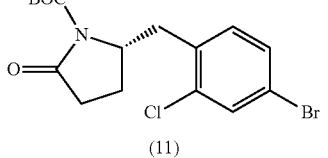

(11)

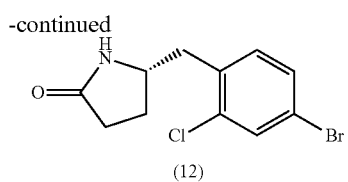

(12)

To a solution of Compound 9 (22 g, 43.6 mmol) in DCM (400 mL) was added AcOH (28.8 g, 479.4 mmol) at 0° C. After stirring for 10 minutes, NaBH$_4$ (4.1 g, 109 mmol) was added in portions. The mixture was stirred for an hour at 0° C. The resulting solution was washed with saturated aqueous NaHCO$_3$ (200 mL×2) and saturated aqueous NaCl (200 mL), dried over anhydrous Na$_2$SO$_4$ and concentrated under vacuum. The residue was washed with ether (100 mL×2) to yield Compound 10 (18.6 g) as an off-white solid. LC-MS: 514 [M+Na]$^+$.

A solution of Compound 10 (18.6 g, 37.9 mmol) in toluene (350 mL) was heated under reflux for 2 hours. Upon cooling, the mixture was evaporated to dryness to yield Compound 11 (14 g) as a yellow syrup. LC-MS: 334 [M-tBu+H]$^+$.

To a solution of Compound 11 (14 g, 36.0 mmol) in DCM (250 mL) was added TFA (20 mL). The mixture was stirred for 4 hours at 0° C. The resulting solution was concentrated under vacuum to remove TFA. The residue was dissolved in DCM (400 mL) and washed with saturated aqueous NaHCO$_3$ (200 mL×2), dried over anhydrous Na$_2$SO$_4$ and concentrated to yield Compound 12 (10 g) as a yellow solid. LC-MS: 290 [M+H]$^+$.

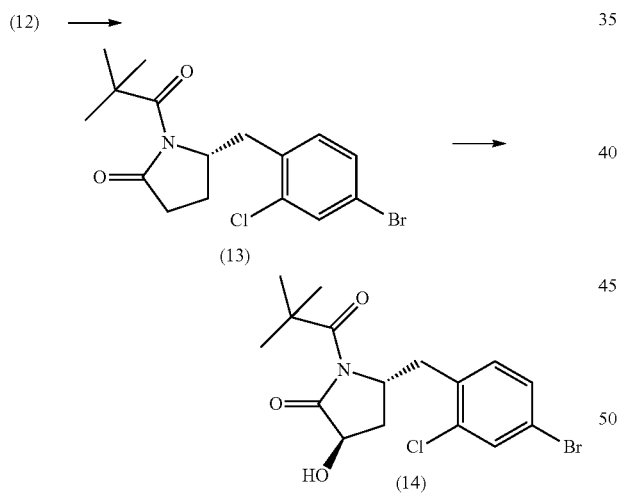

To a solution of Compound 12 (10 g, 34.7 mmol) in dry THF (250 mL) was added NaH (2.4 g, 69.3 mmol, 70%) at 0° C. The mixture was stirred for one hour at 0° C. under nitrogen. Then pivaloyl chloride (5 g, 41.6 mmol) was added. After stirring for another 2 hours, saturated aqueous NaHCO$_3$ (100 mL) was added to quench the reaction. The resulting mixture was concentrated and extracted with EtOAc (100 mL×3) and the combined organic layers were washed with saturated aqueous NaCl (100 mL), dried over anhydrous Na$_2$SO$_4$ and concentrated under vacuum. The residue was purified by silica gel chromatography (hexanes/EtOAc, 5:1) to yield Compound 13 (11.8 g) as a white solid. LC-MS: 374[M+H]$^+$.

To a solution of Compound 13 (11.8 g, 31.8 mmol) in dry THF (70 mL) was added NaHMDS (24 mL, 47.7 mmol, 2.0 M in THF) dropwise at −78° C. under nitrogen. After stirring for 30 minutes, a solution of (+)-(8,8-dichlorocamphoryl-sulfonyl)oxaziridine (15.2 g, 50.8 mmol) in THF (70 mL) was added dropwise at −78° C. The mixture was stirred for another hour at the same temperature before aqueous NH$_4$Cl (70 mL) was added to quench the reaction. The resulting mixture was extracted with EtOAc (150 mL×3) and the combined organic layers were washed with saturated aqueous NaCl (150 mL), dried over anhydrous Na$_2$SO$_4$, concentrated under vacuum and purified by silica gel chromatography (hexanes/EtOAc, 20:1~5:1) to yield the crude product (5 g), which was further purified by preparative HPLC to yield Compound 14 (4 g) as a yellow solid. LC-MS: 390 [M+H]$^+$.

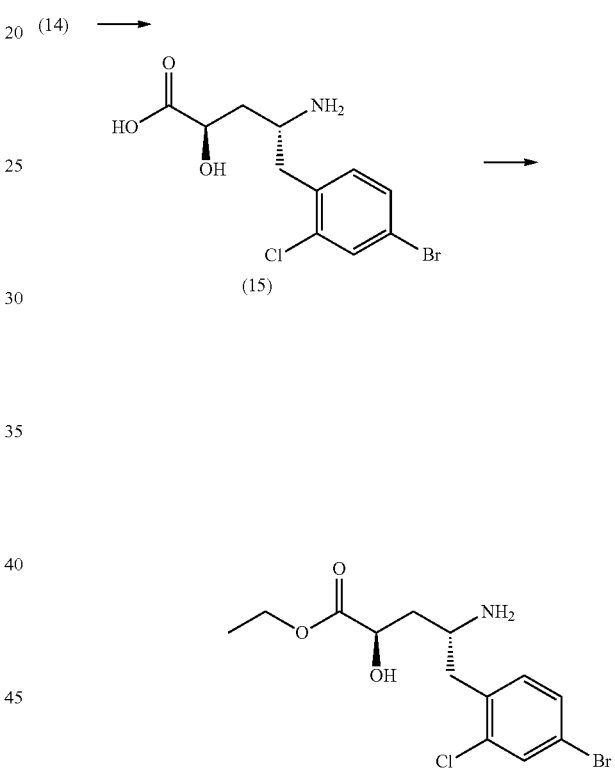

A solution of Compound 14 (4 g, 10.3 mmol) in concentrated HCl (50 mL) was heated under reflux overnight. The mixture was concentrated under vacuum and the resulting solid was washed with Et$_2$O (50 mL×2) to yield Compound 15 (3.1 g) as a white solid HCl salt. LC-MS: 324 [M+H]$^+$.

A solution of Compound 15 (3.1 g, 8.6 mmol) in HCl/EtOH (6.7M, 40 mL) was stirred overnight at 50° C. The resulting mixture was concentrated under vacuum and the residue was washed with ether (50 mL×2) to yield the title compound (2.9 g) as an off-white solid HCl salt. LC-MS: 352 [M+H]$^+$. $^1$H NMR: (CD$_3$OD) 1.268 (t, J=6.9 Hz, 3H), 1.862-1.946 (m, 1H), 2.068-2.143 (m, 1H), 3.104-3.199 (m, 2H), 3.769-3.809 (m, 1H), 4.162-4.209 (m, 2H), 4.274-4.881 (m, 1H), 7.325 (dd, J=8.1, 2.1 Hz, 1H), 7.522 (dd, J=8.3, 3.0 Hz, 1H), 7.696 (d, J=1.8 Hz, 1H).

Preparation 10: (2R,4S)-5-Biphenyl-4-yl-4-t-butoxycarbonylamino-2-hydroxymethylpentanoic Acid Ethyl Ester (compound 7) and (2S,4S)-5-Biphenyl-4-yl-4-t-butoxycarbonylamino-2-hydroxymethylpentanoic Acid Ethyl Ester (compound 8)

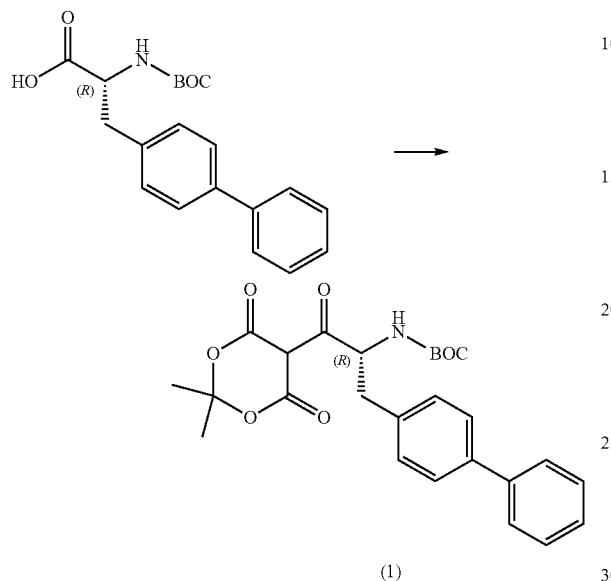

(1)

To a solution of (R)-3-biphenyl-4-yl-2-t-butoxycarbonylamino-propionic acid (50 g, 146 mmol), Meldrum's acid (23.3 g, 161 mmol) and DMAP (27.8 g, 227 mmol) in anhydrous DCM (500 mL) was added a solution of DCC (33.3 g, 161 mmol) in anhydrous DCM (200 mL) over 1 hour at −5° C. under nitrogen. The mixture was stirred at −5° C. for 8 hours, then refrigerated overnight, during which tiny crystals of dicyclohexylurea precipitated. After filtration, the mixture was washed with 5% KHSO$_4$ (4×200 mL) and saturated aqueous NaCl (1×200 mL), then dried under refrigeration with MgSO$_4$ overnight. The solution was evaporated to yield the title compound (68 g, light yellow solid), which was used without further purification. LC-MS: 490 [M+Na], 957 [2M+Na].

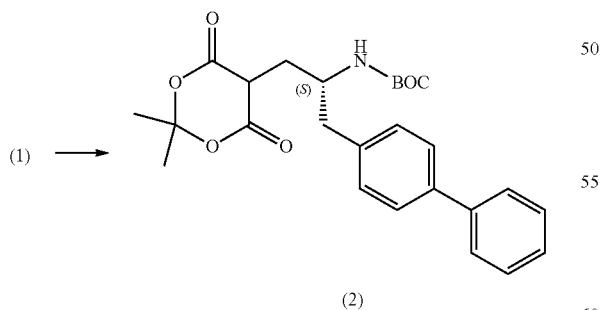

(1) →

(2)

To a solution of crude Compound 1 (68 g, 147 mmol) in anhydrous DCM (1 L) was added AcOH (96.7 g, 1.6 mol) at −5° C. under nitrogen. The mixture was stirred at −5° C. for 0.5 hour, then NaBH$_4$ (13.9 g, 366 mmol) was added in small portions over 1 hour. After stirring for another 1 hour at −5° C., saturated aqueous NaCl (300 mL) was added. The organic layer was washed with saturated aqueous NaCl (2×300 mL) and water (2×300 mL), dried over MgSO$_4$, filtered, and evaporated to yield the crude product, which was further purified by chromatography (hexanes:EtOAc=5:1) to yield Compound 2 (46 g, light yellow solid). LC-MS: 476 [M+Na], 929 [2M+Na].

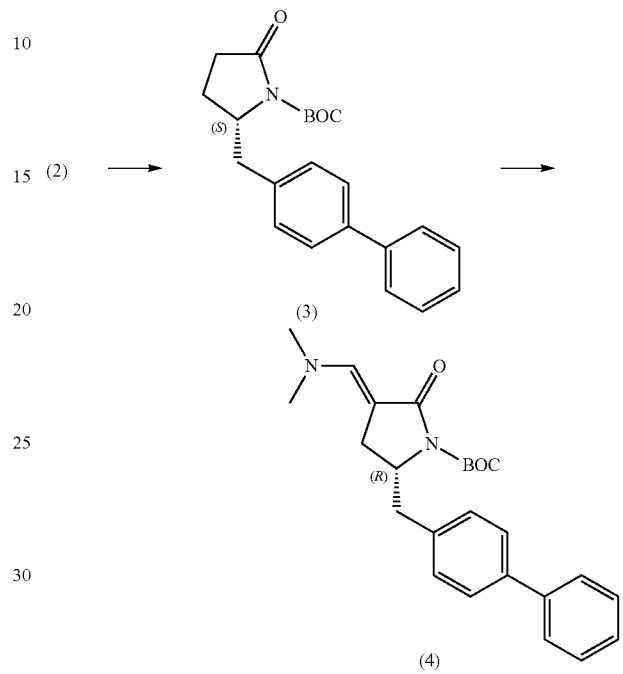

A solution of Compound 2 (46 g, 101 mmol) in anhydrous toluene (300 mL) was refluxed under nitrogen for 3 hours. After evaporation of the solvent, the residue was purified by chromatography (hexanes:EtOAc=10:1) to yield Compound 3 (27 g, light yellow solid). LC-MS: 374 [M+Na], 725 [2M+Na]. $^1$H NMR (300 MHz, CDCl3): δ7.64-7.62 (m, 4H), 7.51-7.46 (m, 2H), 7.42-7.39 (m, 1H), 7.39-7.30 (m, 2H), 4.50-4.43 (m, 1H), 3.27-3.89 (m, 1H), 2.88-2.80 (m, 1H), 2.48-2.42 (m, 2H), 2.09-1.88 (m, 2H), 1.66 (s, 9H).

A mixture of Compound 3 (27 g, 77 mmol) and t-butoxy-N,N,N',N'-tetramethylmethanediamine (40.3 g, 231 mmol) was heated to 80° C. under nitrogen. After stirring for 3 hours at 80° C., the mixture was diluted with EtOAc (300 mL), washed with water (2×150 mL) and saturated aqueous NaCl (2×150 mL), dried over MgSO$_4$, filtered, and evaporated to yield crude Compound 4 (29.7 g, light yellow oil). LC-MS: 425 [M+H], 835 [2M+H].

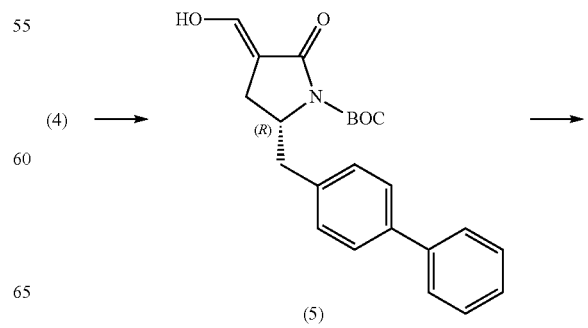

(4) →

(5)

-continued

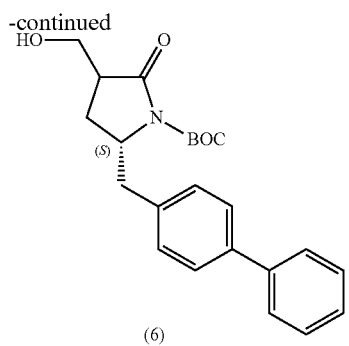

(6)

To a solution of crude Compound 4 (29.7 g, 73 mmol) in THF (200 mL) was added 1 M HCl (81 mL) at 0° C. under nitrogen. After stirring for 1 hour at room temperature, the mixture was diluted with EtOAc (100 mL) and adjusted with saturated aqueous NaHCO$_3$ to pH 7. The aqueous layer was extracted with EtOAc (2×150 mL) and the combined organic layers were washed with water (2×150 mL) and saturated aqueous NaCl (1×150 mL), dried over MgSO$_4$, filtered, and evaporated to yield crude Compound 5 (29.4 g, yellow oil). LC-MS: 402 [M+Na], 781 [2M+Na].

To a solution of Compound 5 (29.4 g, 77 mmol) in anhydrous THF (300 mL) was added anhydrous EtOH (30 mL) and AcOH (92.5 g, 1.5 mol) at −5° C. under nitrogen. The mixture was stirred at −5° C. for 0.5 hour, then NaBH$_3$CN (19.4 g, 308 mmol) was added in small portions over 1 hour. After stirring for one additional hour at −5° C., the mixture was adjusted with saturated aqueous NaHCO$_3$ to pH 7. The aqueous layers were extracted with EtOAc (2×200 mL) and the combined organic layers were washed with water (2×150 mL) and saturated aqueous NaCl (1×150 mL), dried over MgSO$_4$, filtered, and concentrated to yield the crude product, which was further purified by chromatography (hexanes:EtOAc=5:1) to yield Compound 6 (11.2 g, light yellow solid). LC-MS: 404 [M+Na], 785 [2M+Na].

To a solution of Compound 6 (11.2 g, 29 mmol) in anhydrous EtOH (500 mL) was added anhydrous K$_2$CO$_3$ (8.0 g, 58 mmol) at 0° C. under nitrogen. After stirring for 1 hour at 0° C., the mixture was warmed to room temperature and stirred for 16 hours. After filtration, the filtrate was concentrated and the residual was diluted with water (150 mL), DCM (200 mL) and saturated aqueous NaCl (50 mL). After separation, the aqueous layer was extracted with DCM (2×150 mL). The combined organic layers were washed with saturated aqueous NaCl (2×200 mL), dried over MgSO$_4$, and concentrated to yield the crude product which was further purified by column chromatography (hexanes:EtOAc=5:1) to yield Compounds 7 and 8 (8.3 g, light yellow solid).

Compound 7: LC-MS: 450 [M+Na], 877 [2M+Na]. $^1$H NMR (300 MHz, CDCl3): δ7.58-7.23 (m, 9H), 4.46-4.43 (d, 1H), 4.20-4.13 (m, 2H), 3.94 (s, 1H), 3.82-3.70 (m, 2H), 2.85-2.70 (m, 3H), 2.25-2.22 (d, 1H), 2.01-1.92 (m, 1H), 1.47 (s, 9H), 1.26-1.24 (m, 3H).

Compound 8: LC-MS: 450 [M+Na], 877 [2M+Na]. $^1$H NMR (300 MHz, CDCl3): δ7.58-7.55 (m, 4H), 7.50-7.43 (m, 2H), 7.40-7.30 (m, 1H), 7.26-7.23 (m, 1H), 4.46 (m, 1H), 4.21-4.13 (m, 2H), 3.94 (m, 1H), 3.82-3.77 (m, 2H), 2.83-2.81 (d, 2H), 2.66-2.63 (m, 1H), 2.24 (m, 1H), 1.83-1.81 (m, 2H), 1.38 (s, 9H), 1.30-1.25 (m, 3H).

Preparation 11: (2S,4S)-4-Amino-5-(2'-fluorobiphenyl-4-yl)-2-hydroxymethylpentanoic Acid Ethyl Ester

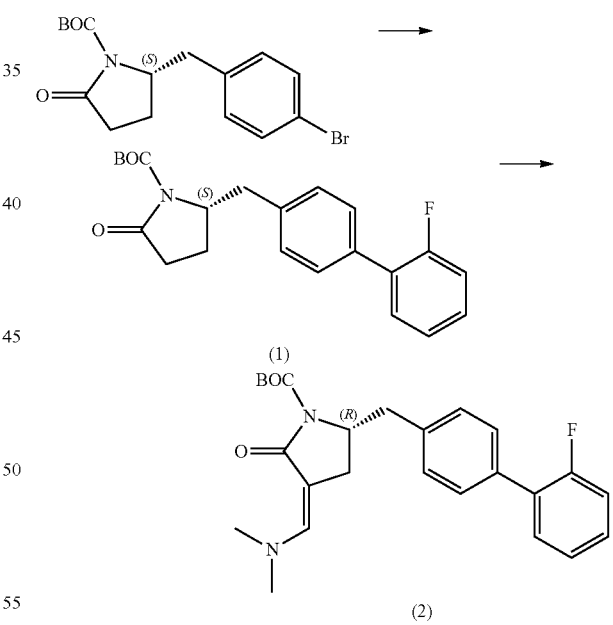

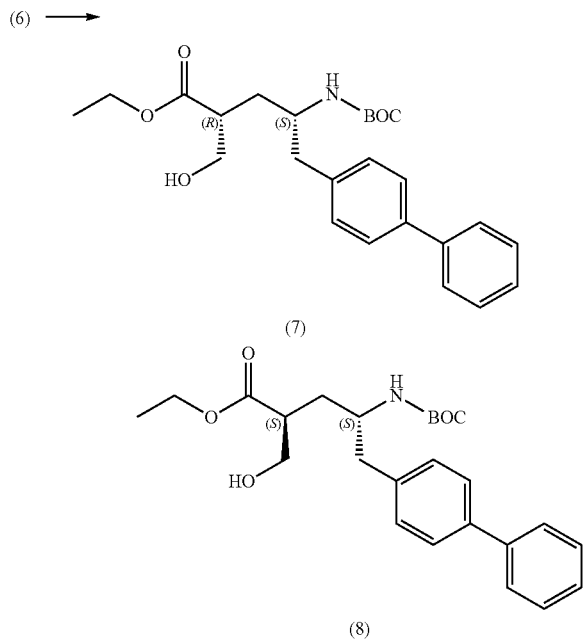

To a solution of (S)-2-(4-bromobenzyl)-5-oxopyrrolidine-1-carboxylic acid t-butyl ester (18.4 g, 52 mmol) in 1,4-dioxane (500 mL) was added 2-fluorophenylboronic acid (8.7 g, 63 mmol) and Pd(dppf)$_2$Cl$_2$ (3.8 g, 5.2 mmol) at room temperature under nitrogen. After stirring for 10 minutes, a solution of K$_2$CO$_3$ (14.4 g, 104 mmol) in water (50 mL) was added. The mixture was heated to 80° C. and stirred at this temperature for 5 hours. After evaporation of the solvent, water (300 mL) was added and the mixture was extracted with EtOAc (3×200 mL). The combined organic layers were washed with saturated aqueous NaCl (400 mL), dried over Na$_2$SO$_4$ and concentrated to give the crude product which was further purified by column chromatography (hexanes:EtOAc=8:1) to yield Compound 1 (17.3 g) as a red oil. LC-MS: 392 [M+Na].

A mixture of Compound 1 (17.3 g, 46.7 m mol) and t-butoxy-N,N,N',N'-tetramethylmethanediamine (24.4 g, 140 mmol) was heated to 80° C. under nitrogen. After stirring for 3 hours at 80° C., the mixture was diluted with EtOAc (300 mL) and washed with water (2×150 mL), saturated aqueous NaCl (150 mL), dried over MgSO$_4$, filtered, and evaporated to yield crude Compound 2 (20.6 g) as a red oil. LC-MS: 425 [M+H], 849 (2M+H).

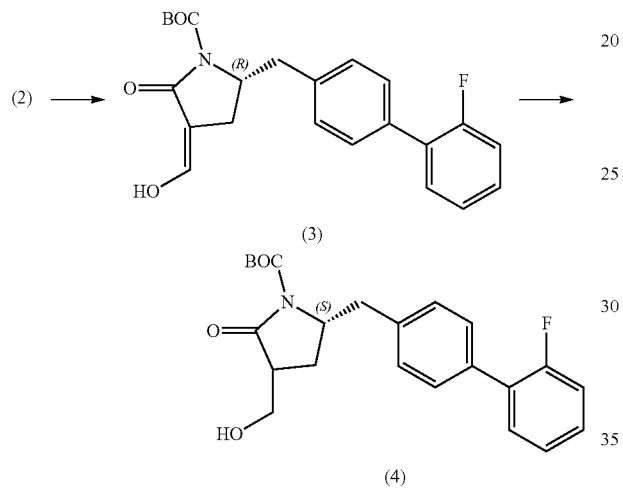

To a solution of crude Compound 2 (20.6 g, 48.6 mmol) in THF (300 mL), was added 1 M HCl (58 mL, 58 mmol) at 0° C. under nitrogen. After stirring for 1 hour at room temperature, the mixture was diluted with EtOAc (100 mL) and adjusted with saturated aqueous NaHCO$_3$ to a pH of 7. The aqueous layer was extracted with EtOAc (2×150 mL) and the combined organic layers were washed with water (2×150 mL) and saturated aqueous NaCl (150 mL), dried over MgSO$_4$, filtered, and evaporated to yield the crude Compound 3 (18.9 g) as a red oil. LC-MS: 420 (M+Na), 817 (2M+Na).

To a solution of crude Compound 3 (18.9 g, 47.6 mmol) in anhydrous THF (400 mL) was added anhydrous EtOH (50 mL) and AcOH (57.2 g, 952 mmol) at −5° C. under nitrogen. The mixture was stirred at −5° C. for 30 minutes, then NaBH$_3$CN (15 g, 238 mmol) was added in small portions over 1 hour. After stirring for an additional 1 hour at −5° C., the mixture was adjusted with saturated aqueous NaHCO$_3$ to a pH of 7. The aqueous layer was extracted with EtOAc (3×200 mL) and the combined organic layers were washed with water (2×150 mL) and saturated aqueous NaCl (150 mL), dried over MgSO$_4$, filtered, and concentrated to yield the crude product which was further purified by chromatography (hexanes:EtOAc=6:1) to yield Compound 4 (7.1 g) as a light yellow solid. LC-MS: 422 (M+Na), 821 (2M+Na).

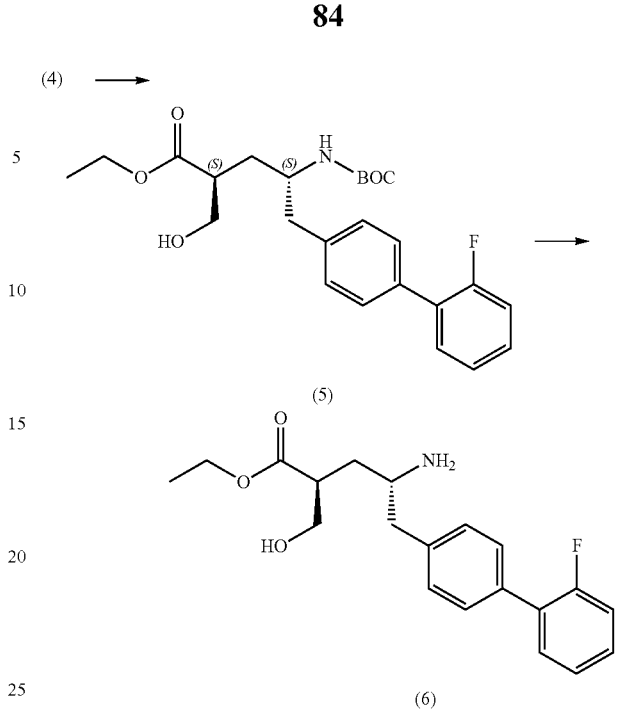

To a solution of Compound 4 (7.1 g, 17.7 mmol) in anhydrous EtOH (500 mL) was added anhydrous K$_2$CO$_3$ (9.8 g, 70.8 mmol) at 0° C. under nitrogen. After stirring for 1 hour at 0° C., the mixture was warmed to room temperature and stirred for 16 hours. After filtration, the filtrate was concentrated and the residual was diluted with water (150 mL), DCM (200 mL) and saturated aqueous NaCl (50 mL). After separation, the aqueous layer was extracted with DCM (2×150 mL). The combined organic layers were washed with saturated aqueous NaCl (2×200 mL), dried over MgSO$_4$, and concentrated to yield the crude product which was further purified by column chromatography (hexanes:EtOAc=5:1) to yield Compound 5 (2 g) as a light yellow solid. 2.1 g of the (R,S) isomer was also obtained as a light yellow solid.

Compound 5 (400 mg, 0.9 mmol) was dissolved in MeCN (3 mL) and 4 M HCl in dioxane (0.5 mL). The mixture was stirred at room temperature for 1 hour then concentrated to yield the title compound as an HCl salt (340 mg), which was formed as an oil and solidified overnight.

Preparation 12: (2S,4R)-4-Amino-5-biphenyl-4-yl-2-hydroxymethyl-2-methylpentanoic Acid Ethyl Ester

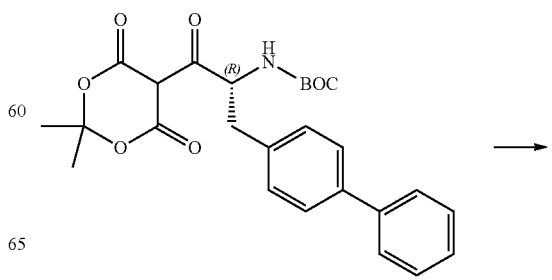

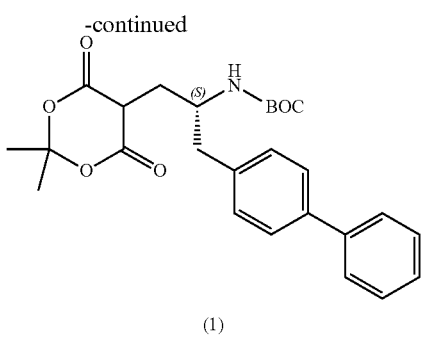

(1)

AcOH (8.6 mL) was added to a solution of crude [(R)-1-biphenyl-4-ylmethyl-2-(2,2-dimethyl-4,6-dioxo-[1,3]dioxan-5-yl)-2-oxo-ethyl]-carbamic acid t-butyl ester (6.4 g, 14 mmol) in anhydrous MeCN (90 mL) was added AcOH (8.6 mL) at −5° C. under nitrogen. The mixture was stirred at −5° C. for 30 minutes, then sodium borohydride (1.3 g, 34.5 mmol) was added in small portions over 2 hours. After stirring for another 1 hour at −5° C., saturated aqueous NaCl and 1.7 M of NaCl in water (30 mL) was added. The layers were separated and the organic layer was washed with saturated aqueous NaCl (2×30 mL) and water (2×30 mL), dried under MgSO₄, filtered and evaporated, The resulting crude product was further purified by chromatography (5:1 heptane:EtOAc) to yield Compound 1 (1.1 g, purity 98.4%) as a light yellow solid.

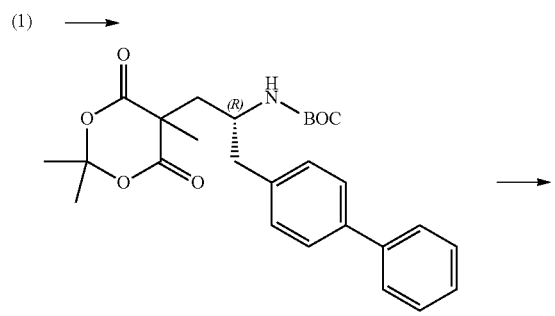

Compound 1 (5.0 g, 11 mmol) and K₂CO₃ (1.8 g, 13.2 mmol) were stirred in DMF (33.9 mL) at 0° C. under nitrogen. Methyl iodide (892 µL) was added and the resulting mixture was stirred at 0° C. for 1 hour. The mixture was allowed to warm to room temperature. Saturated aqueous NaCl (35 mL) and EtOAc (35 mL) were added, and the resulting mixture was stirred for 2 minutes. The organic layer was separated, dried (Na₂SO₄) and the solvent evaporated. The residue was triturated with EtOAc (20 mL). The solid was filtered off and dried under vacuum. The filtrate was concentrated and triturated again with EtOAc to yield Compound 2 (3.9 g).

Distilled water (140 mL) was purged 30 minutes under nitrogen, then cannulated into a vessel containing 0.1 M of samarium diiodide in THF (800 mL), exercising caution to not allow air into the reaction. While maintaining an atmosphere of nitrogen, a degassed solution of Compound 2 (3.7 g, 8.0 mmol) in THF (100 mL) was added via cannula. The resulting mixture was stirred for 15 minutes, then exposed to air. The solution turned white. Saturated aqueous NaCl (12 mL), 10% citric acid (6 mL), and EtOAc (30 mL) were added. The mixture was stirred for 5 minutes, then the organic layer was separated, dried over Na₂SO₄ and concentrated in vacuo. The crude material was purified by normal phase chromatography (330 g gold column, 50% EtOAc with 0.5% AcOH/ether gradient). The desired diastereomer fractions were combined and the solvent was concentrated in vacuo. The BOC intermediate was stirred in MeCN (10 mL) and 4N HCl in dioxane (10 mL) for 30 min. The solvent was evaporated and the product was azeotroped with toluene (2×) to yield Compound 3 (1.0 g) as an HCl salt.

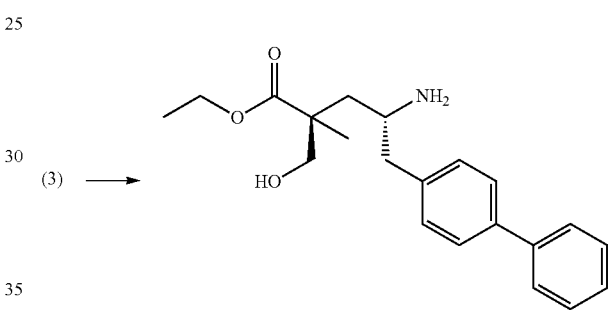

Compound 3 (0.3 g, 957 µmol) was combined with EtOH (6 mL) and 4 M of HCl in 1,4-dioxane (718 µL), and stirred overnight. The solvents were evaporated and the product was azeotroped with toluene (2×) to yield the title compound (295 mg) as an HCl salt, which was used without further purification.

Preparation 13: (2S,4R)-4-Amino-5-(3'-fluorobiphenyl-4-yl)-2-hydroxymethyl-2-methylpentanoic Acid

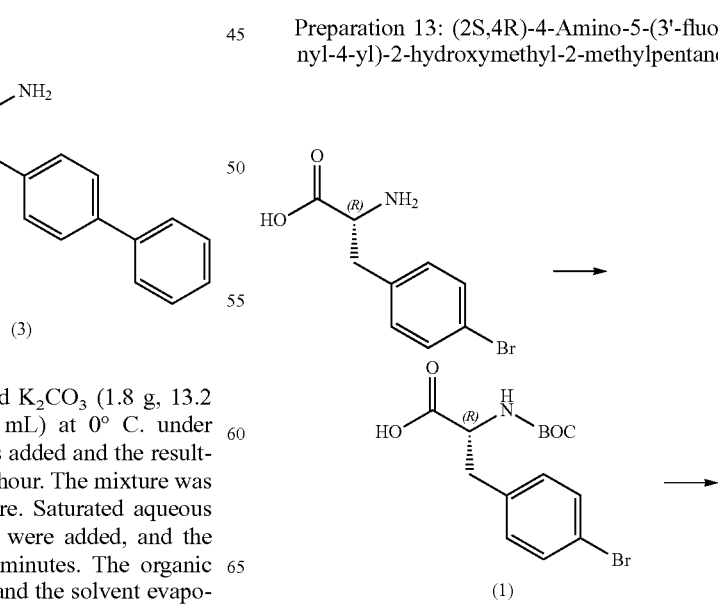

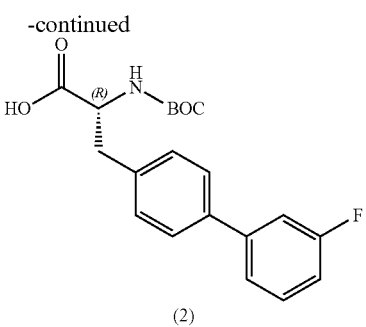

(2)

The solution was evaporated to yield the crude Compound 3 (57.7 g, light yellow oil). LC-MS: 508 [M+Na], 993 [2M+Na].

(3) →

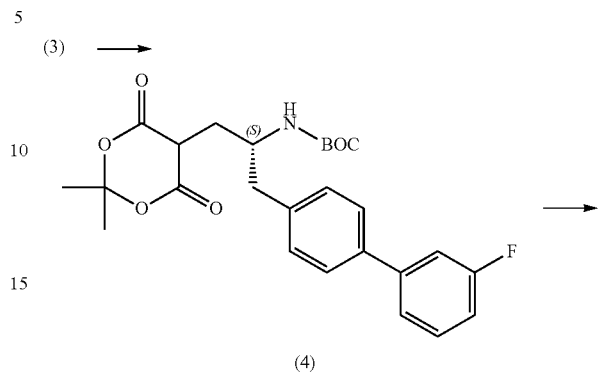

(4)

To a solution of (R)-2-amino-3-(4-bromophenyl)propionic acid (50 g, 0.2 mol) in MeCN (700 mL) was added a solution of NaOH (16.4 g, 0.4 mol) in water (700 mL) at −5° C. After stirring for 10 minutes, a solution of (BOC)$_2$O (44.7 g, 0.2 mol) in MeCN (100 mL) was added. The mixture was warmed to room temperature and stirred overnight. After evaporation of the MeCN, the residue was diluted with DCM (800 mL) and acidified with 1 M HCl to pH 2 at −5° C. The aqueous layer was extracted with DCM (3×200 mL). The combined organic layers were washed with saturated aqueous NaCl (500 mL), dried over anhydrous Na$_2$SO$_4$ and concentrated to yield Compound 1 (64.2 g, white solid). LC-MS: 366 [M+Na], 709 [2M+Na].

To a solution of Compound 1 (64.2 g, 187 mmol) in 1,4-dioxane (500 mL) was added 3-fluorophenylboronic acid (31.3 g, 224 mmol) and Pd(dppf)$_2$Cl$_2$ (13.7 g, 19 mmol) at room temperature under nitrogen. After stirring for 10 min, a solution of K$_2$CO$_3$ (51.7 g, 374 mmol) in water (250 mL) was added. The mixture was heated to 100° C. and stirred overnight. After evaporation of the solvent, water (200 mL) was added. The aqueous layer was acidified with 1 M HCl to pH 2 and extracted with EtOAc (3×200 mL). The combined organic layers were washed with saturated aqueous NaCl (400 mL), dried over anhydrous Na$_2$SO$_4$, and concentrated to yield the crude product which was further purified by column chromatography (hexanes:EtOAc=4:1) to yield Compound 2 (45 g, light yellow oil). LC-MS: 382 [M+Na], 741 [2M+Na].

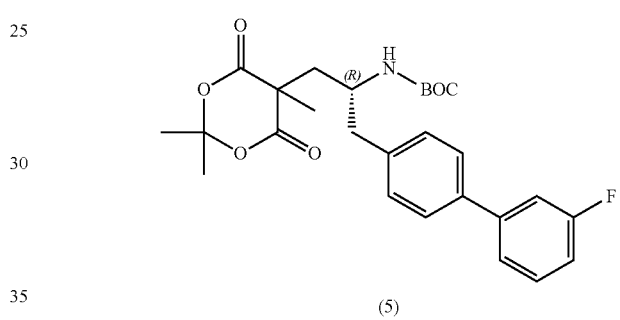

(5)

To a solution of the crude Compound 3 (57.7 g, 119 mmol) in anhydrous DCM (1 L) was added AcOH (78.4 g, 1.3 mol) at −5° C. under nitrogen. The mixture was stirred at −5° C. for 0.5 hour, then NaBH$_4$ (11.3 g, 0.3 mol) was added in small portions over 1 hour. After stirring for another 1 hour at −5° C., saturated aqueous NaCl (300 mL) was added. The organic layer was washed with saturated aqueous NaCl (2×300 mL) and water (2×300 mL), dried over anhydrous MgSO$_4$, filtered and concentrated to yield the crude product, which was further purified by chromatography (hexanes:EtOAc=6:1) to yield Compound 4 (28 g, light yellow oil). LC-MS: 494 [M+Na], 965 [2M+Na].

To a solution of Compound 4 (28 g, 60 mmol) in anhydrous DMF (250 mL) was added K$_2$CO$_3$ (9.9 g, 72 mmol) and CH$_3$I (25.6 g, 180 mmol) at 0° C. under nitrogen. After stirring for 1 hour at 0° C., the mixture was warmed to room temperature and stirred overnight. The mixture was diluted with water (3 L) and extracted with EtOAc (3×300 mL). The combined organic layers were washed with saturated aqueous NaCl (500 mL), dried over anhydrous Na$_2$SO$_4$, and concentrated to give the crude product which was further purified by chromatography (hexanes:EtOAc=5:1) to yield Compound 5 (11.7 g, light yellow solid). LC-MS: 508 [M+Na], 993 [2M+Na]. $^1$H NMR (300 MHz, CD$_3$OD): δ7.52-7.49 (m, 2H), 7.41-7.39 (m, 2H), 7.32-7.27 (m, 3H), 7.07-7.01 (m, 1H), 6.21-6.18 (d, 1H), 3.79 (m, 1H), 2.78-2.61 (m, 2H), 2.35-2.20 (m, 2H), 1.76 (s, 6H), 1.59 (s, 3H), 2.21 (s, 1H), 1.28 (s, 9H).

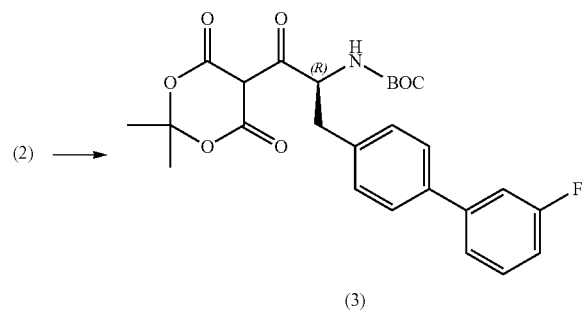

(2) →

(3)

To a solution of Compound 2 (45 g, 125 mmol), Meldrum's acid (23.5 g, 163 mmol), and DMAP (26.0 g, 213 mmol) in anhydrous DCM (500 mL) was added a solution of DCC (33.3 g, 163 mmol) in anhydrous DCM (200 mL) over 1 hour at −5° C. under nitrogen. The mixture was stirred at −5° C. for 8 hours, then refrigerated overnight, during which tiny crystals of dicyclohexylurea precipitated. After filtration, the mixture was washed with 5% KHSO$_4$ (4×200 mL) and saturated aqueous NaCl (1×200 mL), then dried under refrigeration with anhydrous MgSO$_4$ overnight.

89

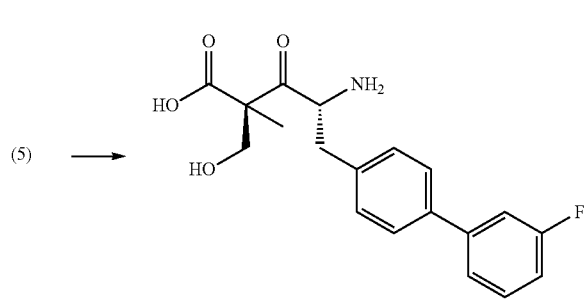 [SMILES: C[C@](CO)(C(=O)O)C(=O)[C@H](N)Cc1ccc(-c2cccc(F)c2)cc1]

(5) →

Distilled Water (181 mL) was purged 1 hour under nitrogen, then cannulated into a vessel containing 0.1 M of samarium diiodide in THF (800 mL). While maintaining an atmosphere of nitrogen, a similarly degassed solution of Compound 5 (4.9 g, 10.0 mmol) and THF (20 mL) was added via cannula. The resulting mixture was stirred for 15 minutes, then exposed to air. A white solid formed. The THF was evaporated, and EtOAc (200 mL) was added followed by saturated aqueous NaCl (50 mL) and 10% citric acid (20 mL). The mixture was stirred for 5 minutes, then the organic layer was separated, dried over $Na_2SO_4$ and concentrated in vacuo. The crude product was purified by normal phase chromatography (330 g gold column, 1:1 ether:EtOAc with 0.5% AcOH). The fraction containing the desired diastereomers were combined. The solvent was evaporated in vacuo to yield the BOC-protected acid (1.5 g). The BOC was cleaved by stirring the intermediate in 4M HCl in dioxane (6 mL) and MeCN (10 mL) for 30 minutes. The solvent was then evaporated in vacuo to yield the title compound as an HCl salt.

Preparation 14: [(R)-1-(4-Bromobenzyl)-2-(2,2,5-trimethyl-4,6-dioxo-[1,3]dioxan-5-yl)ethyl]carbamic Acid t-Butyl Ester

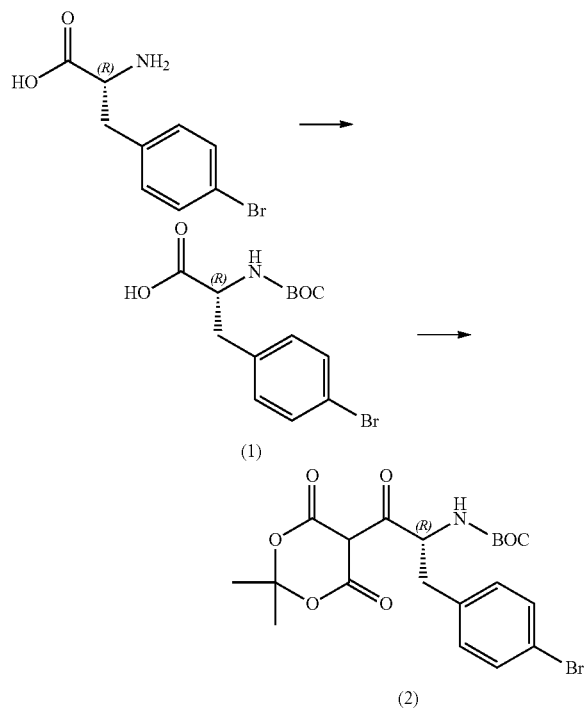

To a mixture of (R)-2-amino-3-(4-bromophenyl)propionic acid (100 g, 410 μmol) in MeCN (600 mL) was added dropwise a solution of NaOH (32.8 g, 820 μmol) in water (800 mL) at 0° C. The resulting solution was stirred for 30 minutes. A solution of $(BOC)_2O$ (93.8 g, 430 μmol) in MeCN (200 mL) was added, and the resulting mixture was warmed to room temperature and stirred overnight. The MeCN was evaporated and the residue was diluted with DCM (1 L) and acidified with 2 M HCl to pH=2 at −5° C. The aqueous layer was extracted with DCM and the combined organic layers were washed with saturated aqueous NaCl (500 mL), dried over anhydrous $Na_2SO_4$ and concentrated to yield crude Compound 1 (141 g, 100%) as a yellow solid. LC-MS: 366[M+Na].

Compound 1 (20 g, 58.1 mmol) was combined with 2,2-dimethyl-1,3-dioxane-4,6-dione (9.2 g, 63.9 mmol), DMAP (10.7 g, 87.2 mmol), and anhydrous DCM (400 mL), and cooled to 0° C. After stirring for 30 minutes, a solution of DCC (13.2 g, 63.9 mmol) in DCM (50 mL) was added dropwise at 0° C. under nitrogen. After the addition, the ice bath was removed and the mixture was stirred at room temperature overnight. The solution was cooled at −20° C. for 1 hour and then the solids were filtered off. The filtrate was washed with a 5% $KHSO_4$ solution (4×100 mL) and saturated aqueous NaCl (200 mL). The organic layer was dried over anhydrous $Na_2SO_4$ and evaporated to yield crude Compound 2 (27.5 g) as a gray solid. LC-MS: 492 [M+Na]$^+$.

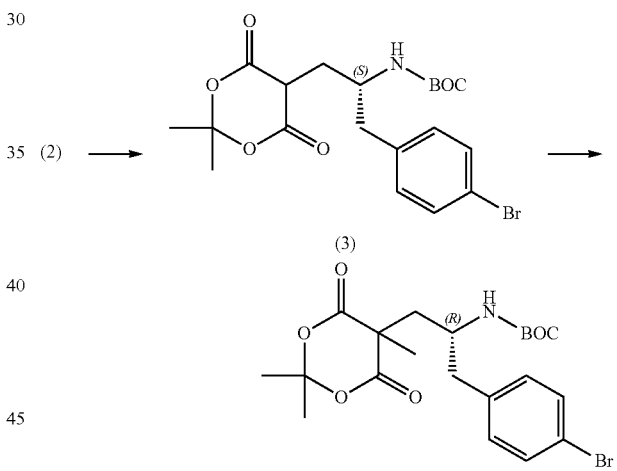

To a solution of Compound 2 (27.5 g, 58.1 mmol) in anhydrous DCM (400 mL) was added AcOH (38.4 g, 639.1 mmol) at −5° C. under nitrogen. The mixture was stirred at −5° C. for 30 minutes. $NaBH_4$ (5.5, 145.2 mmol) was added in portions over 30 minutes, and the resulting solution was stirred at room temperature for 3 hours. Saturated aqueous NaCl (300 mL) was added to quench the reaction. The organic layer was washed with saturated aqueous NaCl (2×200 mL), dried over anhydrous $Na_2SO_4$ and concentrated to yield crude Compound 3 (22.6 g). LC-MS: 478 [M+Na]$^+$.

To a solution of Compound 3 (22.6 g, 49.6 mmol) and $K_2CO_3$ (8.3 g, 59.5 mmol) in anhydrous DMF (160 mL) was added methyl iodide (14 g, 99.2 mmol) dropwise at 0° C. After the addition, the solution was stirred at room temperature overnight. The mixture was evaporated and the residue was dissolved in EtOAc (500 mL) and washed with saturated aqueous NaCl (2×200 mL). The organic solution was dried over anhydrous $Na_2SO_4$ and concentrated to yield the crude product which was triturated with ethyl ether (100 mL), then filtered to yield the title compound (14.5 g) as a white solid. LC-MS: 492 [M+Na]+.

Preparation 15: (2S,4R)-4-t-Butoxycarbonylamino-5-(3'-chlorobiphenyl-4-yl)-2-hydroxymethyl-2-methylpentanoic Acid

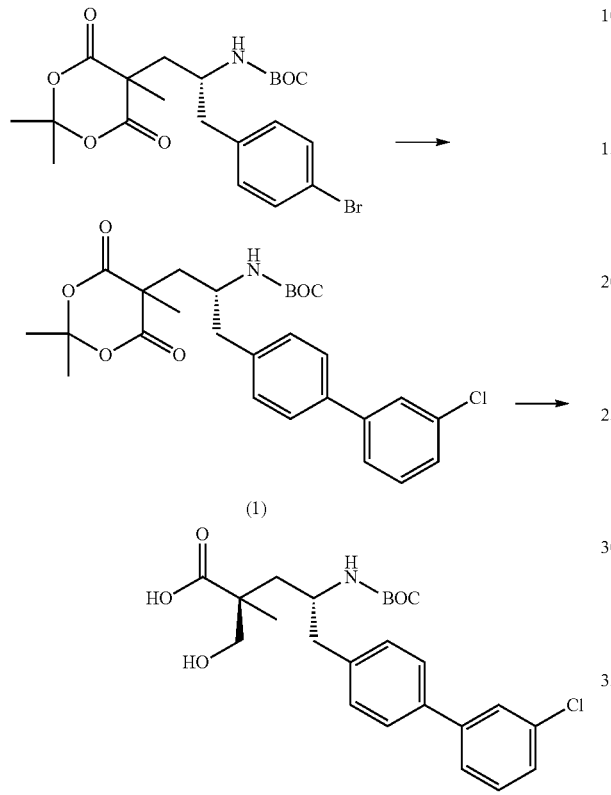

A mixture of [(R)-1-(4-bromobenzyl)-2-(2,2,5-trimethyl-4,6-dioxo-[1,3]dioxan-5-yl)ethyl]carbamic acid t-butyl ester (8 g, 17 mmol), 3-chlorophenylboronic acid (3 g, 18.7 mmol), Pd(dppf)₂Cl₂ (400 mg, 550 μmol) and potassium fluoride (2 g, 34 mmol) in water (80 mL) and dioxane (80 mL) was stirred at 60° C. under argon for 3 hours. The mixture was concentrated, dispersed in water (150 mL), extracted with EtOAc (2×100 mL), dried over anhydrous Na₂SO₄ and evaporated to yield the crude product, which was purified by column chromatography (PE:EtOAc=10:1) to yield Compound 1 (7 g) as a white solid. LC-MS: 524 [M+Na]+

Samarium powder (50 g, 330 μmol) was flushed with argon (20 minutes). Anhydrous THF (1.5 L) was added and the resulting suspension was bubbled with argon (15 minutes). Iodine (70 g, 270 mmol) was added and the mixture was flushed again with argon (10 minutes). The mixture was covered with aluminum foil and heated at 65° C. overnight then allowed to cool to room temperature. A solution of Compound 1 (7 g, 13.9 mmol) in THF (200 mL) and water (100 mL) was sealed and flushed with argon (10 minutes), cooled to −70° C., flushed with argon (10 minutes), cooled to −70° C., and flushed with argon (30 minutes). The samarium powder solution (1.5 L) was then added to the cooled solution via cannula, and stirred at room temperature for 2 hours. The solution was evaporated, and the residue was dissolved in EtOAc (200 mL), washed with tartaric acid solution (10%, 150 mL), dried over anhydrous Na₂SO₄, concentrated and purified by column chromatography (PE: EtOAc=0 to 30%, added with 0.05% AcOH) to yield the title compound (3 g) as a white solid. LC-MS: 470 [M+Na]+. ¹H NMR (300 MHz, CD3OD): δ 7.28-7.56 (m, 8H), 3.94 (s, 1H), 3.56~3.66 (m, 2H), 2.69~2.82 (m, 2H), 1.70~1.90 (m, 2H), 1.17~1.31 (m, 12H).

Preparation 16: (2S,4R)-4-Amino-5-(3'-chlorobiphenyl-4-yl)-2-hydroxymethyl-2-methylpentanoic Acid

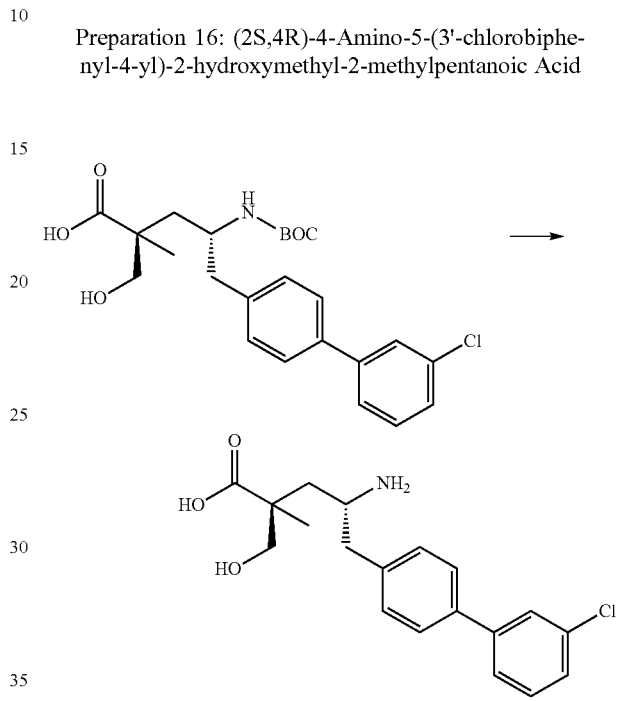

(2S,4R)-4-t-Butoxycarbonylamino-5-(3'-chlorobiphenyl-4-yl)-2-hydroxymethyl-2-methylpentanoic acid (773 mg, 1.8 mmol) was combined with MeCN (4 mL) and 4N HCl in dioxane (1 mL) and stirred for 20 minutes. The reaction mixture was concentrated under reduced pressure then purified (Interchim reverse-phase) to yield the title compound as a TFA salt.

Example 1: (2R,4R)-5-(3'-Chlorobiphenyl-4-yl)-2-hydroxy-4-(2-oxobutyrylamino)pentanoic Acid

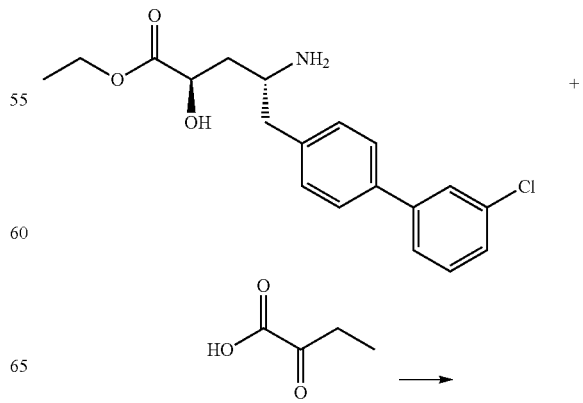

93
-continued

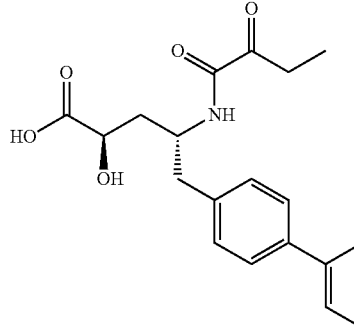

(2R,4R)-4-Amino-5-(3'-chlorobiphenyl-4-yl)-2-hydroxy-pentanoic acid ethyl ester (50 mg, 144 μmol) was added to a solution of 2-oxo-butyric acid (1.2 eq., 165 μmol) and HATU (71.1 mg, 187 μmol) in DMF (250 μL), followed by the addition of DIPEA (75 μL, 431 μmol). The resulting mixture was stirred at room temperature for 1 hour. 10 M aqueous LiOH (115 μL, 1.2 mmol) was added and the mixture was stirred for an additional 1 hour. The mixture was washed with DCM (1 mL) and the aqueous layer was acidified with concentrated HCl (250 μL) and extracted with DCM (2×1 mL). The DCM extracts were combined and concentrated in vacuo, and the resulting crude liquid was purified by reverse phase preparative HPLC to yield the title compound (2.9 mg). MS m/z [M+H]$^+$ calc'd for $C_{21}H_{22}ClNO_5$, 404.12; found 404.2.

Example 2

Following the procedures described in the examples herein, and substituting the appropriate starting materials and reagents, the following compounds were prepared as the parent compound. These compounds, where X is —C(O)—R$^6$, are depicted by formula IIa:

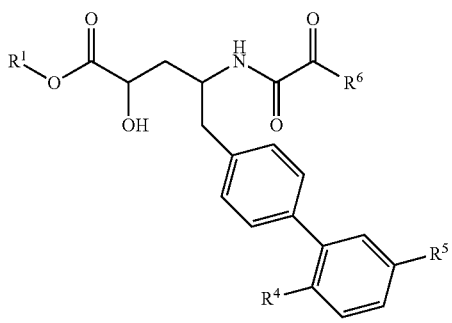

(IIa)

R$^1$ and R$^4$ = H; R$^5$ = Cl

| Ex. | R$^6$ | Formula | MS m/z: [M + H]$^+$ calcd | found |
|---|---|---|---|---|
| 1 | —CH$_2$CH—(CH3)2 | C$_{23}$H$_{26}$ClNO$_5$ | 432.15 | 432.2 |
| 2 | benzyl | C$_{26}$H$_{24}$ClNO$_5$ | 466.13 | 466.2 |

1. (2R,4R)-5-(3'-Chloro-biphenyl-4-yl)-2-hydroxy-4-(4-methyl-2-oxo-pentanoylamino)-pentanoic acid 2. (2R,4R)-5-(3'-Chloro-biphenyl-4-yl)-2-hydroxy-4-(2-oxo-3-phenyl-propionylamino)-pentanoic acid Example 3: (2R,4R)-5-(3'-Chlorobiphenyl-4-yl)-2-hydroxy-4-[2-((S)-2-hydroxymethylpyrrolidin-1-yl)-2-oxo-acetylamino]pentanoic Acid

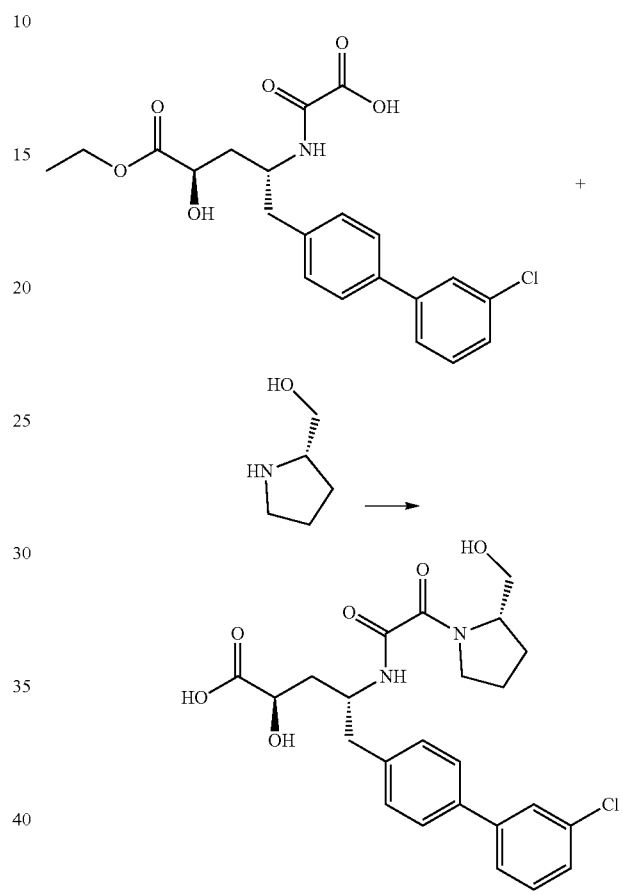

DIPEA (62 μl, 357 μmol) was added to a solution of (S)-1-pyrrolidin-2-yl-methanol (L-prolinol; 18 μL, 179 μmol), (2R,4R)-5-(3'-chlorobiphenyl-4-yl)-2-hydroxy-4-(oxalylamino)pentanoic acid ethyl ester (50 mg, 119 μmol) and HATU (58.9 mg, 155 μmol) in DMF (0.5 mL), and the resulting mixture was stirred at room temperature for 10 minutes. 5 M aqueous LiOH (191 μL, 953 μmol) was added and the mixture was stirred at room temperature for 10 minutes. AcOH (2 mL) was added and the mixture was purified (Interchim reverse-phase 30 g column using H$_2$O/MeCN 30-95%) to yield the title compound as a white solid (29.5 mg). MS m/z [M+H]$^+$ calc'd for $C_{24}H_{27}ClN_2O_6$, 475.16; found 475.2.

Example 4

Following the procedures described in the examples herein, and substituting the appropriate starting materials and reagents, the following compounds were prepared as the parent compound or as a TFA salt. These compounds, where X is —C(O)—NR$^7$R$^8$, are depicted by formula IIb:

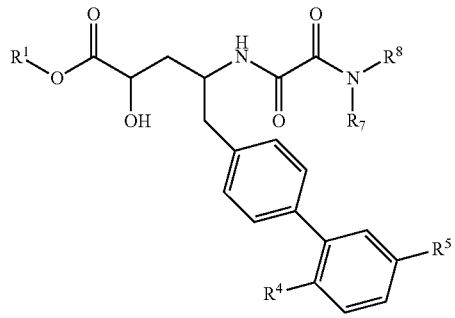

(IIb)

R¹ and R⁴ = H; R⁵ = Cl

| Ex. | R⁷ | R⁸ | Formula | MS m/z: [M + H]⁺ calcd | found |
|---|---|---|---|---|---|
| 1 | H | cyclopentyl | $C_{24}H_{27}ClN_2O_5$ | 459.16 | 459.2 |
| 2 | H | 5-(2-bromopyridyl) | $C_{24}H_{21}BrClN_3O_5$ | 546.04 | 546.2 |
| 3 | H | 4-pyridyl | $C_{24}H_{22}ClN_3O_5$ | 468.12 | 468.2 |
| 4 | H | 4-methyl-3-pyridyl | $C_{25}H_{24}ClN_3O_5$ | 482.14 | 482.2 |
| 5 | H | —O-benzyl | $C_{26}H_{25}ClN_2O_6$ | 497.14 | 497.2 |
| 6 | H | —O—CH₃ | $C_{20}H_{21}ClN_2O_6$ | 421.11 | 421.2 |
| 7 | H | 3-oxo-isoxazolidin-4-yl | $C_{22}H_{22}ClN_3O_7$ | 476.11 | 476.2 |
| 8 | H | morpholin-4-yl | $C_{23}H_{26}ClN_3O_6$ | 476.15 | 476.2 |
| 9 | OH | phenyl | $C_{25}H_{23}ClN_2O_6$ | 483.12 | 483.2 |
| 10 | OH | —CH₃ | $C_{20}H_{21}ClN_2O_6$ | 421.11 | 421.2 |
| 11 | —CH₃ | —CH₃ | $C_{21}H_{23}ClN_2O_5$ | 419.13 | 419.2 |
| 12 | —CH₃ | —O—CH₃ | $C_{21}H_{23}ClN_2O_6$ | 435.12 | 435.1 |

1. (2R,4R)-5-(3'-Chlorobiphenyl-4-yl)-4-(cyclopentylaminooxalylamino)-2-hydroxypentanoic acid
2. (2R,4R)-4-[(6-Bromopyridin-3-ylaminooxalyl)amino]-5-(3'-chlorobiphenyl-4-yl)-2-hydroxypentanoic acid
3. (2R,4R)-5-(3'-Chlorobiphenyl-4-yl)-2-hydroxy-4-[(pyridin-4-ylaminooxalyl)-amino]-pentanoic acid
4. (2R,4R)-5-(3'-Chlorobiphenyl-4-yl)-2-hydroxy-4-[(4-methylpyridin-3-ylaminooxalyl)amino]pentanoic acid
5. (2R,4R)-4-(Benzyloxyaminooxalylamino)-5-(3'-chlorobiphenyl-4-yl)-2-hydroxy-pentanoic acid
6. (2R,4R)-5-(3'-Chlorobiphenyl-4-yl)-2-hydroxy-4-(methoxyaminooxalylamino)-pentanoic acid
7. (2R,4R)-5-(3'-Chlorobiphenyl-4-yl)-2-hydroxy-4-[(3-oxo-isoxazolidin-4-ylaminooxalyl)-amino]pentanoic acid
8. (2R,4R)-5-(3'-Chlorobiphenyl-4-yl)-2-hydroxy-4-[(morpholin-4-ylaminooxalyl)-amino]pentanoic acid
9. (2R,4R)-5-(3'-Chlorobiphenyl-4-yl)-2-hydroxy-4-[(hydroxyphenylaminooxalyl)-amino]pentanoic acid
10. (2R,4R)-5-(3'-Chlorobiphenyl-4-yl)-2-hydroxy-4-[(hydroxymethylaminooxalyl)-amino]pentanoic acid
11. (2R,4R)-5-(3'-Chlorobiphenyl-4-yl)-4-(dimethylaminooxalylamino)-2-hydroxy-pentanoic acid
12. (2R,4R)-5-(3'-Chlorobiphenyl-4-yl)-2-hydroxy-4-[(methoxymethylaminooxalyl)-amino]pentanoic acid

| Ex. | R⁷ and R⁸ taken together to form a ring | Formula | MS m/z: [M + H]⁺ calcd | found |
|---|---|---|---|---|
| 13 | 3-hydroxyazetidin-1-yl | $C_{22}H_{23}ClN_2O_6$ | 447.12 | 447.2 |
| 14 | 3,3-difluoroazetidin-1-yl | $C_{22}H_{21}ClF_2N_2O_5$ | 467.11 | 467.2 |
| 15 | 3-(methylsulfonyl)pyrrolidin-1-yl | $C_{24}H_{27}ClN_2O_7S$ | 523.12 | 523.2 |

-continued

| Ex. | R⁷ and R⁸ taken together to form a ring | Formula | MS m/z: [M + H]⁺ calcd | found |
|---|---|---|---|---|
| 16 | (pyrrolidine with CH₂OH) | $C_{24}H_{27}ClN_2O_6$ | 475.16 | 475.2 |
| 17 | (pyrrolidine with C(O)NH₂) | $C_{24}H_{26}ClN_3O_6$ | 488.15 | 488.2 |
| 18 | (4-hydroxypiperidine) | $C_{24}H_{27}ClN_2O_6$ | 475.16 | 475.2 |
| 19 | (4-methoxymethylpiperidine) | $C_{26}H_{31}ClN_2O_6$ | 503.19 | 503.2 |
| 20 | (4-hydroxymethylpiperidine) | $C_{25}H_{29}ClN_2O_6$ | 489.17 | 489.2 |
| 21 | (3-hydroxypiperidine) | $C_{24}H_{27}ClN_2O_6$ | 475.16 | 475.2 |
| 22 | (4-hydroxy-4-methylpiperidine) | $C_{25}H_{29}ClN_2O_6$ | 489.17 | 489.2 |
| 23 | (4-(pyridin-4-yl)piperidine) | $C_{29}H_{30}ClN_3O_5$ | 536.19 | 536.2 |
| 24 | (4-(2-hydroxyethyl)piperidine) | $C_{26}H_{31}ClN_2O_6$ | 503.19 | 503.2 |
| 25 | (2-hydroxymethylpiperidine) | $C_{25}H_{29}ClN_2O_6$ | 489.17 | 489.2 |
| 26 | (2-hydroxymethylpiperidine) | $C_{25}H_{29}ClN_2O_6$ | 489.17 | 489.2 |

-continued
| Ex. | R⁷ and R⁸ taken together to form a ring | Formula | MS m/z: [M + H]⁺ calcd | found |
|---|---|---|---|---|
| 27 | 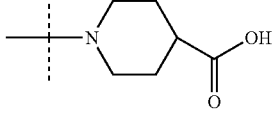 | $C_{25}H_{27}ClN_2O_7$ | 503.15 | 503.2 |
| 28 | 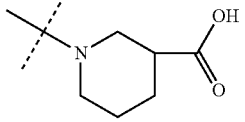 | $C_{25}H_{27}ClN_2O_7$ | 503.15 | 503.2 |
| 29 | 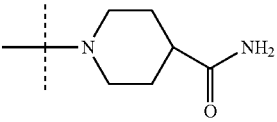 | $C_{25}H_{28}ClN_3O_6$ | 502.17 | 502.2 |
| 30 | 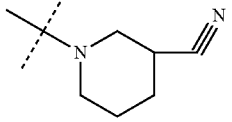 | $C_{25}H_{26}ClN_3O_5$ | 484.16 | 484.2 |
| 31 | 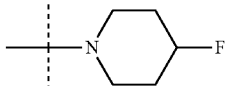 | $C_{24}H_{26}ClFN_2O_5$ | 477.15 | 477.2 |
| 32 | 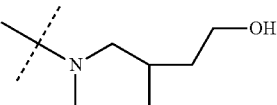 | $C_{26}H_{31}ClN_2O_6$ | 503.19 | 503.2 |
| 33 | 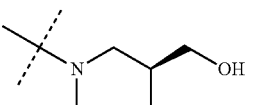 | $C_{25}H_{29}ClN_2O_6$ | 489.17 | 489.2 |
| 34 | 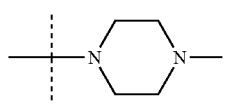 | $C_{24}H_{28}ClN_3O_5$ | 474.17 | 474.2 |
| 35 | 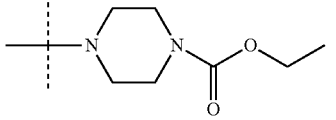 | $C_{26}H_{30}ClN_3O_7$ | 532.18 | 532.2 |
| 36 | 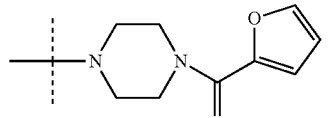 | $C_{28}H_{28}ClN_3O_7$ | 554.16 | 554.4 |
| 37 | 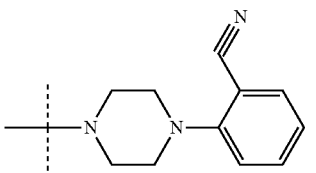 | $C_{30}H_{29}ClN_4O_5$ | 561.18 | 561.2 |

-continued
| Ex. | R⁷ and R⁸ taken together to form a ring | Formula | MS m/z: [M + H]⁺ calcd | found |
|---|---|---|---|---|
| 38 | 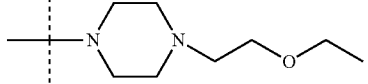 | $C_{27}H_{34}ClN_3O_6$ | 532.21 | 532.2 |
| 39 | 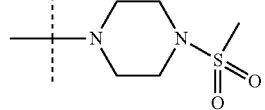 | $C_{24}H_{28}ClN_3O_7S$ | 538.13 | 538.2 |
| 40 | 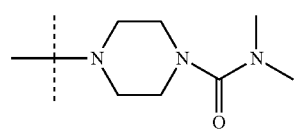 | $C_{26}H_{31}ClN_4O_6$ | 531.19 | 531.2 |
| 41 | 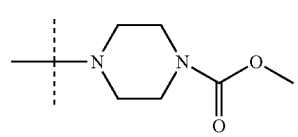 | $C_{25}H_{28}ClN_3O_7$ | 518.16 | 518.2 |
| 42 | 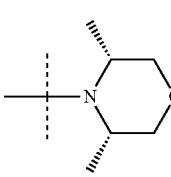 | $C_{25}H_{29}ClN_2O_6$ | 489.17 | 489.2 |
| 43 | 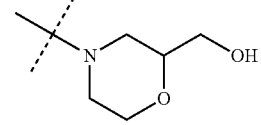 | $C_{24}H_{27}ClN_2O_7$ | 491.15 | 491.2 |
| 44 | 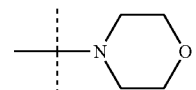 | $C_{23}H_{25}ClN_2O_6$ | 461.14 | 461.2 |
| 45 | 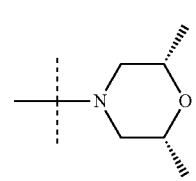 | $C_{25}H_{29}ClN_2O_6$ | 489.17 | 489.2 |
| 46 | 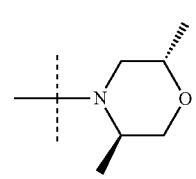 | $C_{25}H_{29}ClN_2O_6$ | 489.17 | 489.2 |
| 47 | 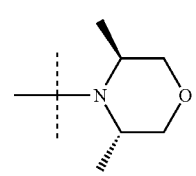 | $C_{25}H_{29}ClN_2O_6$ | 489.17 | 489.2 |

-continued

| Ex. | R⁷ and R⁸ taken together to form a ring | Formula | MS m/z: [M + H]⁺ calcd | found |
|---|---|---|---|---|
| 48 | (isoxazolidine N-gem-dimethyl) | $C_{22}H_{23}ClN_2O_6$ | 447.12 | 447.0 |
| 49 | (4-hydroxyisoxazolidine N-gem-dimethyl) | $C_{22}H_{23}ClN_2O_7$ | 463.12 | 463.0 |
| 50 | (2-oxa-6-azaspiro[3.3]heptane gem-dimethyl) | $C_{24}H_{25}ClN_2O_6$ | 473.14 | 473.2 |

13. (2R,4R)-5-(3'-Chlorobiphenyl-4-yl)-2-hydroxy-4-[2-(3-hydroxyazetidin-1-yl)-2-oxo-acetylamino]pentanoic acid
14. (2R,4R)-5-(3'-Chlorobiphenyl-4-yl)-4-[2-(3,3-difluoroazetidin-1-yl)-2-oxo-acetylamino]-2-hydroxypentanoic acid
15. (2R,4R)-5-(3'-Chlorobiphenyl-4-yl)-2-hydroxy-4-[2-(3-methanesulfonyl-pyrrolidin-1-yl)-2-oxo-acetylamino]pentanoic acid
16. (2R,4R)-5-(3'-Chlorobiphenyl-4-yl)-2-hydroxy-4-[2-((R)-2-hydroxymethyl-pyrrolidin-1-yl)-2-oxo-acetylamino]pentanoic acid
17. (2R,4R)-4-[2-(3-Carbamoylpyrrolidin-1-yl)-2-oxo-acetylamino]-5-(3'-chloro-biphenyl-4-yl)-2-hydroxypentanoic acid
18. (2R,4R)-5-(3'-Chlorobiphenyl-4-yl)-2-hydroxy-4-[2-(4-hydroxy-piperidin-1-yl)-2-oxo-acetylamino]pentanoic acid
19. (2R,4R)-5-(3'-Chlorobiphenyl-4-yl)-2-hydroxy-4-[2-(4-methoxymethyl-piperidin-1-yl)-2-oxo-acetylamino]pentanoic acid
20. (2R,4R)-5-(3'-Chlorobiphenyl-4-yl)-2-hydroxy-4-[2-(4-hydroxymethyl-piperidin-1-yl)-2-oxo-acetylamino]pentanoic acid
21. (2R,4R)-5-(3'-Chlorobiphenyl-4-yl)-2-hydroxy-4-[2-((R)-3-hydroxy-piperidin-1-yl)-2-oxo-acetylamino]pentanoic acid
22. (2R,4R)-5-(3'-Chlorobiphenyl-4-yl)-2-hydroxy-4-[2-(4-hydroxy-4-methyl-piperidin-1-yl)-2-oxo-acetylamino]pentanoic acid
23. (2R,4R)-5-(3'-Chlorobiphenyl-4-yl)-2-hydroxy-4-[2-oxo-2-(3,4,5,6-tetrahydro-2H-[4,4']bipyridinyl-1-yl)-acetylamino]pentanoic acid
24. (2R,4R)-5-(3'-Chlorobiphenyl-4-yl)-2-hydroxy-4-{2-[4-(2-hydroxyethyl)-piperidin-1-yl]-2-oxo-acetylamino}pentanoic acid
25. (2R,4R)-5-(3'-Chlorobiphenyl-4-yl)-2-hydroxy-4-[2-((R)-2-hydroxymethyl-piperidin-1-yl)-2-oxo-acetylamino]pentanoic acid
26. (2R,4R)-5-(3'-Chlorobiphenyl-4-yl)-2-hydroxy-4-[2-((S)-2-hydroxymethyl-piperidin-1-yl)-2-oxo-acetylamino]pentanoic acid
27. 1-[(1R,3R)-3-Carboxy-1-(3'-chlorobiphenyl-4-ylmethyl)-3-hydroxypropyl-aminooxalyl]-piperidine-4-carboxylic acid
28. 1-[(1R,3R)-3-Carboxy-1-(3'-chlorobiphenyl-4-ylmethyl)-3-hydroxypropyl-aminooxalyl]-piperidine-3-carboxylic acid
29. (2R,4R)-4-[2-(4-Carbamoyl-piperidin-1-yl)-2-oxo-acetylamino]-5-(3'-chlorobiphenyl-4-yl)-2-hydroxypentanoic acid
30. (2R,4R)-5-(3'-Chlorobiphenyl-4-yl)-4-[2-(3-cyanopiperidin-1-yl)-2-oxo-acetylamino]-2-hydroxypentanoic acid
31. (2R,4R)-5-(3'-Chlorobiphenyl-4-yl)-4-[2-(4-fluoropiperidin-1-yl)-2-oxo-acetylamino]-2-hydroxypentanoic acid
32. (2R,4R)-5-(3'-Chlorobiphenyl-4-yl)-2-hydroxy-4-{2-[3-(2-hydroxyethyl)-piperidin-1-yl]-2-oxo-acetylamino}pentanoic acid
33. (2R,4R)-5-(3'-Chlorobiphenyl-4-yl)-2-hydroxy-4-[2-((S)-3-hydroxymethyl-piperidin-1-yl)-2-oxo-acetylamino]pentanoic acid
34. (2R,4R)-5-(3'-Chlorobiphenyl-4-yl)-2-hydroxy-4-[2-(4-methyl-piperazin-1-yl)-2-oxo-acetylamino]pentanoic acid
35. 4-[(1R,3R)-3-Carboxy-1-(3'-chlorobiphenyl-4-ylmethyl)-3-hydroxy-propylaminooxalyl]-piperazine-1-carboxylic acid ethyl ester
36. (2R,4R)-5-(3'-Chlorobiphenyl-4-yl)-4-{2-[4-(furan-2-carbonyl)-piperazin-1-yl]-2-oxo-acetylamino}-2-hydroxypentanoic acid
37. (2R,4R)-5-(3'-Chlorobiphenyl-4-yl)-4-{2-[4-(2-cyanophenyl)-piperazin-1-yl]-2-oxo-acetylamino}-2-hydroxypentanoic acid
38. (2R,4R)-5-(3'-Chlorobiphenyl-4-yl)-4-{2-[4-(2-ethoxyethyl)-piperazin-1-yl]-2-oxo-acetylamino}-2-hydroxypentanoic acid
39. (2R,4R)-5-(3'-Chlorobiphenyl-4-yl)-2-hydroxy-4-[2-(4-methanesulfonyl-piperazin-1-yl)-2-oxo-acetylamino]pentanoic acid
40. (2R,4R)-5-(3'-Chlorobiphenyl-4-yl)-4-[2-(4-dimethylcarbamoyl-piperazin-1-yl)-2-oxo-acetylamino]-2-hydroxypentanoic acid
41. 4-[(1R,3R)-3-Carboxy-1-(3'-chlorobiphenyl-4-ylmethyl)-3-hydroxy-propylaminooxalyl]-piperazine-1-carboxylic acid methyl ester
42. (2R,4R)-5-(3'-Chlorobiphenyl-4-yl)-4-[2-((3R,5S)-3,5-dimethylmorpholin-4-yl)-2-oxo-acetylamino]-2-hydroxypentanoic acid 43. (2R,4R)-5-(3'-Chlorobiphenyl-4-yl)-2-hydroxy-4-[2-(2-hydroxymethyl-morpholin-4-yl)-2-oxo-acetylamino]pentanoic acid
44. (2R,4R)-5-(3'-Chlorobiphenyl-4-yl)-2-hydroxy-4-(2-morpholin-4-yl-2-oxo-acetylamino)pentanoic acid
45. (2R,4R)-5-(3'-Chlorobiphenyl-4-yl)-4-[2-((2R,6S)-2,6-dimethylmorpholin-4-yl)-2-oxo-acetylamino]-2-hydroxypentanoic acid
46. (2R,4R)-5-(3'-Chlorobiphenyl-4-yl)-4-[2-((2S,5R)-2,5-dimethylmorpholin-4-yl)-2-oxo-acetylamino]-2-hydroxypentanoic acid
47. (2R,4R)-5-(3'-Chlorobiphenyl-4-yl)-4-[2-((3S,5S)-3,5-dimethylmorpholin-4-yl)-2-oxo-acetylamino]-2-hydroxypentanoic acid
48. (2R,4R)-5-(3'-Chlorobiphenyl-4-yl)-2-hydroxy-4-(2-isoxazolidin-2-yl-2-oxo-acetylamino)pentanoic acid
49. (2R,4R)-5-(3'-Chlorobiphenyl-4-yl)-2-hydroxy-4-[2-(4-hydroxyisoxazolidin-2-yl)-2-oxo-acetylamino]pentanoic acid
50. (2R,4R)-5-(3'-Chlorobiphenyl-4-yl)-2-hydroxy-4-[2-(2-oxa-6-aza-spiro[3.3]hept-6-yl)-2-oxo-acetylamino]pentanoic acid Example 5: (2R,4R)-5-(3'-Chlorobiphenyl-4-yl)-4-{[N'-(2,4-dinitrophenyl)-hydrazinooxalyl]-amino}-2-hydroxypentanoic Acid

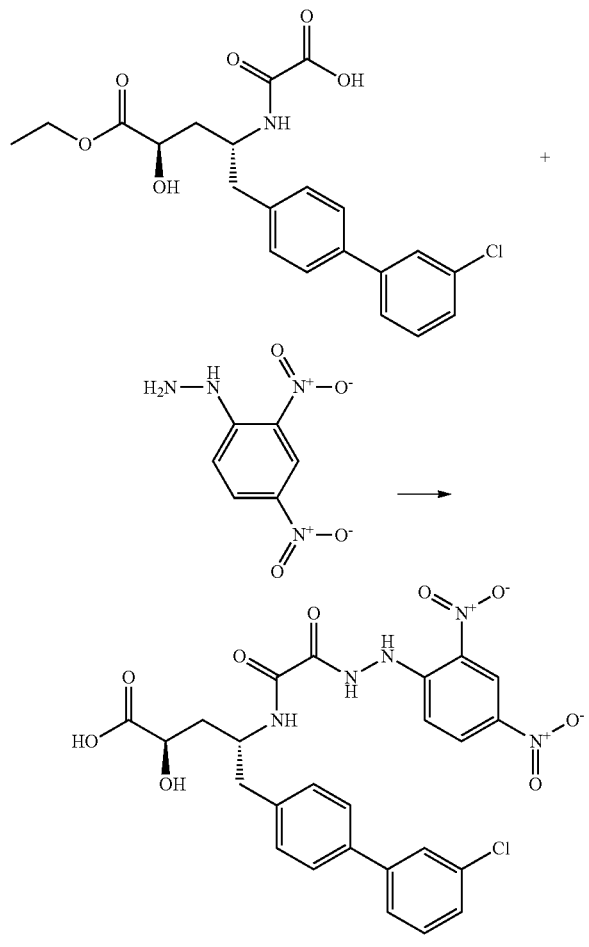

DIPEA (31 μl, 179 μmol) was added to a solution of (2,4-dinitrophenyl)-hydrazine (14 mg, 71 μmol), (2R,4R)-5-(3'-chlorobiphenyl-4-yl)-2-hydroxy-4-(oxalylamino)pentanoic acid ethyl ester (25 mg, 60 μmol) and HATU (34 mg, 89 μmol) in DMF (0.3 mL), and the resulting mixture was stirred at room temperature for 15 minutes. 5 M aqueous LiOH (95 μL, 476 μmol) was added and the mixture was stirred at room temperature for 15 minutes. AcOH (1 mL) was added and the mixture was purified by purified by reverse phase preparative HPLC to yield the title compound as a TFA salt (7.8 mg). MS m/z [M+H]+ calc'd for $C_{25}H_{22}ClN_5O_9$, 572.11; found 572.2.

Example 6

Following the procedures described in the examples herein, and substituting the appropriate starting materials and reagents, the following compounds were prepared as the parent compound or as a TFA salt. These compounds, where X is —C(O)—NR$^9$—NR$^{10}$R$^{11}$, are depicted by formula IIc:

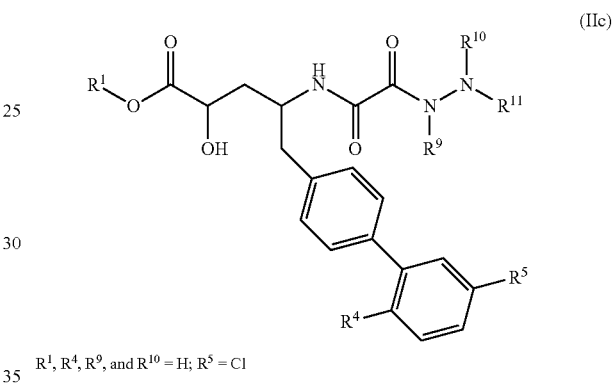

R$^1$, R$^4$, R$^9$, and R$^{10}$ = H; R$^5$ = Cl

| Ex. | R$^{11}$ | Formula | MS m/z: [M + H]+ calcd | found |
|---|---|---|---|---|
| 1 | —CH$_3$ | C$_{20}$H$_{22}$ClN$_3$O$_5$ | 420.12 | 419.2 |
| 2 | —CH$_2$CH(CH$_3$)$_2$ | C$_{23}$H$_{28}$ClN$_3$O$_5$ | 462.17 | 462.2 |

| Ex. | R$^{11}$ | Formula | MS m/z: [M + H]+ calcd | found |
|---|---|---|---|---|
| 3 | 4-pyridyl | C$_{24}$H$_{23}$ClN$_4$O$_5$ | 483.14 | 483.2 |
| 4 | 3-pyridyl | C$_{24}$H$_{23}$ClN$_4$O$_5$ | 483.14 | 483.2 |
| 5 | hydroxypyrimidinyl | C$_{23}$H$_{22}$ClN$_5$O$_6$ | 500.13 | 500.2 |

-continued

| Ex. | R¹¹ | Formula | MS m/z: [M + H]⁺ calcd | found |
|---|---|---|---|---|
| 6 | 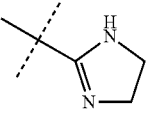 | $C_{22}H_{24}ClN_5O_5$ | 474.15 | 474.2 |
| 7 | 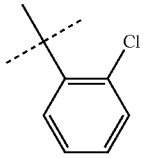 | $C_{25}H_{23}Cl_2N_3O_5$ | 516.10 | 516.2 |
| 8 | 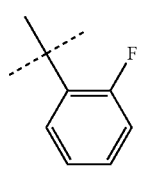 | $C_{25}H_{23}ClFN_3O_5$ | 500.13 | 500.2 |
| 9 | 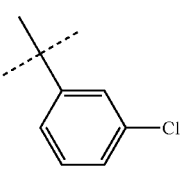 | $C_{25}H_{23}Cl_2N_3O_5$ | 516.10 | 516.2 |
| 10 | 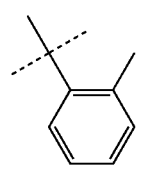 | $C_{26}H_{26}ClN_3O_5$ | 496.16 | 496.2 |
| 11 | 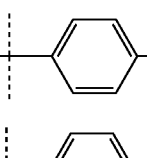 | $C_{26}H_{26}ClN_3O_5$ | 496.16 | 496.2 |
| 12 | 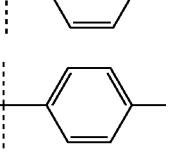 | $C_{25}H_{23}ClFN_3O_5$ | 500.13 | 500.2 |
| 13 | 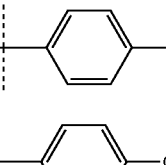 | $C_{25}H_{23}Cl_2N_3O_5$ | 516.10 | 516.2 |
| 14 | 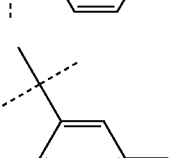 | $C_{25}H_{23}BrClN_3O_5$ | 560.05 | 560.2 |
| 15 | 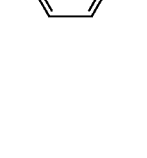 | $C_{26}H_{26}ClN_3O_6$ | 512.15 | 512.2 |
| 16 | 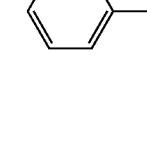 | $C_{26}H_{26}ClN_3O_5$ | 496.16 | 496.2 |
| 17 | 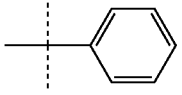 | $C_{25}H_{24}ClN_3O_5$ | 482.14 | 482.2 |

1. (2R,4R)-5-(3'-Chlorobiphenyl-4-yl)-2-hydroxy-4-[(N'-methylhydrazinooxalyl)-amino]pentanoic acid
2. (2R,4R)-5-(3'-Chlorobiphenyl-4-yl)-2-hydroxy-4-[(N'-isobutylhydrazinooxalyl)-amino]pentanoic acid
3. (2R,4R)-5-(3'-Chlorobiphenyl-4-yl)-2-hydroxy-4-[(N'-pyridin-4-yl-hydrazino-oxalyl)-amino]pentanoic acid
4. (2R,4R)-5-(3'-Chlorobiphenyl-4-yl)-2-hydroxy-4-[(N'-pyridin-3-yl-hydrazino-oxalyl)-amino]pentanoic acid
5. (2R,4R)-5-(3'-Chlorobiphenyl-4-yl)-2-hydroxy-4-{[N'-(6-hydroxy-pyrimidin-4-yl)-hydrazinooxalyl]amino}-pentanoic acid
6. (2R,4R)-5-(3'-Chlorobiphenyl-4-yl)-4-{[N'-(4,5-dihydro-1H-imidazol-2-yl)-hydrazinooxalyl]-amino}-2-hydroxy-pentanoic acid
7. (2R,4R)-5-(3'-Chlorobiphenyl-4-yl)-4-{[N'-(2-chloro-phenyl)-hydrazinooxalyl]-amino}-2-hydroxypentanoic acid
8. (2R,4R)-5-(3'-Chlorobiphenyl-4-yl)-4-{[N'-(2-fluoro-phenyl)-hydrazinooxalyl]-amino}-2-hydroxypentanoic acid
9. (2R,4R)-5-(3'-Chlorobiphenyl-4-yl)-4-{[N'-(3-chloro-phenyl)-hydrazinooxalyl]-amino}-2-hydroxypentanoic acid
10. (2R,4R)-5-(3'-Chlorobiphenyl-4-yl)-2-hydroxy-4-[(N'-o-tolyl-hydrazinooxalyl)-amino]-pentanoic acid
11. (2R,4R)-5-(3'-Chlorobiphenyl-4-yl)-2-hydroxy-4-[(N'-p-tolyl-hydrazinooxalyl)-amino]-pentanoic acid
12. (2R,4R)-5-(3'-Chlorobiphenyl-4-yl)-4-{[N'-(4-fluoro-phenyl)-hydrazinooxalyl]-amino}-2-hydroxypentanoic acid
13. (2R,4R)-5-(3'-Chlorobiphenyl-4-yl)-4-{[N'-(4-chloro-phenyl)-hydrazinooxalyl]-amino}-2-hydroxypentanoic acid
14. (2R,4R)-4-{[N'-(4-Bromophenyl)-hydrazinooxalyl]-amino}-5-(3'-chlorobiphenyl-4-yl)-2-hydroxypentanoic acid
15. (2R,4R)-5-(3'-Chlorobiphenyl-4-yl)-2-hydroxy-4-{[N'-(4-methoxyphenyl)-hydrazinooxalyl] amino}pentanoic acid
16. (2R,4R)-5-(3'-Chlorobiphenyl-4-yl)-2-hydroxy-4-[(N'-m-tolylhydrazinooxalyl)-amino]pentanoic acid
17. (2R,4R)-5-(3'-Chlorobiphenyl-4-yl)-2-hydroxy-4-[(N'-phenylhydrazinooxalyl)-amino]pentanoic acid

Example 7: (2R,4R)-5-(3'-Chlorobiphenyl-4-yl)-2-hydroxy-4-{2-[N'-(2-hydroxybenzoyl)hydrazino]-2-oxo-acetylamino}pentanoic Acid

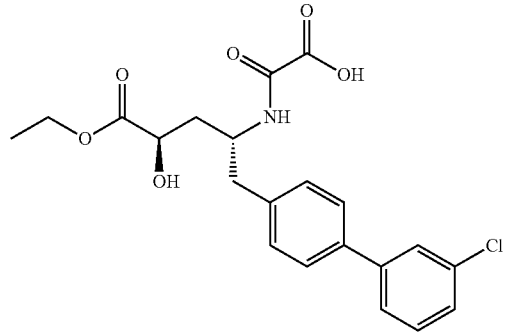

+

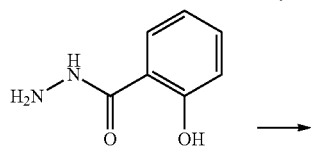

→

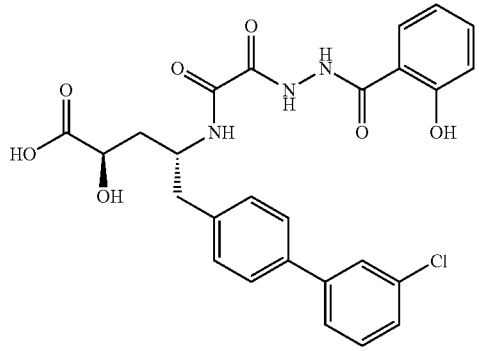

DIPEA (31 μl, 179 μmol) was added to a solution of (2R,4R)-5-(3'-chlorobiphenyl-4-yl)-2-hydroxy-4-(oxalylamino)pentanoic acid ethyl ester (25 mg, 60 μmol), HATU (34 mg, 89 μmol), and 2-hydroxybenzoic acid hydrazide (11 mg, 71 μmol), in DMF (0.3 mL), and the resulting mixture was stirred at room temperature for 15 minutes. 5 M aqueous LiOH (95 μL, 476 μmol) was added and the mixture was stirred at room temperature for 15 minutes. AcOH (1 mL) was added and the mixture was purified by purified by reverse phase preparative HPLC to yield the title compound (0.9 mg). MS m/z [M+H]$^+$ calc'd for $C_{26}H_{24}ClN_3O_7$, 526.13; found 526.2.

Example 8

Following the procedures described in the examples herein, and substituting the appropriate starting materials and reagents, the following compounds were prepared as the parent compound or as a TFA salt. These compounds, where X is —C(O)—NR$^{12}$—NR$^{13}$—C(O)—R$^{14}$, are depicted by formula IId:

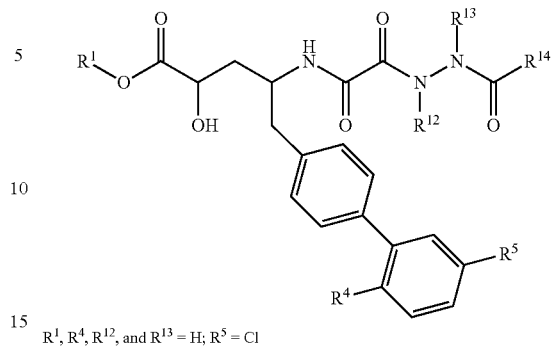

(IId)

$R^1$, $R^4$, $R^{12}$, and $R^{13}$ = H; $R^5$ = Cl

| Ex. | R$^{14}$ | Formula | MS m/z: [M + H]$^+$ calcd | found |
|---|---|---|---|---|
| 1 | benzyl | $C_{27}H_{26}ClN_3O_7$ | 540.15 | 540.2 |
| 2 | 6-chloropyridin-3-yl | $C_{25}H_{22}Cl_2N_4O_6$ | 545.09 | 545.2 |
| 3 | pyridin-3-yl | $C_{25}H_{23}ClN_4O_6$ | 511.13 | 511.2 |
| 4 | pyridin-4-yl | $C_{25}H_{23}ClN_4O_6$ | 511.13 | 511.2 |
| 5 | furan-2-yl | $C_{24}H_{22}ClN_3O_7$ | 500.11 | 500.2 |
| 6 | 2-(N-oxide)phenyl | $C_{26}H_{23}ClN_4O_8$ | 555.12 | 555.9 |

1. (2R,4R)-4-[2-(N'-Benzyloxycarbonyl-hydrazino)-2-oxo-acetylamino]-5-(3'-chloro-biphenyl-4-yl)-2-hydroxypentanoic acid
2. (2R,4R)-5-(3'-Chlorobiphenyl-4-yl)-4-{2-[N'-(6-chloro-pyridine-3-carbonyl)-hydrazino]-2-oxo-acetylamino}-2-hydroxypentanoic acid
3. (2R,4R)-5-(3'-Chlorobiphenyl-4-yl)-2-hydroxy-4-{2-oxo-2-[N'-(pyridine-3-carbonyl)-hydrazino]acetylamino}pentanoic acid
4. (2R,4R)-5-(3'-Chlorobiphenyl-4-yl)-2-hydroxy-4-{2-oxo-2-[N'-(pyridine-4-carbonyl)-hydrazino]acetylamino}pentanoic acid
5. (2R,4R)-5-(3'-Chlorobiphenyl-4-yl)-4-{2-[N'-(furan-2-carbonyl)-hydrazino]-2-oxo-acetylamino}-2-hydroxypentanoic acid 6. (2R,4R)-5-(3'-Chlorobiphenyl-4-yl)-2-hydroxy-4-{2-[N'-(2-nitro-benzoyl)-hydrazino]-2-oxo-acetylamino}pentanoic acid Example 9: (2R,4R)-5-(3'-Chlorobiphenyl-4-yl)-2-hydroxy-4-[(tetrahydropyran-2-carbonyl)amino]pentanoic Acid

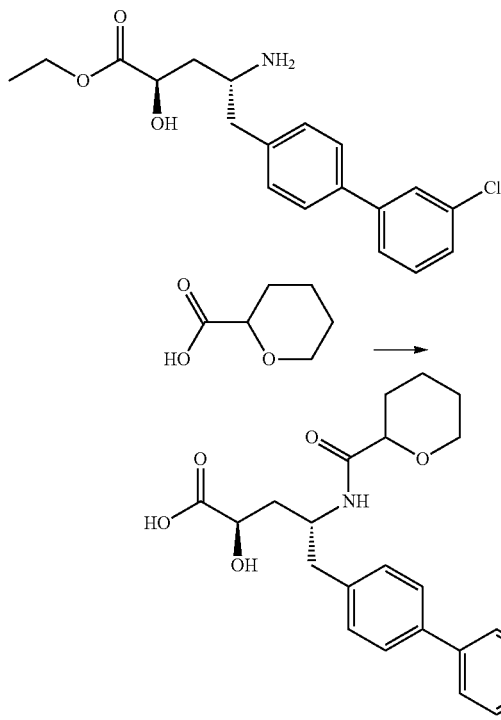

(2R,4R)-4-Amino-5-(3'-chlorobiphenyl-4-yl)-2-hydroxy-pentanoic acid ethyl ester (50 mg, 144 μmol) was added to a solution of tetrahydro-pyran-2-carboxylic acid (1.2 eq., 165 μmol) and HATU (71.1 mg, 187 μmol) in DMF (250 μL), followed by the addition of DIPEA (75 μL, 431 μmol). The resulting mixture was stirred at room temperature for 1 hour. 10 M aqueous LiOH (115 μL, 1.2 mmol) was added and the mixture was stirred for an additional 1 hour. The mixture was washed with DCM (1 mL) and the aqueous layer was acidified with concentrated HCl (250 μL) and extracted with DCM (2×1 mL). The DCM extracts were combined and concentrated in vacuo, and the resulting crude liquid was purified by reverse phase preparative HPLC to yield the title compound (32.6 mg). MS m/z [M+H]$^+$ calc'd for $C_{23}H_{26}ClNO_5$, 432.15; found 432.2.

Example 10

Following the procedures described in the examples herein, and substituting the appropriate starting materials and reagents, the following compounds were prepared as the parent compound. These compounds, where X is —CH($R^{15}$)—OR$^{16}$, are depicted by formula IIe:

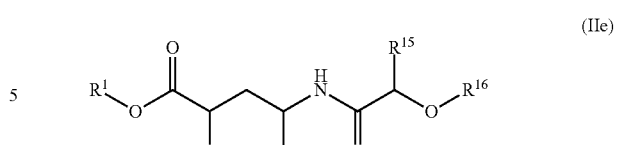

(IIe)

$R^1$, $R^4$, and $R^{15}$ = H; $R^5$ = Cl

| Ex. | $R^{16}$ | Formula | MS m/z: [M + H]+ calcd | found |
|---|---|---|---|---|
| 1 | H | $C_{19}H_{20}ClNO_5$ | 378.10 | 378.2 |
| 2 | —CH$_3$ | $C_{20}H_{22}ClNO_5$ | 392.12 | 392.2 |
| 3 | —CH$_2$CH$_3$ | $C_{21}H_{24}ClNO_5$ | 406.13 | 406.2 |
| 4 | —CH(CH$_3$)$_2$ | $C_{22}H_{26}ClNO_5$ | 420.15 | 420.2 |
| 5 | pyridin-3-yl | $C_{24}H_{23}ClN_2O_5$ | 455.13 | 455.2 |
| 6 | benzyl | $C_{26}H_{26}ClNO_5$ | 468.15 | 468.2 |
| 7 | phenyl | $C_{25}H_{24}ClNO_5$ | 454.13 | 454.2 |
| 8 | 4-hydroxyphenyl | $C_{25}H_{24}ClNO_6$ | 470.13 | 470.2 |
| 9 | 3-methoxyphenyl | $C_{26}H_{26}ClNO_6$ | 484.14 | 484.2 |

1. (2R,4R)-5-(3'-Chlorobiphenyl-4-yl)-2-hydroxy-4-(2-hydroxyacetylamino)-pentanoic acid
2. (2R,4R)-5-(3'-Chlorobiphenyl-4-yl)-2-hydroxy-4-(2-methoxyacetylamino)-pentanoic acid
3. (2R,4R)-5-(3'-Chlorobiphenyl-4-yl)-4-(2-ethoxyacetylamino)-2-hydroxy-pentanoic acid
4. (2R,4R)-5-(3'-Chlorobiphenyl-4-yl)-2-hydroxy-4-(2-isopropoxyacetylamino)-pentanoic acid
5. (2R,4R)-5-(3'-Chlorobiphenyl-4-yl)-2-hydroxy-4-[2-(pyridin-3-yloxy)-acetylamino]-pentanoic acid
6. (2R,4R)-4-(2-Benzyloxy-acetylamino)-5-(3'-chlorobiphenyl-4-yl)-2-hydroxy-pentanoic acid
7. (2R,4R)-5-(3'-Chlorobiphenyl-4-yl)-2-hydroxy-4-(2-phenoxyacetylamino)-pentanoic acid
8. (2R,4R)-5-(3'-Chlorobiphenyl-4-yl)-2-hydroxy-4-[2-(4-hydroxyphenoxy)-acetylamino]-pentanoic acid
9. (2R,4R)-5-(3'-Chlorobiphenyl-4-yl)-2-hydroxy-4-[2-(3-methoxyphenoxy)-acetylamino]-pentanoic acid

Example 11: (2S,4R)-5-(3'-Chlorobiphenyl-4-yl)-2-hydroxymethyl-4-(2-methoxy-acetylamino)-2-methylpentanoic Acid

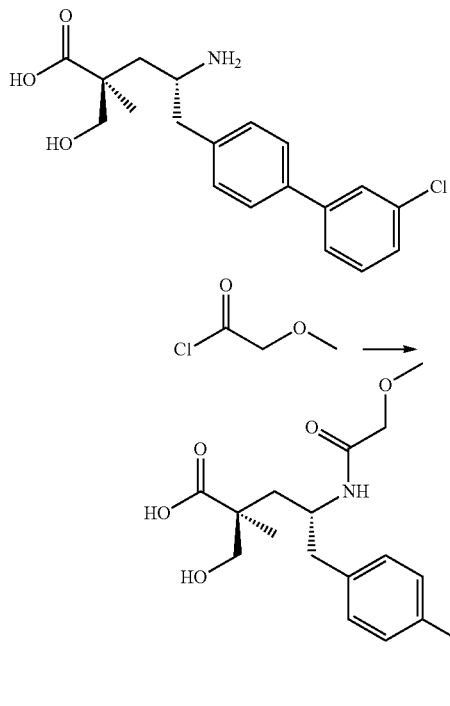

Methoxy-acetyl chloride (7 mg, 30 μmol) was combined with a 0.4 mL solution of 0.075 M of (2S,4R)-4-amino-5-(3'-chlorobiphenyl-4-yl)-2-hydroxymethyl-2-methyl-pentanoic acid (136 mg, 30 μmol) in DCM and Et₃N (110 μL). The resulting mixture was stirred for 10 minutes. The solvent was evaporated and the residue was dissolved in AcOH and purified by preparative HPLC to yield the title compound (2.1 mg). MS m/z [M+H]±calc'd for $C_{22}H_{26}ClNO_5$, 420.15; found 420.2.

Example 12

Following the procedures described in the examples herein, and substituting the appropriate starting materials and reagents, the following compound was prepared as the parent compound. These compounds, where X is —CH($R^{15}$)—$OR^{16}$, are depicted by formula Ve:

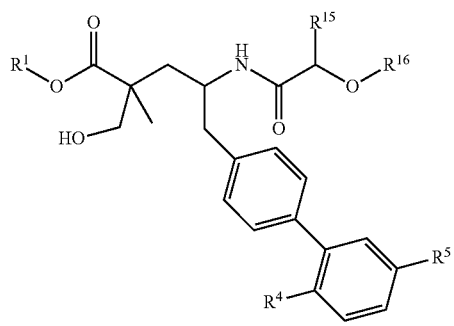

$R^1$, $R^4$, and $R^{15}$ = H; $R^5$ = Cl

| Ex. | $R^{16}$ | Formula | MS m/z: [M + H]⁺ calcd | found |
|---|---|---|---|---|
| 1 | benzyl | $C_{28}H_{30}ClNO_5$ | 496.18 | 496.2 |

1. (2S,4R)-4-(2-Benzyloxyacetylamino)-5-(3'-chlorobiphenyl-4-yl)-2-hydroxymethyl-2-methyl-pentanoic acid

Example 13: (2S,4R)-5-(3'-Chlorobiphenyl-4-yl)-4-formylamino-2-hydroxymethyl-2-methyl-pentanoic Acid

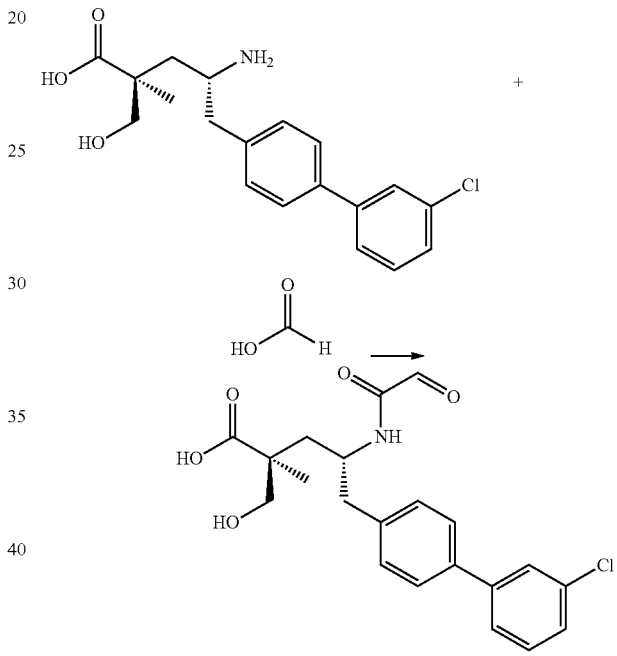

Formic acid (3 mg, 32 μmol) was combined with HATU (12 mg, 32 μmol) and DMF (0.2 mL) and stirred for 5 minutes. DIPEA (17 μl, 96 μmol) was added, followed by (2S,4R)-4-amino-5-(3'-chlorobiphenyl-4-yl)-2-hydroxymethyl-2-methyl-pentanoic acid (79 mg, 38 μmol) pre-dissolved in DMF (0.5 mL) and DIPEA (17 μl, 96 μmol). The resulting mixture was stirred for 15 minutes. The solvent was removed in vacuo and the residue was dissolved in AcOH and purified by preparative HPLC to yield the title compound (0.5 mg). MS m/z [M+H]⁺ calc'd for $C_{20}H_{22}ClNO_4$, 376.12; found 376.2.

Assay 1: In Vitro Assays for the Quantitation of Inhibitor Potencies at Human and Rat NEP, and Human ACE The inhibitory activities of compounds at human and rat neprilysin (EC 3.4.24.11; NEP) and human angiotensin converting enzyme (ACE) were determined using in vitro assays as described below.

Extraction of NEP Activity from Rat Kidneys

Rat NEP was prepared from the kidneys of adult Sprague Dawley rats. Whole kidneys were washed in cold phosphate buffered saline (PBS) and brought up in ice-cold lysis buffer (1% Triton X-114, 150 mM NaCl, 50 mM tris(hydroxymethyl) aminomethane (Tris) pH 7.5; Bordier (1981) *J. Biol. Chem.* 256: 1604-1607) in a ratio of 5 mL of buffer for every gram of kidney. Samples were homogenized on ice using a polytron hand held tissue grinder. Homogenates were centrifuged at 1000×g in a swinging bucket rotor for 5 minutes at 3° C. The pellet was resuspended in 20 mL of ice cold lysis buffer and incubated on ice for 30 minutes. Samples (15-20 mL) were then layered onto 25 mL of ice-cold cushion buffer (6% w/v sucrose, 50 mM pH 7.5 Tris, 150 mM NaCl, 0.06%, Triton X-114), heated to 37° C. for 3-5 minutes and centrifuged at 1000×g in a swinging bucket rotor at room temperature for 3 minutes. The two upper layers were aspirated off, leaving a viscous oily precipitate containing the enriched membrane fraction. Glycerol was added to a concentration of 50% and samples were stored at −20° C. Protein concentrations were quantitated using a BCA detection system with bovine serum albumin (BSA) as a standard.

Enzyme Inhibition Assays

Recombinant human NEP and recombinant human ACE were obtained commercially (R&D Systems, Minneapolis, Minn., catalog numbers 1182-ZN and 929-ZN, respectively). The fluorogenic peptide substrate Mca-D-Arg-Arg-Leu-Dap-(Dnp)-OH (Medeiros et al. (1997) *Braz. J. Med. Biol. Res.* 30:1157-62; Anaspec, San Jose, Calif.) and Abz-Phe-Arg-Lys(Dnp)-Pro-OH (Araujo et al. (2000) *Biochemistry* 39:8519-8525; Bachem, Torrance, Calif.) were used in the NEP and ACE assays respectively.

The assays were performed in 384-well white opaque plates at 37° C. using the fluorogenic peptide substrates at a concentration of 10 µM in Assay Buffer (NEP: 50 mM HEPES, pH 7.5, 100 mM NaCl, 0.01% polyethylene glycol sorbitan monolaurate (Tween-20), 10 µM $ZnSO_4$; ACE: 50 mM HEPES, pH 7.5, 100 mM NaCl, 0.01% Tween-20, 1 µM $ZnSO_4$). The respective enzymes were used at concentrations that resulted in quantitative proteolysis of 1 µM of substrate after 20 minutes at 37° C.

Test compounds were assayed over the range of concentrations from 10 µM to 20 µM. Test compounds were added to the enzymes and incubated for 30 minute at 37° C. prior to initiating the reaction by the addition of substrate. Reactions were terminated after 20 minutes of incubation at 37° C. by the addition of glacial acetic acid to a final concentration of 3.6% (v/v).

Plates were read on a fluorometer with excitation and emission wavelengths set to 320 nm and 405 nm, respectively. Inhibition constants were obtained by nonlinear regression of the data using the equation (GraphPad Software, Inc., San Diego, Calif.):

$$v = v_0/[1+(I/K')]$$

where $v$ is the reaction rate, $v_0$ is the uninhibited reaction rate, I is the inhibitor concentration and K' is the apparent inhibition constant.

Compounds of the invention were tested in this assay and found to have $pK_i$ values at human NEP as follows. In general, either the prodrug compounds did not inhibit the enzyme in this in vitro assay, or the prodrugs were not tested (n.d.) since activity would not be expected

| Ex. | $pK_i$ |
|---|---|
| 1 | 8.0-9.0 |
| 2-1 | 8.0-9.0 |
| 2-2 | 8.0-9.0 |
| 3 | ≥9.0 |
| 4-1 | 7.5-8.0 |
| 4-2 | 7.5-8.0 |
| 4-3 | 7.5-8.0 |
| 4-4 | 8.0-9.0 |
| 4-5 | 7.5-8.0 |
| 4-6 | 8.0-9.0 |
| 4-7 | 8.0-9.0 |
| 4-8 | 7.5-8.0 |
| 4-9 | 8.0-9.0 |
| 4-10 | 7.5-8.0 |
| 4-11 | 7.5-8.0 |
| 4-12 | 8.0-9.0 |
| 4-13 | 8.0-9.0 |
| 4-14 | 7.5-8.0 |
| 4-15 | 8.0-9.0 |
| 4-16 | 8.0-9.0 |
| 4-17 | 7.5-8.0 |
| 4-18 | ≥9.0 |
| 4-19 | 7.5-8.0 |
| 4-20 | ≥9.0 |
| 4-21 | 8.0-9.0 |
| 4-22 | 8.0-9.0 |
| 4-23 | 7.5-8.0 |
| 4-24 | 8.0-9.0 |
| 4-25 | ≥9.0 |
| 4-26 | ≥9.0 |
| 4-27 | 8.0-9.0 |
| 4-28 | 8.0-9.0 |
| 4-29 | 7.5-8.0 |
| 4-30 | 7.5-8.0 |
| 4-31 | 7.5-8.0 |
| 4-32 | 7.5-8.0 |
| 4-33 | 8.0-9.0 |
| 4-34 | 7.5-8.0 |
| 4-35 | 7.5-8.0 |
| 4-36 | 8.0-9.0 |
| 4-37 | 7.5-8.0 |
| 4-38 | 7.5-8.0 |
| 4-39 | 7.5-8.0 |
| 4-40 | 7.5-8.0 |
| 4-41 | 8.0-9.0 |
| 4-42 | 7.5-8.0 |
| 4-43 | 8.0-9.0 |
| 4-44 | 8.0-9.0 |
| 4-45 | 8.0-9.0 |
| 4-46 | 8.0-9.0 |
| 4-47 | 8.0-9.0 |
| 4-48 | 8.0-9.0 |
| 4-49 | 8.0-9.0 |
| 4-50 | 7.5-8.0 |
| 5 | ≥9.0 |
| 6-1 | 7.5-8.0 |
| 6-2 | 7.5-8.0 |
| 6-3 | 8.0-9.0 |
| 6-4 | 8.0-9.0 |
| 6-5 | 8.0-9.0 |
| 6-6 | 7.5-8.0 |
| 6-7 | 8.0-9.0 |
| 6-8 | 8.0-9.0 |
| 6-9 | 8.0-9.0 |
| 6-10 | 8.0-9.0 |
| 6-11 | 8.0-9.0 |
| 6-12 | 8.0-9.0 |
| 6-13 | 8.0-9.0 |
| 6-14 | 8.0-9.0 |
| 6-15 | 8.0-9.0 |
| 6-16 | 8.0-9.0 |
| 6-17 | 8.0-9.0 |
| 7 | ≥9.0 |
| 8-1 | 7.5-8.0 |
| 8-2 | 8.0-9.0 |
| 8-3 | 8.0-9.0 |
| 8-4 | 8.0-9.0 |
| 8-5 | 8.0-9.0 |
| 8-6 | 8.0-9.0 |

-continued

| Ex. | pK$_i$ |
|---|---|
| 9 | 8.0-9.0 |
| 10-1 | 8.0-9.0 |
| 10-2 | 8.0-9.0 |
| 10-3 | 7.5-8.0 |
| 10-4 | 7.5-8.0 |
| 10-5 | 8.0-9.0 |
| 10-6 | 7.5-8.0 |
| 10-7 | 7.5-8.0 |
| 10-8 | 7.5-8.0 |
| 10-9 | 7.5-8.0 |
| 11 | 8.0-9.0 |
| 12 | 7.5-8.0 |
| 13 | 8.0-9.0 |

Assay 2: Pharmacodynamic (PD) Assay for ACE and NEP Activity in Anesthetized Rats Male, Sprague Dawley, normotensive rats are anesthetized with 120 mg/kg (i.p.) of inactin. Once anesthetized, the jugular vein, carotid artery (PE 50 tubing) and bladder (flared PE 50 tubing) catheters are cannulated and a tracheotomy is performed (Teflon Needle, size 14 gauge) to faciliate spontaneous respiration. The animals are then allowed a 60 minute stablization period and kept continuously infused with 5 mL/kg/h of saline (0.9%) throughout, to keep them hydrated and ensure urine production. Body temperature is maintained throughout the experiment by use of a heating pad. At the end of the 60 minute stabilization period, the animals are dosed intravenously (i.v.) with two doses of AngI (1.0 µg/kg, for ACE inhibitor activity) at 15 minutes apart. At 15 minutes post-second dose of AngI, the animals are treated with vehicle or test compound. Five minutes later, the animals are additionally treated with a bolus i.v. injection of atrial natriuretic peptide (ANP; 30 µg/kg). Urine collection (into pre-weighted eppendorf tubes) is started immediately after the ANP treatment and continued for 60 minutes. At 30 and 60 minutes into urine collection, the animals are re-challenged with AngI. Blood pressure measurements are done using the Notocord system (Kalamazoo, Mich.). Urine samples are frozen at −20° C. until used for the cGMP assay. Urine cGMP concentrations are determined by Enzyme Immuno Assay using a commercial kit (Assay Designs, Ann Arbor, Mich., Cat. No. 901-013). Urine volume is determined gravimetrically. Urinary cGMP output is calculated as the product of urine output and urine cGMP concentration. ACE inhibition is assessed by quantifying the % inhibition of pressor response to AngI. NEP inhibition is assessed by quantifying the potentiation of ANP-induced elevation in urinary cGMP output.

Assay 3: In Vivo Evaluation of Antihypertensive Effects in the Conscious SHR Model of Hypertension Spontaneously hypertensive rats (SHR, 14-20 weeks of age) are allowed a minimum of 48 hours acclimation upon arrival at the testing site with free access to food and water. For blood pressure recording, these animals are surgically implanted with small rodent radiotransmitters (telemetry unit; DSI Models TA 11PA-C40 or C50-PXT, Data Science Inc., USA). The tip of the catheter connected to the transmitter is inserted into the descending aorta above the iliac bifurcation and secured in place with tissue adhesive. The transmitter is kept intraperitoneally and secured to the abdominal wall while closing of the abdominal incision with a non-absorbable suture. The outer skin is closed with suture and staples. The animals are allowed to recover with appropriate post-operative care. On the day of the experiment, the animals in their cages are placed on top of the telemetry receiver units to acclimate to the testing environment and baseline recording. After at least of 2 hours baseline measurement is taken, the animals are then dosed with vehicle or test compound and followed out to 24 hours post-dose blood pressure measurement. Data is recorded continuously for the duration of the study using Notocord software (Kalamazoo, Mich.) and stored as electronic digital signals. Parameters measured are blood pressure (systolic, diastolic and mean arterial pressure) and heart rate.

Assay 4: In Vivo Evaluation of Antihypertensive Effects in the Conscious DOCA-Salt Rat Model of Hypertension CD rats (male, adult, 200-300 grams, Charles River Laboratory, USA) are allowed a minimum of 48 hours acclimation upon arrival at the testing site before they are placed on a high salt diet. One week after the start of the high salt diet (8% in food or 1% NaCl in drinking water), a deoxycorticosterone acetate (DOCA) pellet (100 mg, 90 days release time, Innovative Research of America, Sarasota, Fla.) is implanted subcutaneously and unilateral nephrectomy is performed. At this time, the animals are also surgically implanted with small rodent radiotransmitters for blood pressure measurement (see Assay 3 for details). The animals are allowed to recover with appropriate post-operative care. Study design, data recording, and parameters measured is similar to that described for Assay 3.

Assay 5: In Vivo Evaluation of Antihypertensive Effects in the Conscious Dahl/SS Rat Model of Hypertension Male, Dahl salt sensitive rats (Dahl/SS, 6-7 weeks of age from Charles River Laboratory, USA) are allowed at least 48 hours of acclimation upon arrival at the testing site before they were placed on a 8% NaCl high salt diet (TD.92012, Harlan, USA) then surgically implanted with small rodent radiotransmitters for blood pressure measurement (see Assay 3 for details). The animals are allowed to recover with appropriate post-operative care. At approximately 4 to 5 weeks from the start of high salt diet, these animals are expected to become hypertensive. Once the hypertension level is confirmed, these animals are used for the study while continued with the high salt diet to maintain their hypertension level. Study design, data recording, and parameters measured is similar to that described in Assay 3.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents and patent applications cited herein are hereby incorporated by reference in their entirety to the same extent as if each document had been individually incorporated by reference herein.

What is claimed is:

1. A compound of:

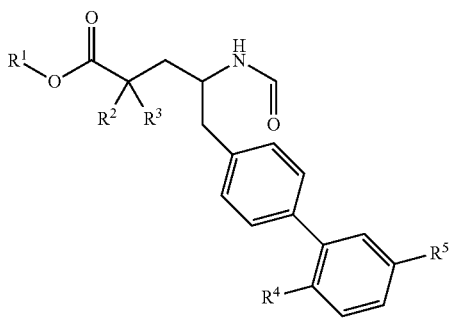

where:
R[1] is selected from the group consisting of H; $C_{1-8}$alkyl optionally substituted with one or more fluoro atoms; $C_{1-3}$alkylene-$C_{6-10}$aryl; $C_{1-3}$alkylene-$C_{1-9}$heteroaryl; $C_{3-7}$cycloalkyl; $C_{2-3}$alkylene-OH; —[(CH$_2$)$_2$O]$_{1-3}$CH$_3$; $C_{1-6}$alkylene-OC(O)R[20]; $C_{1-6}$alkylene-NR[21]R[22]; —CH$_2$CH(NH$_2$)—COOCH$_3$; $C_{1-6}$alkylene-C(O)R[23]; $C_{0-6}$alkylenemorpholine; $C_{1-6}$alkylene-SO$_2$—$C_{1-6}$alkyl;

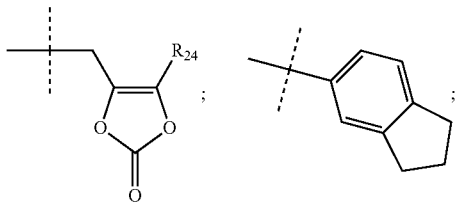

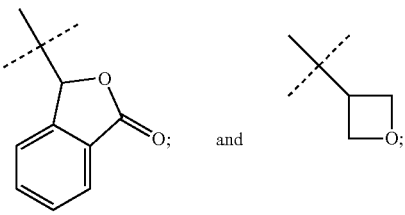

R[2] is —CH$_2$OH and R[3] is —CH$_3$;

R[4] and R[5] are independently selected from the group consisting of hydrogen, halo, —OH, —CH$_3$, —OCH$_3$, —CN, and —CF$_3$;

or a pharmaceutically-acceptable salt thereof.

2. (2S,4R)-5-(3'-chlorobiphenyl-4-yl)-4-formylamino-2-hydroxymethyl-2-methyl-pentanoic acid or a pharmaceutically-acceptable salt thereof.

3. A pharmaceutical composition comprising the compound of claim 1 or 2 and a pharmaceutically acceptable carrier.

4. The pharmaceutical composition of claim 3, further comprising an AT$_1$ receptor antagonist.

5. A method for treating hypertension, heart failure, or renal disease, comprising administering to a patient a therapeutically effective amount of the compound of claim 1 or 2.

* * * * *